US012528855B2

(12) United States Patent
Aggarwal et al.

(10) Patent No.: US 12,528,855 B2
(45) Date of Patent: Jan. 20, 2026

(54) KRAS VARIANT MRNA MOLECULES

(71) Applicant: CureVac SE, Tübingen (DE)

(72) Inventors: Amit Aggarwal, Indianapolis, IN (US); Katja Fiedler, Tübingen (DE); Ulrike Gnad-Vogt, Tübingen (DE); Regina Heidenreich, Tübingen (DE); Mythili Koneru, Indianapolis, IN (US); Gregory D. Plowman, Indianapolis, IN (US)

(73) Assignee: CureVac SE, Tübingen (DE)

( * ) Notice: Subject to any disclaimer, the term of this patent is extended or adjusted under 35 U.S.C. 154(b) by 935 days.

(21) Appl. No.: 17/413,654

(22) PCT Filed: Dec. 6, 2019

(86) PCT No.: PCT/US2019/064976
§ 371 (c)(1),
(2) Date: Jun. 14, 2021

(87) PCT Pub. No.: WO2020/123300
PCT Pub. Date: Jun. 18, 2020

(65) Prior Publication Data

US 2022/0340641 A1 Oct. 27, 2022

Related U.S. Application Data

(60) Provisional application No. 62/788,285, filed on Jan. 4, 2019, provisional application No. 62/779,858, filed on Dec. 14, 2018.

(51) Int. Cl.

| | |
|---|---|
| ***C07K 14/74*** | (2006.01) |
| ***A61K 38/00*** | (2006.01) |
| ***A61K 47/18*** | (2017.01) |
| ***A61K 47/24*** | (2006.01) |
| ***A61K 47/28*** | (2006.01) |
| ***C07K 14/705*** | (2006.01) |
| ***C12N 9/14*** | (2006.01) |
| ***C12N 15/62*** | (2006.01) |

(52) U.S. Cl.
CPC ........ *C07K 14/70539* (2013.01); *A61K 47/18* (2013.01); *A61K 47/183* (2013.01); *A61K 47/24* (2013.01); *A61K 47/28* (2013.01); *C07K 14/70521* (2013.01); *C12N 9/14* (2013.01); *C12N 15/625* (2013.01); *C12Y 306/05002* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 8,217,016 | B2 | 7/2012 | Hoerr et al. |
| 8,383,340 | B2 | 2/2013 | Ketterer et al. |
| 8,703,906 | B2 | 4/2014 | Baumhof et al. |
| 8,968,746 | B2 | 3/2015 | Baumhof et al. |
| 9,155,788 | B2 | 10/2015 | Hoerr et al. |
| 9,226,959 | B2 | 1/2016 | Kramps et al. |
| 9,234,013 | B2 | 1/2016 | Thess et al. |
| 9,314,535 | B2 | 4/2016 | Baumhof et al. |
| 9,352,028 | B2 | 5/2016 | Barner et al. |
| 9,402,887 | B2 | 8/2016 | Probst et al. |
| 9,421,255 | B2 | 8/2016 | Baumhof et al. |
| 9,433,669 | B2 | 9/2016 | Hoerr et al. |
| 9,433,670 | B2 | 9/2016 | Hoerr et al. |
| 9,439,956 | B2 | 9/2016 | Hoerr et al. |
| 9,447,431 | B2 | 9/2016 | Thess et al. |
| 9,463,228 | B2 | 10/2016 | Hoerr et al. |
| 9,572,874 | B2 | 2/2017 | Fotin-Mleczek et al. |
| 9,616,084 | B2 | 4/2017 | Mutzke |
| 9,623,095 | B2 | 4/2017 | Kallen et al. |
| 9,655,955 | B2 | 5/2017 | Hoerr et al. |
| 9,669,089 | B2 | 6/2017 | Thess et al. |
| 9,683,233 | B2 | 6/2017 | Thess |
| 9,688,729 | B2 | 6/2017 | Kramps et al. |
| 9,737,595 | B2 | 8/2017 | Lorenz et al. |
| 9,839,697 | B2 | 12/2017 | Thess et al. |
| 9,890,391 | B2 | 2/2018 | Thess et al. |
| 9,907,862 | B2 | 3/2018 | Baumhof et al. |
| 9,974,845 | B2 | 5/2018 | Fotin-Mleczek et al. |
| 10,010,592 | B2 | 7/2018 | Thess et al. |
| 10,017,826 | B2 | 7/2018 | von der Mülbe et al. |
| 10,047,375 | B2 | 8/2018 | Thess |

(Continued)

FOREIGN PATENT DOCUMENTS

| | | | |
|---|---|---|---|
| EP | 3424524 | 1/2019 | |
| WO | WO-9507707 A1 * | 3/1995 | ........... C07K 14/001 |

(Continued)

OTHER PUBLICATIONS

Pruitt, Scott K., et al. "Enhancement of anti-tumor immunity through local modulation of CTLA-4 and GITR by dendritic cells." European journal of immunology 41.12 (2011): 3553-3563 and S1-S8. (Year: 2011).*

(Continued)

*Primary Examiner* — Bethany P Barham
*Assistant Examiner* — Peter Anthopolos
(74) *Attorney, Agent, or Firm* — pH IP Law

(57) ABSTRACT

The present invention provides an mRNA molecule encoding at least one KRAS variant peptide. Further, the invention provides a pharmaceutical composition and kit comprising the mRNA molecule. The mRNA molecule, pharmaceutical composition and kit are useful for treating cancer.

19 Claims, No Drawings

Specification includes a Sequence Listing.

(56) References Cited

U.S. PATENT DOCUMENTS 10,080,809 B2 9/2018 Thess
10,111,967 B2 10/2018 Fotin-Mleczek et al.
10,111,968 B2 10/2018 Thess et al.
10,117,920 B2 11/2018 Fotin-Mleczek et al.
10,150,797 B2 12/2018 Kramps et al.
10,166,283 B2 1/2019 Thess et al.
10,172,935 B2 1/2019 Kallen et al.
10,188,748 B2 1/2019 on der Mülbe et al.
10,232,024 B2 3/2019 Thess et al.
10,293,058 B2 5/2019 Fotin-Mleczek et al.
10,293,060 B2 5/2019 Baumhof
10,307,472 B2 6/2019 Fotin-Mleczek et al.
10,369,216 B2 8/2019 Fotin-Mleczek et al.
10,434,154 B2 10/2019 Probst et al.
10,434,158 B2 10/2019 Fotin-Mleczek et al.
10,441,653 B2 10/2019 Hoerr et al.
10,501,768 B2 12/2019 Eber et al.
10,517,827 B2 12/2019 Eber et al.
10,568,958 B2 2/2020 Baumhof et al.
10,568,972 B2 2/2020 von der Mülbe et al.
10,588,959 B2 3/2020 Kallen et al.
10,596,252 B2 3/2020 Kallen et al.
10,610,605 B2 4/2020 Thess et al.
10,648,017 B2 5/2020 Wochner
10,653,768 B2 5/2020 Mutzke et al.
10,653,799 B2 5/2020 Thess et al.
10,682,406 B2 6/2020 Thess et al.
10,682,426 B2 6/2020 Schnee et al.
10,711,315 B2 7/2020 von der Mülbe et al.
10,729,654 B2 8/2020 Eber et al.
10,729,761 B2 8/2020 Kallen et al.
10,738,306 B2 8/2020 Thess
10,751,424 B2 8/2020 Baumhof et al.
10,760,070 B2 9/2020 Funkner et al.
10,780,054 B2 9/2020 Ketterer et al.
10,799,577 B2 10/2020 Thess et al.
10,799,602 B2 10/2020 Baumhof
10,837,039 B2 11/2020 Wochner et al.
10,869,935 B2 12/2020 Fotin-Mleczek et al.
10,898,584 B2 1/2021 Schlake et al.
10,898,589 B2 1/2021 Thess et al.
10,912,826 B2 2/2021 Thess et al.
10,918,740 B2 2/2021 Fotin-Mleczek et al.
10,988,754 B2 4/2021 Fotin-Mleczek et al.
11,034,729 B2 6/2021 Kramps et al.
11,078,247 B2 8/2021 Fotin-Mleczek et al.
11,110,156 B2 9/2021 Thess et al.
11,110,157 B2 9/2021 Fotin-Mleczek et al.
11,110,166 B2 9/2021 Fotin-Mleczek et al.
11,135,312 B2 10/2021 von der Mülbe et al.
11,141,474 B2 10/2021 Rauch et al.
11,141,476 B2 10/2021 Rauch
11,149,278 B2 10/2021 Thess et al.
11,179,337 B2 11/2021 Eber et al.
11,225,682 B2 1/2022 Reichert et al.
11,241,493 B2 2/2022 Rauch et al.
11,248,223 B2 2/2022 Yazdan Panah et al.
11,254,951 B2 2/2022 Thess
11,266,735 B2 3/2022 Kallen et al.
11,268,157 B2 3/2022 von der Mülbe et al.
11,274,293 B2 3/2022 Funkner et al.
11,279,923 B2 3/2022 Funkner et al.
11,286,492 B2 3/2022 Thess et al.
11,345,920 B2 5/2022 Thess et al.
11,369,691 B2 6/2022 von der Mülbe et al.
11,369,694 B2 6/2022 Schnee et al.
11,384,375 B2 7/2022 Roos et al.
11,413,346 B2 8/2022 Rauch et al.
11,421,038 B2 8/2022 Hoerr et al.
11,433,027 B2 9/2022 Eber et al.
11,446,250 B2 9/2022 Ketterer et al.
11,458,193 B2 10/2022 Lorenz et al.
11,458,195 B2 10/2022 Fotin-Mleczek et al.
11,464,836 B2 10/2022 Horscroft et al.
11,464,847 B2 10/2022 Jasny et al.
11,471,525 B2 10/2022 Rauch et al.
11,478,552 B2 10/2022 Baumhof et al.
11,491,112 B2 11/2022 Ketterer et al.
11,524,066 B2 12/2022 Jasny et al.
11,525,158 B2 12/2022 Yazdan Panah et al.
11,534,405 B2 12/2022 Eber et al.
11,542,490 B2 1/2023 Horscroft et al.
11,559,570 B2 1/2023 Fotin-Mleczek et al.
11,576,966 B2 2/2023 Rauch et al.
11,596,686 B2 3/2023 Rauch et al.
11,596,699 B2 3/2023 Fotin-Mleczek et al.
11,602,557 B2 3/2023 Petsch et al.
11,608,513 B2 3/2023 Roos et al.
11,661,634 B2 5/2023 von der Mülbe et al.
11,667,910 B2 6/2023 Funkner et al.
11,690,910 B2 7/2023 Baumhof et al.
11,692,002 B2 7/2023 Heinz et al.
11,697,816 B2 7/2023 Grund et al.
11,723,967 B2 8/2023 Petsch et al.
11,739,125 B2 8/2023 Kramps et al.
11,739,335 B2 8/2023 Chevessier-Tünnesen et al.
11,760,992 B2 9/2023 Funkner et al.
11,761,009 B2 9/2023 Thess et al.
11,786,590 B2 10/2023 Rauch et al.
2005/0032730 A1 2/2005 von der Mülbe et al.
2005/0059624 A1 3/2005 Hoerr et al.
2005/0250723 A1 11/2005 Hoerr et al.
2006/0188490 A1 8/2006 Hoerr et al.
2008/0025944 A1 1/2008 Hoerr et al.
2008/0267873 A1 10/2008 Hoerr et al.
2009/0324584 A1 12/2009 Hoerr et al.
2010/0048883 A1 2/2010 Ketterer et al.
2010/0189729 A1 7/2010 Hoerr et al.
2010/0203076 A1 8/2010 Fotin-Mleczek et al.
2010/0291156 A1 11/2010 Barner et al.
2010/0305196 A1 12/2010 Probst et al.
2011/0053829 A1 3/2011 Baumhof et al.
2011/0250225 A1 10/2011 Fotin-Mleczek et al.
2012/0021043 A1 1/2012 Kramps et al.
2012/0258046 A1 10/2012 Mutzke
2013/0129754 A1 5/2013 Thess et al.
2013/0142818 A1 6/2013 Baumhof et al.
2013/0259879 A1 10/2013 Baumhof et al.
2013/0280283 A1 10/2013 Lorenz et al.
2013/0295043 A1 11/2013 Kallen et al.
2013/0336998 A1 12/2013 Kallen et al.
2015/0037326 A1 2/2015 Butler-Ransohoff et al.
2015/0050302 A1 2/2015 Thess
2015/0057340 A1 2/2015 Thess et al.
2015/0093413 A1 4/2015 Thess et al.
2015/0118183 A1 4/2015 Baumhof
2015/0118264 A1 4/2015 Baumhof et al.
2015/0165006 A1 6/2015 Thess et al.
2015/0184195 A1 7/2015 Thess et al.
2015/0218554 A1 8/2015 Thess
2015/0306249 A1 10/2015 Baumhof et al.
2015/0320847 A1 11/2015 Thess et al.
2016/0130345 A1 5/2016 Fotin-Mleczek et al.
2016/0166668 A1 6/2016 Kallen et al.
2016/0166678 A1 6/2016 Kallen et al.
2016/0166710 A1 6/2016 Baumhof
2016/0166711 A1 6/2016 Schnee et al.
2016/0168207 A1 6/2016 Kramps et al.
2016/0168227 A1 6/2016 Kallen et al.
2016/0235864 A1 8/2016 Schlake et al.
2016/0304883 A1 10/2016 Grund et al.
2016/0304938 A1 10/2016 Wochner
2016/0326575 A1 11/2016 von der Mülbe
2016/0331844 A1 11/2016 Fotin-Mleczek et al.
2017/0014496 A1 1/2017 Fotin-Mleczek et al.
2017/0029847 A1 2/2017 Thess
2017/0114378 A1 4/2017 Wochner et al.
2017/0252430 A1 9/2017 Fotin-Mleczek et al.
2017/0326225 A1 11/2017 Rauch et al.
2018/0044687 A1 2/2018 Thess et al.
2018/0125952 A1 5/2018 Fotin-Mleczek et al.
2018/0126003 A1 5/2018 Hoerr
2018/0142275 A1 5/2018 Roos et al.
2018/0147146 A1 5/2018 Eber et al.

(56) References Cited

U.S. PATENT DOCUMENTS

| | | | |
|---|---|---|---|
| 2018/0148727 | A1 | 5/2018 | Grund et al. |
| 2018/0201967 | A1 | 7/2018 | Eber et al. |
| 2018/0208957 | A1 | 7/2018 | Roos et al. |
| 2018/0214537 | A1 | 8/2018 | Mutzke et al. |
| 2018/0237786 | A1 | 8/2018 | Schlake et al. |
| 2018/0237817 | A1 | 8/2018 | Roos et al. |
| 2018/0243219 | A1 | 8/2018 | Ketterer et al. |
| 2018/0296663 | A1 | 10/2018 | Hipp et al. |
| 2018/0298372 | A1 | 10/2018 | Funkner et al. |
| 2018/0312545 | A1 | 11/2018 | Baumhof et al. |
| 2018/0312549 | A1 * | 11/2018 | Ciaramella ........ A61K 31/7105 |
| 2018/0371392 | A1 | 12/2018 | Mayer et al. |
| 2019/0010485 | A1 | 1/2019 | Yazdan Panah et al. |
| 2019/0017100 | A1 | 1/2019 | Wochner et al. |
| 2019/0024096 | A1 | 1/2019 | Schmid et al. |
| 2019/0040378 | A1 | 2/2019 | Fotin-Mleczek et al. |
| 2019/0049414 | A1 | 2/2019 | Wochner et al. |
| 2019/0083602 | A1 | 3/2019 | Roos et al. |
| 2019/0100784 | A1 | 4/2019 | Eber et al. |
| 2019/0125857 | A1 | 5/2019 | Rauch et al. |
| 2019/0133950 | A1 | 5/2019 | Eber et al. |
| 2019/0160164 | A1 | 5/2019 | Rauch et al. |
| 2019/0177714 | A1 | 6/2019 | Kunze et al. |
| 2019/0185859 | A1 | 6/2019 | Fotin-Mleczek et al. |
| 2019/0194760 | A1 | 6/2019 | Koch et al. |
| 2019/0225971 | A1 | 7/2019 | Williams |
| 2019/0241633 | A1 | 8/2019 | Fotin-Mleczek et al. |
| 2019/0249219 | A1 | 8/2019 | Reichert et al. |
| 2019/0336608 | A1 | 11/2019 | Baumhof et al. |
| 2019/0336611 | A1 | 11/2019 | Baumhof et al. |
| 2019/0343933 | A1 | 11/2019 | Horscroft et al. |
| 2019/0343942 | A1 | 11/2019 | Fotin-Mleczek et al. |
| 2019/0351044 | A1 | 11/2019 | Jasny et al. |
| 2019/0351047 | A1 | 11/2019 | Jasny et al. |
| 2019/0351048 | A1 | 11/2019 | Rauch |
| 2019/0381180 | A1 | 12/2019 | Baumhof et al. |
| 2020/0023076 | A1 | 1/2020 | Fotin-Mleczek et al. |
| 2020/0085852 | A1 | 3/2020 | Fotin-Mleczek |
| 2020/0085944 | A1 | 3/2020 | Heidenreich et al. |
| 2020/0149026 | A1 | 5/2020 | Horscroft et al. |
| 2020/0163878 | A1 | 5/2020 | Baumhof et al. |
| 2020/0179526 | A1 | 6/2020 | Baumhof et al. |
| 2020/0318097 | A1 | 10/2020 | Funkner et al. |
| 2020/0392572 | A1 | 12/2020 | Yazdan Panah et al. |
| 2021/0030864 | A1 | 2/2021 | Petsch et al. |
| 2021/0069315 | A1 | 3/2021 | Baumhof et al. |
| 2021/0162037 | A1 | 6/2021 | Jasny et al. |
| 2021/0170017 | A1 | 6/2021 | Lutz et al. |
| 2021/0180106 | A1 | 6/2021 | Wochner et al. |
| 2021/0205434 | A1 | 7/2021 | Petsch et al. |
| 2021/0260178 | A1 | 8/2021 | Jasny et al. |
| 2021/0261897 | A1 | 8/2021 | Yazdan Panah et al. |
| 2021/0361761 | A1 | 11/2021 | Lutz et al. |
| 2021/0379181 | A1 | 12/2021 | Rauch et al. |
| 2021/0403925 | A1 | 12/2021 | Chevessier-Tünnesen et al. |
| 2022/0040281 | A1 | 2/2022 | Schwendt et al. |
| 2022/0073962 | A1 | 3/2022 | Schwenger et al. |
| 2022/0133908 | A1 | 5/2022 | Rejman et al. |
| 2022/0144877 | A1 | 5/2022 | Heinz et al. |
| 2022/0211838 | A1 | 7/2022 | Oostvogels et al. |
| 2022/0233568 | A1 | 7/2022 | Schlake et al. |
| 2022/0296628 | A1 | 9/2022 | Thess et al. |
| 2022/0313813 | A1 | 10/2022 | Rauch et al. |
| 2022/0340641 | A1 | 10/2022 | Aggarwal et al. |
| 2023/0064106 | A1 | 3/2023 | Heinz et al. |
| 2023/0090515 | A1 | 3/2023 | Navarro et al. |

FOREIGN PATENT DOCUMENTS

| | | | |
|---|---|---|---|
| WO | WO-2015024667 A1 * | 2/2015 | ............. A61K 38/00 |
| WO | WO 2018/144775 | 8/2018 | |
| WO | WO-2018144775 A1 * | 8/2018 | ......... A61K 39/0011 |
| WO | WO 2021/254593 | 12/2021 | |
| WO | WO 2022/023559 | 2/2022 | |
| WO | WO 2022/043551 | 3/2022 | |
| WO | WO 2022/049093 | 3/2022 | |
| WO | WO 2022/112498 | 6/2022 | |
| WO | WO 2022/135993 | 6/2022 | |
| WO | WO 2022/162027 | 8/2022 | |

OTHER PUBLICATIONS

Chakraborty et al., "Ras proteins as therapeutic targets," *Biochemical Society Transactions*, 46(5):1303-1311, 2018.

EBI Accession No. GSP: BGA58013, "HsCTLA4-V2-GgOva-V3-PADRE-HsCTLA4 SEQ 77063," Mar. 7, 2019.

Fiedler et al., "mRNA cancer vaccines," *Current Strategies in Cancer Gene Therapy*, 209:61-85, 2016.

Ostrem et al., "K-Ras(G12C) inhibitors allosterically control GTP affinity and effector interactions," *Nature*, 503(7477):548-551, 2013.

PCT International Search Report and Written Opinion issued in International Application No. PCT/US2019/064976, mailed Jul. 21, 2020.

* cited by examiner

SEQUENCE LISTING

<160> NUMBER OF SEQ ID NOS: 112

<210> SEQ ID NO 1
<211> LENGTH: 44

<212> TYPE: RNA
<213> ORGANISM: Artificial Sequence
<220> FEATURE:
<223> OTHER INFORMATION: muag 3'-UTR

<400> SEQUENCE: 1
gcccgauggg ccucccaacg ggcccuccuc cccuccuugc accg 44

<210> SEQ ID NO 2
<211> LENGTH: 24
<212> TYPE: RNA
<213> ORGANISM: Artificial Sequence
<220> FEATURE:
<223> OTHER INFORMATION: histone stem-loop

<400> SEQUENCE: 2
caaaggcucu uuucagagcc acca 24

<210> SEQ ID NO 3
<211> LENGTH: 36
<212> TYPE: PRT
<213> ORGANISM: Artificial Sequence
<220> FEATURE:
<223> OTHER INFORMATION: CTLA4 (1-35)

<400> SEQUENCE: 3

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Ala
        35
```

<210> SEQ ID NO 4
<211> LENGTH: 108
<212> TYPE: RNA
<213> ORGANISM: Artificial Sequence
<220> FEATURE:
<223> OTHER INFORMATION: CTLA4 (1-35)

<400> SEQUENCE: 4
auggcuugcc uuggauuuca gcggcacaag gcucagcuga accuggcuac caggaccugg 60
cccugcacuc uccuguuuuu ucuucucuuc aucccugucu ucugcgca 108

<210> SEQ ID NO 5
<211> LENGTH: 108
<212> TYPE: RNA
<213> ORGANISM: Artificial Sequence
<220> FEATURE:
<223> OTHER INFORMATION: CTLA4 (1-35)

<400> SEQUENCE: 5
auggccugcc ugggcuucca gcgccacaag gcccagcuca accuggcgac ccggaccugg 60
cccugcacgc uccuguucuu ccugcuguuc aucccggugu ucugcgca 108

<210> SEQ ID NO 6
<211> LENGTH: 108
<212> TYPE: RNA
<213> ORGANISM: Artificial Sequence
<220> FEATURE:
<223> OTHER INFORMATION: CTLA4 (1-35)

<400> SEQUENCE: 6
auggccugcc ugggcuucca gagacacaag gcucaacuca accuugcaac caggacaugg 60

```
cccuguacuc uguuguuuuu cuuacuguuu aucccugugu ucugcgcc                108


<210> SEQ ID NO 7
<211> LENGTH: 108
<212> TYPE: RNA
<213> ORGANISM: Artificial Sequence
<220> FEATURE:
<223> OTHER INFORMATION: CTLA4 (1-35)

<400> SEQUENCE: 7

auggccugcc ugggcuucca gagacacaag gcccagcuga accuggccac cagaaccugg      60

cccugcaccc ugcuguucuu ccugcuguuc auccccgugu ucugcgcc                108


<210> SEQ ID NO 8
<211> LENGTH: 29
<212> TYPE: PRT
<213> ORGANISM: Artificial Sequence
<220> FEATURE:
<223> OTHER INFORMATION: Kras (G12C)

<400> SEQUENCE: 8

Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val
            20                  25


<210> SEQ ID NO 9
<211> LENGTH: 29
<212> TYPE: PRT
<213> ORGANISM: Artificial Sequence
<220> FEATURE:
<223> OTHER INFORMATION: Kras (G12D)

<400> SEQUENCE: 9

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val
            20                  25


<210> SEQ ID NO 10
<211> LENGTH: 29
<212> TYPE: PRT
<213> ORGANISM: Artificial Sequence
<220> FEATURE:
<223> OTHER INFORMATION: Kras (G12R)

<400> SEQUENCE: 10

Met Thr Glu Tyr Lys Leu Val Val Val Gly Ala Arg Gly Val Gly Lys
1               5                   10                  15

Ser Ala Leu Thr Ile Gln Leu Ile Gln Asn His Phe Val
            20                  25


<210> SEQ ID NO 11
<211> LENGTH: 29
<212> TYPE: PRT
<213> ORGANISM: Artificial Sequence
<220> FEATURE:
<223> OTHER INFORMATION: Kras (G12V)

<400> SEQUENCE: 11

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val
```

-continued 20 25

<210> SEQ ID NO 12
<211> LENGTH: 29
<212> TYPE: PRT
<213> ORGANISM: Artificial Sequence
<220> FEATURE:
<223> OTHER INFORMATION: Kras (G13D)

<400> SEQUENCE: 12

Met Thr Glu Tyr Lys Leu Val Val Val Gly Ala Gly Asp Val Gly Lys
1 5 10 15

Ser Ala Leu Thr Ile Gln Leu Ile Gln Asn His Phe Val
20 25

<210> SEQ ID NO 13
<211> LENGTH: 87
<212> TYPE: RNA
<213> ORGANISM: Artificial Sequence
<220> FEATURE:
<223> OTHER INFORMATION: Kras (G12C)

<400> SEQUENCE: 13
augacugaau auaaacuugu gguaguugga gcuugcggcg uaggcaagag ugccuugacg 60
auacagcuaa uucagaauca uuuugug 87

<210> SEQ ID NO 14
<211> LENGTH: 87
<212> TYPE: RNA
<213> ORGANISM: Artificial Sequence
<220> FEATURE:
<223> OTHER INFORMATION: Kras (G12D)

<400> SEQUENCE: 14
augacugaau auaaacuugu gguaguugga gcugacggcg uaggcaagag ugccuugacg 60
auacagcuaa uucagaauca uuuugug 87

<210> SEQ ID NO 15
<211> LENGTH: 87
<212> TYPE: RNA
<213> ORGANISM: Artificial Sequence
<220> FEATURE:
<223> OTHER INFORMATION: Kras (G12R)

<400> SEQUENCE: 15
augacugaau auaaacuugu gguaguugga gcuagaggcg uaggcaagag ugccuugacg 60
auacagcuaa uucagaauca uuuugug 87

<210> SEQ ID NO 16
<211> LENGTH: 87
<212> TYPE: RNA
<213> ORGANISM: Artificial Sequence
<220> FEATURE:
<223> OTHER INFORMATION: Kras (G12V)

<400> SEQUENCE: 16
augacugaau auaaacuugu gguaguugga gcugugggcg uaggcaagag ugccuugacg 60
auacagcuaa uucagaauca uuuugug 87

<210> SEQ ID NO 17
<211> LENGTH: 87
<212> TYPE: RNA
<213> ORGANISM: Artificial Sequence -continued
<220> FEATURE:
<223> OTHER INFORMATION: Kras (G13D)

<400> SEQUENCE: 17
augacugaau auaaacuugu gguaguugga gcuggugacg uaggcaagag ugccuugacg 60
auacagcuaa uucagaauca uuuugug 87

<210> SEQ ID NO 18
<211> LENGTH: 87
<212> TYPE: RNA
<213> ORGANISM: Artificial Sequence
<220> FEATURE:
<223> OTHER INFORMATION: Kras (G12C)

<400> SEQUENCE: 18
augaccgagu acaagcuggu ggucgugggc gccugcgggg ugggcaagag cgcccucacc 60
auccagcuga uccagaacca cuucguc 87

<210> SEQ ID NO 19
<211> LENGTH: 87
<212> TYPE: RNA
<213> ORGANISM: Artificial Sequence
<220> FEATURE:
<223> OTHER INFORMATION: Kras (G12D)

<400> SEQUENCE: 19
augaccgagu acaagcuggu ggucgugggc gccgacgggg ugggcaagag cgcccucacc 60
auccagcuga uccagaacca cuucguc 87

<210> SEQ ID NO 20
<211> LENGTH: 87
<212> TYPE: RNA
<213> ORGANISM: Artificial Sequence
<220> FEATURE:
<223> OTHER INFORMATION: Kras (G12R)

<400> SEQUENCE: 20
augaccgagu acaagcuggu ggucgugggc gcccgcgggg ugggcaagag cgcccucacc 60
auccagcuga uccagaacca cuucguc 87

<210> SEQ ID NO 21
<211> LENGTH: 87
<212> TYPE: RNA
<213> ORGANISM: Artificial Sequence
<220> FEATURE:
<223> OTHER INFORMATION: Kras (G12V)

<400> SEQUENCE: 21
augaccgagu acaagcuggu ggucgugggc gccgugggggg ucggcaagag cgcccucacc 60
auccagcuga uccagaacca cuucgug 87

<210> SEQ ID NO 22
<211> LENGTH: 87
<212> TYPE: RNA
<213> ORGANISM: Artificial Sequence
<220> FEATURE:
<223> OTHER INFORMATION: Kras (G13D)

<400> SEQUENCE: 22
augaccgagu acaagcuggu ggucgugggc gccggggacg ugggcaagag cgcccucacc 60
auccagcuga uccagaacca cuucguc 87

<210> SEQ ID NO 23
<211> LENGTH: 87
<212> TYPE: RNA
<213> ORGANISM: Artificial Sequence
<220> FEATURE:
<223> OTHER INFORMATION: Kras (G12C)

<400> SEQUENCE: 23
augaccgagu acaagcuggu ggucguuggc gccugcgggg ugggaaaaag cgcucucaca 60
auccagcuua uucaaaacca cuucgua 87

<210> SEQ ID NO 24
<211> LENGTH: 87
<212> TYPE: RNA
<213> ORGANISM: Artificial Sequence
<220> FEATURE:
<223> OTHER INFORMATION: Kras (G12D)

<400> SEQUENCE: 24
augaccgagu acaagcuggu ggucguuggc gccgacgggg ugggaaaaag cgcucucaca 60
auccagcuua uucaaaacca cuucgua 87

<210> SEQ ID NO 25
<211> LENGTH: 87
<212> TYPE: RNA
<213> ORGANISM: Artificial Sequence
<220> FEATURE:
<223> OTHER INFORMATION: Kras (G12R)

<400> SEQUENCE: 25
augaccgagu acaagcuggu ggucguuggc gccagagggg ugggaaaaag cgcucucaca 60
auccagcuua uucaaaacca cuucgua 87

<210> SEQ ID NO 26
<211> LENGTH: 87
<212> TYPE: RNA
<213> ORGANISM: Artificial Sequence
<220> FEATURE:
<223> OTHER INFORMATION: Kras (G12V)

<400> SEQUENCE: 26
augaccgagu acaagcuggu ggucguuggc gccguggggg uaggaaaaag cgcucucaca 60
auccagcuua uucaaaacca cuucgug 87

<210> SEQ ID NO 27
<211> LENGTH: 87
<212> TYPE: RNA
<213> ORGANISM: Artificial Sequence
<220> FEATURE:
<223> OTHER INFORMATION: Kras (G13D)

<400> SEQUENCE: 27
augaccgagu acaagcuggu ggucguuggc gccggggacg ugggaaaaag cgcucucaca 60
auccagcuua uucaaaacca cuucgua 87

<210> SEQ ID NO 28
<211> LENGTH: 87
<212> TYPE: RNA
<213> ORGANISM: Artificial Sequence
<220> FEATURE:
<223> OTHER INFORMATION: Kras (G12C)

<400> SEQUENCE: 28
augaccgagu acaagcuggu ggugugggc gccugcggcg ugggcaagag cgcccugacc 60
auccagcuga uccagaacca cuucgug 87

<210> SEQ ID NO 29
<211> LENGTH: 87
<212> TYPE: RNA
<213> ORGANISM: Artificial Sequence
<220> FEATURE:
<223> OTHER INFORMATION: Kras (G12D)

<400> SEQUENCE: 29
augaccgagu acaagcuggu ggugugggc gccgacggcg ugggcaagag cgcccugacc 60
auccagcuga uccagaacca cuucgug 87

<210> SEQ ID NO 30
<211> LENGTH: 87
<212> TYPE: RNA
<213> ORGANISM: Artificial Sequence
<220> FEATURE:
<223> OTHER INFORMATION: Kras (G12R)

<400> SEQUENCE: 30
augaccgagu acaagcuggu ggugugggc gccagaggcg ugggcaagag cgcccugacc 60
auccagcuga uccagaacca cuucgug 87

<210> SEQ ID NO 31
<211> LENGTH: 87
<212> TYPE: RNA
<213> ORGANISM: Artificial Sequence
<220> FEATURE:
<223> OTHER INFORMATION: Kras (G12V)

<400> SEQUENCE: 31
augaccgagu acaagcuggu ggugugggc gccgugggcg ugggcaagag cgcccugacc 60
auccagcuga uccagaacca cuucgug 87

<210> SEQ ID NO 32
<211> LENGTH: 87
<212> TYPE: RNA
<213> ORGANISM: Artificial Sequence
<220> FEATURE:
<223> OTHER INFORMATION: Kras (G13D)

<400> SEQUENCE: 32
augaccgagu acaagcuggu ggugugggc gccggcgacg ugggcaagag cgcccugacc 60
auccagcuga uccagaacca cuucgug 87

<210> SEQ ID NO 33
<211> LENGTH: 13
<212> TYPE: PRT
<213> ORGANISM: Artificial Sequence
<220> FEATURE:
<223> OTHER INFORMATION: T helper epitope 1

<400> SEQUENCE: 33

Ala Lys Phe Val Ala Ala Trp Thr Leu Lys Ala Ala Ala
1 5 10

<210> SEQ ID NO 34
<211> LENGTH: 39
<212> TYPE: RNA
<213> ORGANISM: Artificial Sequence
<220> FEATURE:
<223> OTHER INFORMATION: T helper epitope 1

<400> SEQUENCE: 34
gccaaguucg uggccgcgug gacccugaag gccgccgcc 39

<210> SEQ ID NO 35
<211> LENGTH: 15
<212> TYPE: PRT
<213> ORGANISM: Artificial Sequence
<220> FEATURE:
<223> OTHER INFORMATION: Linker

<400> SEQUENCE: 35

Gly Gly Gly Gly Ser Gly Gly Gly Gly Ser Gly Gly Gly Gly Ser
1 5 10 15

<210> SEQ ID NO 36
<211> LENGTH: 45
<212> TYPE: RNA
<213> ORGANISM: Artificial Sequence
<220> FEATURE:
<223> OTHER INFORMATION: Linker

<400> SEQUENCE: 36
ggcgggggcg ggagcggcgg gggcggcucc gggggcgggg gcagc 45

<210> SEQ ID NO 37
<211> LENGTH: 45
<212> TYPE: RNA
<213> ORGANISM: Artificial Sequence
<220> FEATURE:
<223> OTHER INFORMATION: Linker

<400> SEQUENCE: 37
ggcggaggcg gaucuggugg cggaggaagu gguggcggcg gaucu 45

<210> SEQ ID NO 38
<211> LENGTH: 45
<212> TYPE: RNA
<213> ORGANISM: Artificial Sequence
<220> FEATURE:
<223> OTHER INFORMATION: Linker

<400> SEQUENCE: 38
ggcggcggag gaucaggcgg ugguggaagc ggagguggug gaucu 45

<210> SEQ ID NO 39
<211> LENGTH: 45
<212> TYPE: RNA
<213> ORGANISM: Artificial Sequence
<220> FEATURE:
<223> OTHER INFORMATION: Linker

<400> SEQUENCE: 39 gguggguggug guucaggcgg cgguggguucu ggcgguggcg gcucu 45

<210> SEQ ID NO 40
<211> LENGTH: 45
<212> TYPE: RNA
<213> ORGANISM: Artificial Sequence
<220> FEATURE:
<223> OTHER INFORMATION: Linker

<400> SEQUENCE: 40
ggcgggggag guagcggcgg gggaggcucc ggugggggag gcucu 45

<210> SEQ ID NO 41
<211> LENGTH: 45
<212> TYPE: RNA
<213> ORGANISM: Artificial Sequence
<220> FEATURE:
<223> OTHER INFORMATION: Linker

<400> SEQUENCE: 41
ggcggcggcg gcagcggcgg cggcggcagc ggcggcggcg gcagc 45

<210> SEQ ID NO 42
<211> LENGTH: 62
<212> TYPE: PRT
<213> ORGANISM: Artificial Sequence
<220> FEATURE:
<223> OTHER INFORMATION: CTLA4(162-223)

<400> SEQUENCE: 42

Phe Leu Leu Trp Ile Leu Ala Ala Val Ser Ser Gly Leu Phe Phe Tyr
1 5 10 15

Ser Phe Leu Leu Thr Ala Val Ser Leu Ser Lys Met Leu Lys Lys Arg
20 25 30

Ser Pro Leu Thr Thr Gly Val Tyr Val Lys Met Pro Pro Thr Glu Pro
35 40 45

Glu Cys Glu Lys Gln Phe Gln Pro Tyr Phe Ile Pro Ile Asn
50 55 60

<210> SEQ ID NO 43
<211> LENGTH: 189
<212> TYPE: RNA
<213> ORGANISM: Artificial Sequence
<220> FEATURE:
<223> OTHER INFORMATION: CTLA4(162-223)

<400> SEQUENCE: 43
uuccuccucu ggauccuugc agcaguuagu ucgggguugu uuuuuuauag cuuucuccuc 60
acagcuguuu cuuugagcaa aaugcuaaag aaaagaagcc cucuuacaac aggggucuau 120
gugaaaaugc ccccaacaga gccagaaugu gaaaagcaau uucagccuua uuuuauuccc 180
aucaauuga 189

<210> SEQ ID NO 44
<211> LENGTH: 189
<212> TYPE: RNA
<213> ORGANISM: Artificial Sequence
<220> FEATURE:
<223> OTHER INFORMATION: CTLA4 (162-223)

<400> SEQUENCE: 44
uuccugcucu ggauccuggc cgccguguccc uccggccugu ucuucuacag cuuccuccug 60
accgcggucu cccugagcaa gaugcucaag aagcgcagcc cccugaccac gggggguguac 120 gugaagaugc cgcccaccga gcccgagugc gagaagcagu uccagcccua cuucaucccg 180
aucaacuga 189

<210> SEQ ID NO 45
<211> LENGTH: 189
<212> TYPE: RNA
<213> ORGANISM: Artificial Sequence
<220> FEATURE:
<223> OTHER INFORMATION: CTLA4 (162-223)

<400> SEQUENCE: 45
uuccuccucu ggauccucgc cgccgucucc uccggccucu ucuucuacuc cuuccuccuc 60
accgccgucu cccucuccaa aaugcucaaa aaacgcuccc cccucaccac cggcgucuac 120
gucaaaaugc cccccaccga acccgaaugc gaaaaacaau uccaacccua cuucaucccc 180
aucaacuaa 189

<210> SEQ ID NO 46
<211> LENGTH: 189
<212> TYPE: RNA
<213> ORGANISM: Artificial Sequence
<220> FEATURE:
<223> OTHER INFORMATION: CTLA4 (162-223)

<400> SEQUENCE: 46
uuccugcucu ggauccuugc cgcugugagc uccggccugu uuuucuacuc uuuucuauua 60
accgcagucu cacugaguaa gauguugaaa aagagaagcc cccucacaac ugggguuuau 120
gugaaaaugc cuccaacgga gccggaaugc gagaagcagu uccaacccua cuuuauuccu 180
auaaacuga 189

<210> SEQ ID NO 47
<211> LENGTH: 189
<212> TYPE: RNA
<213> ORGANISM: Artificial Sequence
<220> FEATURE:
<223> OTHER INFORMATION: CTLA4 (162-223)

<400> SEQUENCE: 47
uuccugcugu ggauccuggc cgccgugagc agcggccugu ucuucuacag cuuccugcug 60
accgccguga gccugagcaa gaugcugaag aagagaagcc cccugaccac cggcguguac 120
gugaagaugc cccccaccga gcccgagugc gagaagcagu uccagcccua cuucaucccc 180
aucaacuga 189

<210> SEQ ID NO 48
<211> LENGTH: 185
<212> TYPE: PRT
<213> ORGANISM: Artificial Sequence
<220> FEATURE:
<223> OTHER INFORMATION: Kras (G12C) construct

<400> SEQUENCE: 48

Met Ala Cys Leu Gly Phe Gln Arg His Lys Ala Gln Leu Asn Leu Ala
1 5 10 15

Thr Arg Thr Trp Pro Cys Thr Leu Leu Phe Phe Leu Leu Phe Ile Pro
20 25 30

Val Phe Cys Ala Gly Gly Gly Gly Ser Gly Gly Gly Gly Ser Gly Gly
35 40 45

Gly Gly Ser Met Thr Glu Tyr Lys Leu Val Val Val Gly Ala Cys Gly
50 55 60

Val Gly Lys Ser Ala Leu Thr Ile Gln Leu Ile Gln Asn His Phe Val
65 70 75 80

Gly Gly Gly Gly Ser Gly Gly Gly Gly Ser Gly Gly Gly Gly Ser Ala
85 90 95

Lys Phe Val Ala Ala Trp Thr Leu Lys Ala Ala Ala Gly Gly Gly Gly
100 105 110

Ser Gly Gly Gly Gly Ser Gly Gly Gly Gly Ser Phe Leu Leu Trp Ile
115 120 125

```
Leu Ala Ala Val Ser Ser Gly Leu Phe Phe Tyr Ser Phe Leu Leu Thr
    130                 135                 140

Ala Val Ser Leu Ser Lys Met Leu Lys Lys Arg Ser Pro Leu Thr Thr
145                 150                 155                 160

Gly Val Tyr Val Lys Met Pro Pro Thr Glu Pro Glu Cys Glu Lys Gln
                165                 170                 175

Phe Gln Pro Tyr Phe Ile Pro Ile Asn
            180                 185


<210> SEQ ID NO 49
<211> LENGTH: 185
<212> TYPE: PRT
<213> ORGANISM: Artificial Sequence
<220> FEATURE:
<223> OTHER INFORMATION: Kras (G12D) construct

<400> SEQUENCE: 49

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Ala Gly Gly Gly Gly Ser Gly Gly Gly Gly Ser Gly Gly
        35                  40                  45

Gly Gly Ser Met Thr Glu Tyr Lys Leu Val Val Val Gly Ala Asp Gly
    50                  55                  60

Val Gly Lys Ser Ala Leu Thr Ile Gln Leu Ile Gln Asn His Phe Val
65                  70                  75                  80

Gly Gly Gly Gly Ser Gly Gly Gly Gly Ser Gly Gly Gly Gly Ser Ala
                85                  90                  95

Lys Phe Val Ala Ala Trp Thr Leu Lys Ala Ala Ala Gly Gly Gly Gly
            100                 105                 110

Ser Gly Gly Gly Gly Ser Gly Gly Gly Gly Ser Phe Leu Leu Trp Ile
        115                 120                 125

Leu Ala Ala Val Ser Ser Gly Leu Phe Phe Tyr Ser Phe Leu Leu Thr
    130                 135                 140

Ala Val Ser Leu Ser Lys Met Leu Lys Lys Arg Ser Pro Leu Thr Thr
145                 150                 155                 160

Gly Val Tyr Val Lys Met Pro Pro Thr Glu Pro Glu Cys Glu Lys Gln
                165                 170                 175

Phe Gln Pro Tyr Phe Ile Pro Ile Asn
            180                 185


<210> SEQ ID NO 50
<211> LENGTH: 185
<212> TYPE: PRT
<213> ORGANISM: Artificial Sequence
<220> FEATURE:
<223> OTHER INFORMATION: Kras (G12R) construct

<400> SEQUENCE: 50

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Ala Gly Gly Gly Gly Ser Gly Gly Gly Gly Ser Gly Gly
        35                  40                  45

Gly Gly Ser Met Thr Glu Tyr Lys Leu Val Val Val Gly Ala Arg Gly
```

```
    50                  55                  60

Val Gly Lys Ser Ala Leu Thr Ile Gln Leu Ile Gln Asn His Phe Val
65                  70                  75                  80

Gly Gly Gly Gly Ser Gly Gly Gly Gly Ser Gly Gly Gly Gly Ser Ala
                85                  90                  95

Lys Phe Val Ala Ala Trp Thr Leu Lys Ala Ala Ala Gly Gly Gly Gly
            100                 105                 110

Ser Gly Gly Gly Gly Ser Gly Gly Gly Gly Ser Phe Leu Leu Trp Ile
        115                 120                 125

Leu Ala Ala Val Ser Ser Gly Leu Phe Phe Tyr Ser Phe Leu Leu Thr
    130                 135                 140

Ala Val Ser Leu Ser Lys Met Leu Lys Lys Arg Ser Pro Leu Thr Thr
145                 150                 155                 160

Gly Val Tyr Val Lys Met Pro Pro Thr Glu Pro Glu Cys Glu Lys Gln
                165                 170                 175

Phe Gln Pro Tyr Phe Ile Pro Ile Asn
            180                 185


<210> SEQ ID NO 51
<211> LENGTH: 185
<212> TYPE: PRT
<213> ORGANISM: Artificial Sequence
<220> FEATURE:
<223> OTHER INFORMATION: Kras (G12V) construct

<400> SEQUENCE: 51

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Ala Gly Gly Gly Gly Ser Gly Gly Gly Gly Ser Gly Gly
        35                  40                  45

Gly Gly Ser Met Thr Glu Tyr Lys Leu Val Val Val Gly Ala Val Gly
    50                  55                  60

Val Gly Lys Ser Ala Leu Thr Ile Gln Leu Ile Gln Asn His Phe Val
65                  70                  75                  80

Gly Gly Gly Gly Ser Gly Gly Gly Gly Ser Gly Gly Gly Gly Ser Ala
                85                  90                  95

Lys Phe Val Ala Ala Trp Thr Leu Lys Ala Ala Ala Gly Gly Gly Gly
            100                 105                 110

Ser Gly Gly Gly Gly Ser Gly Gly Gly Gly Ser Phe Leu Leu Trp Ile
        115                 120                 125

Leu Ala Ala Val Ser Ser Gly Leu Phe Phe Tyr Ser Phe Leu Leu Thr
    130                 135                 140

Ala Val Ser Leu Ser Lys Met Leu Lys Lys Arg Ser Pro Leu Thr Thr
145                 150                 155                 160

Gly Val Tyr Val Lys Met Pro Pro Thr Glu Pro Glu Cys Glu Lys Gln
                165                 170                 175

Phe Gln Pro Tyr Phe Ile Pro Ile Asn
            180                 185


<210> SEQ ID NO 52
<211> LENGTH: 185
<212> TYPE: PRT
<213> ORGANISM: Artificial Sequence
<220> FEATURE:
<223> OTHER INFORMATION: Kras (G13D) construct
```

-continued

<400> SEQUENCE: 52

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Ala Gly Gly Gly Gly Ser Gly Gly Gly Gly Ser Gly Gly
        35                  40                  45

Gly Gly Ser Met Thr Glu Tyr Lys Leu Val Val Val Gly Ala Gly Asp
    50                  55                  60

Val Gly Lys Ser Ala Leu Thr Ile Gln Leu Ile Gln Asn His Phe Val
65                  70                  75                  80

Gly Gly Gly Gly Ser Gly Gly Gly Gly Ser Gly Gly Gly Gly Ser Ala
                85                  90                  95

Lys Phe Val Ala Ala Trp Thr Leu Lys Ala Ala Ala Gly Gly Gly Gly
            100                 105                 110

Ser Gly Gly Gly Gly Ser Gly Gly Gly Gly Ser Phe Leu Leu Trp Ile
        115                 120                 125

Leu Ala Ala Val Ser Ser Gly Leu Phe Phe Tyr Ser Phe Leu Leu Thr
    130                 135                 140

Ala Val Ser Leu Ser Lys Met Leu Lys Lys Arg Ser Pro Leu Thr Thr
145                 150                 155                 160

Gly Val Tyr Val Lys Met Pro Pro Thr Glu Pro Glu Cys Glu Lys Gln
                165                 170                 175

Phe Gln Pro Tyr Phe Ile Pro Ile Asn
            180                 185
```

<210> SEQ ID NO 53
<211> LENGTH: 558
<212> TYPE: RNA
<213> ORGANISM: Artificial Sequence
<220> FEATURE:
<223> OTHER INFORMATION: Kras (G12C) construct

<400> SEQUENCE: 53

```
auggccugcc ugggcuucca gcgccacaag gcccagcuca accuggcgac ccggaccugg      60

cccugcacgc uccuguucuu ccugcuguuc aucccggugu ucugcgcagg cggaggcgga     120

ucugguggcg gaggaagugg uggcggcgga ucuaugaccg aguacaagcu gguggucgug     180

ggcgccugcg gguggggcaa gagcgcccuc accauccagc ugauccagaa ccacuucguc     240

ggcggcggag gaucaggcgg ugguggaagc ggagguggug gaucugccaa guucguggcc     300

gcguggaccc ugaaggccgc cgccggugga ggugguucag gcggcggugg uucuggcggu     360

ggcggcucuu uccugcucug gauccuggcc gccgugagcu ccggccuguu cuucuacagc     420

uuccuccuga ccgcggucuc ccugagcaag augcucaaga agcgcucccc ccugaccacg     480

gggguguacg ugaagaugcc gcccaccgag cccgagugcg agaagcaguu ccagcccuac     540

uucaucccga ucaacuga                                                  558
```

<210> SEQ ID NO 54
<211> LENGTH: 558
<212> TYPE: RNA
<213> ORGANISM: Artificial Sequence
<220> FEATURE:
<223> OTHER INFORMATION: Kras (G12D) construct

<400> SEQUENCE: 54

-continued

```
auggccugcc ugggcuucca gcgccacaag gcccagcuca accuggcgac ccggaccugg     60

cccugcacgc uccuguucuu ccugcuguuc aucccggugu ucugcgcagg cggaggcgga    120

ucugguggcg gaggaagugg uggcggcgga ucuaugaccg aguacaagcu gguggucgug    180

ggcgccgacg gggugggcaa gagcgcccuc accauccagc ugauccagaa ccacuucguc    240

ggcggcggag gaucaggcgg ugguggaagc ggagguggug gaucugccaa guucguggcc    300

gcguggaccc ugaaggccgc cgccggugu ggugguucag gcggcggugg uucuggcggu    360

ggcggcucuu uccugcucug gauccuggcc gccgugagcu ccggccuguu cuucuacagc    420

uuccuccuga ccgcggucuc ccugagcaag augcucaaga agcgcucccc ccugaccacg    480

gggguguacg ugaagaugcc gcccaccgag cccgagugcg agaagcaguu ccagcccuac    540

uucaucccga ucaacuga                                                  558
```

<210> SEQ ID NO 55
<211> LENGTH: 558
<212> TYPE: RNA
<213> ORGANISM: Artificial Sequence
<220> FEATURE:
<223> OTHER INFORMATION: Kras (G12R) construct

<400> SEQUENCE: 55

```
auggccugcc ugggcuucca gcgccacaag gcccagcuca accuggcgac ccggaccugg     60

cccugcacgc uccuguucuu ccugcuguuc aucccggugu ucugcgcagg cggaggcgga    120

ucugguggcg gaggaagugg uggcggcgga ucuaugaccg aguacaagcu gguggucgug    180

ggcgcccgcg gggugggcaa gagcgcccuc accauccagc ugauccagaa ccacuucguc    240

ggcggcggag gaucaggcgg ugguggaagc ggagguggug gaucugccaa guucguggcc    300

gcguggaccc ugaaggccgc cgccggugu ggugguucag gcggcggugg uucuggcggu    360

ggcggcucuu uccugcucug gauccuggcc gccgugagcu ccggccuguu cuucuacagc    420

uuccuccuga ccgcggucuc ccugagcaag augcucaaga agcgcucccc ccugaccacg    480

gggguguacg ugaagaugcc gcccaccgag cccgagugcg agaagcaguu ccagcccuac    540

uucaucccga ucaacuga                                                  558
```

<210> SEQ ID NO 56
<211> LENGTH: 558
<212> TYPE: RNA
<213> ORGANISM: Artificial Sequence
<220> FEATURE:
<223> OTHER INFORMATION: Kras (G12V) construct

<400> SEQUENCE: 56

```
auggccugcc ugggcuucca gcgccacaag gcccagcuca accuggcgac ccggaccugg     60

cccugcacgc uccuguucuu ccugcuguuc aucccggugu ucugcgcagg cggaggcgga    120

ucugguggcg gaggaagugg uggcggcgga ucuaugaccg aguacaagcu gguggucgug    180

ggcgccgugg gggucggcaa gagcgcccuc accauccagc ugauccagaa ccacuucgug    240

ggcggcggag gaucaggcgg ugguggaagc ggagguggug gaucugccaa guucguggcc    300

gcguggaccc ugaaggccgc cgccggugu ggugguucag gcggcggugg uucuggcggu    360

ggcggcucuu uccugcucug gauccuggcc gccgugagcu ccggccuguu cuucuacagc    420

uuccuccuga ccgcggucuc ccugagcaag augcucaaga agcgcucccc ccugaccacg    480

gggguguacg ugaagaugcc gcccaccgag cccgagugcg agaagcaguu ccagcccuac    540

uucaucccga ucaacuga                                                  558
```

<210> SEQ ID NO 57
<211> LENGTH: 558
<212> TYPE: RNA
<213> ORGANISM: Artificial Sequence
<220> FEATURE:
<223> OTHER INFORMATION: Kras (G13D) construct

<400> SEQUENCE: 57
auggccugcc ugggcuucca gcgccacaag gcccagcuca accuggcgac ccggaccugg 60
cccugcacgc uccuguucuu ccugcuguuc aucccggugu ucugcgcagg cggaggcgga 120
ucugguggcg gaggaagugg uggcggcgga ucuaugaccg aguacaagcu gguggucgug 180
ggcgccgggg acgugggcaa gagcgcccuc accauccagc ugauccagaa ccacuucguc 240
ggcggcggag gaucaggcgg ugguggaagc ggagguggug gaucugccaa guucguggcc 300
gcguggaccc ugaaggccgc cgccggugggu gguggguucag gcggcggugg uucuggcggu 360
ggcggcucuu uccugcucug gauccuggcc gccgugagcu ccggccuguu cuucuacagc 420
uuccuccuga ccgcggucuc ccugagcaag augcucaaga agcgcucccc ccugaccacg 480
gggguguacg ugaagaugcc gcccaccgag cccgagugcg agaagcaguu ccagccccuac 540 uucaucccga ucaacuga 558

<210> SEQ ID NO 58
<211> LENGTH: 781
<212> TYPE: RNA
<213> ORGANISM: Artificial Sequence
<220> FEATURE:
<223> OTHER INFORMATION: Kras (G12C) mRNA construct

<400> SEQUENCE: 58
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugggcg gcggaucuau gaccgaguac 180
aagcuggugg ucgugggcgc cugcggggug ggcaagagcg cccucaccau ccagcugauc 240
cagaaccacu ucgucggcgg cggaggauca ggcggugggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaga ucuaaaaaaa 660
aaaaaaaaaa aaaaaaaaaa aaaaaaaaaa aaaaaaaaaa aaaaaaaaaa aaaaaaaugc 720
aucccccccc cccccccccc cccccccccc cccaaaggcu cuuuucagag ccaccagaau 780
u 781

<210> SEQ ID NO 59
<211> LENGTH: 781
<212> TYPE: RNA
<213> ORGANISM: Artificial Sequence
<220> FEATURE:
<223> OTHER INFORMATION: Kras (G12D) mRNA construct

<400> SEQUENCE: 59

-continued

```
gggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga aguggugggcg gcggaucuau gaccgaguac   180

aagcuggugg ucgugggcgc cgacggggug ggcaagagcg cccucaccau ccagcugauc    240

cagaaccacu ucgucggcgg cggaggauca ggcggguggug gaagcggagg ugguggaucu   300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaga ucuaaaaaaa    660

aaaaaaaaaa aaaaaaaaaa aaaaaaaaaa aaaaaaaaaa aaaaaaaaaa aaaaaaaugc    720

aucccccccc cccccccccc cccccccccc cccaaaggcu cuuuucagag ccaccagaau    780

u                                                                    781
```

<210> SEQ ID NO 60
<211> LENGTH: 781
<212> TYPE: RNA
<213> ORGANISM: Artificial Sequence
<220> FEATURE:
<223> OTHER INFORMATION: Kras (G12R) mRNA construct

<400> SEQUENCE: 60

```
gggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga aguggugggcg gcggaucuau gaccgaguac   180

aagcuggugg ucgugggcgc ccgcggggug ggcaagagcg cccucaccau ccagcugauc    240

cagaaccacu ucgucggcgg cggaggauca ggcggguggug gaagcggagg ugguggaucu   300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaga ucuaaaaaaa    660

aaaaaaaaaa aaaaaaaaaa aaaaaaaaaa aaaaaaaaaa aaaaaaaaaa aaaaaaaugc    720

aucccccccc cccccccccc cccccccccc cccaaaggcu cuuuucagag ccaccagaau    780

u                                                                    781
```

<210> SEQ ID NO 61
<211> LENGTH: 781
<212> TYPE: RNA
<213> ORGANISM: Artificial Sequence
<220> FEATURE:
<223> OTHER INFORMATION: Kras (G12V) mRNA construct

<400> SEQUENCE: 61

```
gggagaaagc uuaccauggc cugccugggc uuccagcgcc acaaggccca gcucaaccug     60

gcgacccgga ccuggcccug cacgcuccug uucuuccugc uguucauccc gguguucugc    120
```

```
gcaggcggag gcggaucugg uggcggagga agugguggcg gcggaucuau gaccgaguac    180

aagcuggugg ucgugggcgc cgugggggguc ggcaagagcg cccucaccau ccagcugauc    240

cagaaccacu ucgugggcgg cggaggauca ggcgguggug gaagcggagg ugguggaucu    300

gccaaguucg uggccgcgug gacccugaag gccgccgccg guggugguggg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaga ucuaaaaaaa    660

aaaaaaaaaa aaaaaaaaaa aaaaaaaaaa aaaaaaaaaa aaaaaaaaaa aaaaaaaaugc    720

auccccccccc cccccccccc cccccccccc cccaaaggcu cuuuucagag ccaccagaau    780

u                                                                    781
```

<210> SEQ ID NO 62
<211> LENGTH: 781
<212> TYPE: RNA
<213> ORGANISM: Artificial Sequence
<220> FEATURE:
<223> OTHER INFORMATION: Kras (G13D) mRNA construct

<400> SEQUENCE: 62

```
gggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc cggggacgug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg guggugguggg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaga ucuaaaaaaa    660

aaaaaaaaaa aaaaaaaaaa aaaaaaaaaa aaaaaaaaaa aaaaaaaaaa aaaaaaaaugc    720

auccccccccc cccccccccc cccccccccc cccaaaggcu cuuuucagag ccaccagaau    780

u                                                                    781
```

<210> SEQ ID NO 63
<211> LENGTH: 775
<212> TYPE: RNA
<213> ORGANISM: Artificial Sequence
<220> FEATURE:
<223> OTHER INFORMATION: Kras (G12C) mRNA construct

<400> SEQUENCE: 63

```
gggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180
```

-continued

```
aagcuggugg ucgugggcgc cugcggggug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaaa aaaaaaaaaa    660

aaaaaaaaaa aaaaaaaaaa aaaaaaaaaa aaaaaaaaaa aaaaaaaaaa augcaucccc    720

cccccccccc cccccccccc cccccccaaa ggcucuuuuc agagccacca gaauu         775
```

<210> SEQ ID NO 64
<211> LENGTH: 775
<212> TYPE: RNA
<213> ORGANISM: Artificial Sequence
<220> FEATURE:
<223> OTHER INFORMATION: Kras (G12D) mRNA construct

<400> SEQUENCE: 64

```
gggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc cgacggggug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaaa aaaaaaaaaa    660

aaaaaaaaaa aaaaaaaaaa aaaaaaaaaa aaaaaaaaaa aaaaaaaaaa augcaucccc    720

cccccccccc cccccccccc cccccccaaa ggcucuuuuc agagccacca gaauu         775
```

<210> SEQ ID NO 65
<211> LENGTH: 775
<212> TYPE: RNA
<213> ORGANISM: Artificial Sequence
<220> FEATURE:
<223> OTHER INFORMATION: Kras (G12R) mRNA construct

<400> SEQUENCE: 65

```
gggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc ccgcggggug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420
```

cuguucuucu acagcuuccu ccugaccgcg gucucccuga gcaagaugcu caagaagcgc 480 ucccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa augcaucccc 720
cccccccccc cccccccccc cccccccaaa ggcucuuuuc agagccacca gaauu 775

<210> SEQ ID NO 66
<211> LENGTH: 775
<212> TYPE: RNA
<213> ORGANISM: Artificial Sequence
<220> FEATURE:
<223> OTHER INFORMATION: Kras (G12V) mRNA construct

<400> SEQUENCE: 66
gggagaaagc uuaccauggc cugccugggc uuccagcgcc acaaggccca gcucaaccug 60
gcgacccgga ccuggcccug cacgcuccug uucuuccugc uguucauccc ggguguucugc 120 gcaggcggag gcggaucugg uggcggagga aguggugggcg gcggaucuau gaccgaguac 180
aagcuggugg ucgugggcgc cgugggggguc ggcaagagcg cccucaccau ccagcugauc 240
cagaaccacu ucgugggcgg cggaggauca ggcgguggug gaagcggagg ugguggaucu 300
gccaaguucg uggccgcgug gacccugaag gccgccgccg guggugggugg uucaggcggc 360 ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480 ucccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa augcaucccc 720
cccccccccc cccccccccc cccccccaaa ggcucuuuuc agagccacca gaauu 775

<210> SEQ ID NO 67
<211> LENGTH: 775
<212> TYPE: RNA
<213> ORGANISM: Artificial Sequence
<220> FEATURE:
<223> OTHER INFORMATION: Kras (G13D) mRNA construct

<400> SEQUENCE: 67
gggagaaagc uuaccauggc cugccugggc uuccagcgcc acaaggccca gcucaaccug 60
gcgacccgga ccuggcccug cacgcuccug uucuuccugc uguucauccc ggguguucugc 120 gcaggcggag gcggaucugg uggcggagga aguggugggcg gcggaucuau gaccgaguac 180
aagcuggugg ucgugggcgc cggggacgug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg guggugggugg uucaggcggc 360 ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480 ucccccccuga ccacgggggu guacgugaag augccgccca ccgagcccga gugcgagaag 540
caguuccagc ccuacuucau cccgaucaac ugaggacuag uuauaagacu gacuagcccg 600

-continued

```
augggccucc caacgggccc uccuccccuc cuugcaccga gauuaauaaa aaaaaaaaaa    660

aaaaaaaaaa aaaaaaaaaa aaaaaaaaaa aaaaaaaaaa aaaaaaaaaa augcaucccc    720

cccccccccc cccccccccc cccccccaaa ggcucuuuuc agagccacca gaauu         775
```

<210> SEQ ID NO 68
<211> LENGTH: 775
<212> TYPE: RNA
<213> ORGANISM: Artificial Sequence
<220> FEATURE:
<223> OTHER INFORMATION: Kras (G12C) mRNA construct

<400> SEQUENCE: 68

```
aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga aguggguggcg gcggaucuau gaccgaguac    180

aagcuggugg ucgugggcgc cugcggggug ggcaagagcg cccucaccau ccagcugauc    240

cagaaccacu ucgucggcgg cggaggauca ggcggguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaaa aaaaaaaaaa    660

aaaaaaaaaa aaaaaaaaaa aaaaaaaaaa aaaaaaaaaa aaaaaaaaaa augcaucccc    720

cccccccccc cccccccccc cccccccaaa ggcucuuuuc agagccacca gaauu         775
```

<210> SEQ ID NO 69
<211> LENGTH: 775
<212> TYPE: RNA
<213> ORGANISM: Artificial Sequence
<220> FEATURE:
<223> OTHER INFORMATION: Kras (G12D) mRNA construct

<400> SEQUENCE: 69

```
aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc cgacggggug ggcaagagcg cccucaccau ccagcugauc    240

cagaaccacu ucgucggcgg cggaggauca ggcggguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaaa aaaaaaaaaa    660

aaaaaaaaaa aaaaaaaaaa aaaaaaaaaa aaaaaaaaaa aaaaaaaaaa augcaucccc    720

cccccccccc cccccccccc cccccccaaa ggcucuuuuc agagccacca gaauu         775
```

-continued

<210> SEQ ID NO 70
<211> LENGTH: 775
<212> TYPE: RNA
<213> ORGANISM: Artificial Sequence
<220> FEATURE:
<223> OTHER INFORMATION: Kras (G12R) mRNA construct

<400> SEQUENCE: 70
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggggcg gcggaucuau gaccgaguac 180
aagcuggugg ucgugggcgc ccgcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa augcaucccc 720
cccccccccc cccccccccc ccccccccaaa ggcucuuuuc agagccacca gaauu 775

<210> SEQ ID NO 71
<211> LENGTH: 775
<212> TYPE: RNA
<213> ORGANISM: Artificial Sequence
<220> FEATURE:
<223> OTHER INFORMATION: Kras (G12V) mRNA construct

<400> SEQUENCE: 71
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggggcg gcggaucuau gaccgaguac 180
aagcuggugg ucgugggcgc cgugggggguc ggcaagagcg cccucaccau ccagcugauc 240
cagaaccacu ucgugggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa augcaucccc 720
cccccccccc cccccccccc ccccccccaaa ggcucuuuuc agagccacca gaauu 775

<210> SEQ ID NO 72
<211> LENGTH: 775
<212> TYPE: RNA
<213> ORGANISM: Artificial Sequence
<220> FEATURE:
<223> OTHER INFORMATION: Kras (G13D) mRNA construct

<400> SEQUENCE: 72
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggguggcg gcggaucuau gaccgaguac 180
aagcuggugg ucgugggcgc cggggacgug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg guggugggugg uucaggcggc 360 ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa augcaucccc 720
cccccccccc cccccccccc ccccccaaa ggcucuuuuc agagccacca gaauu 775

<210> SEQ ID NO 73
<211> LENGTH: 771
<212> TYPE: RNA
<213> ORGANISM: Artificial Sequence
<220> FEATURE:
<223> OTHER INFORMATION: Kras (G12C) mRNA construct

<400> SEQUENCE: 73
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggguggcg gcggaucuau gaccgaguac 180
aagcuggugg ucgugggcgc cugcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg guggugggugg uucaggcggc 360 ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 74
<211> LENGTH: 771
<212> TYPE: RNA
<213> ORGANISM: Artificial Sequence
<220> FEATURE:
<223> OTHER INFORMATION: Kras (G12D) mRNA construct

<400> SEQUENCE: 74
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggguggcg gcggaucuau gaccgaguac 180
aagcuggugg ucgugggcgc cgacggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg guggugugg uucaggcggc 360 ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 75
<211> LENGTH: 771
<212> TYPE: RNA
<213> ORGANISM: Artificial Sequence
<220> FEATURE:
<223> OTHER INFORMATION: Kras (G12R) mRNA construct

<400> SEQUENCE: 75
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugg cg gcggaucuau gaccgaguac 180
aagcuggugg ucgugggcgc ccgcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg guggugugg uucaggcggc 360 ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 76
<211> LENGTH: 771
<212> TYPE: RNA
<213> ORGANISM: Artificial Sequence
<220> FEATURE:
<223> OTHER INFORMATION: Kras (G12V) mRNA construct

<400> SEQUENCE: 76
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugg cg gcggaucuau gaccgaguac 180
aagcuggugg ucgugggcgc cgugggggu c ggcaagagcg cccucaccau ccagcugauc 240
cagaaccacu ucgugggcgg cggaggauca ggcgguggug gaagcggagg ugguggaucu 300
gccaaguucg uggccgcgug gacccugaag gccgccgccg guggugugg uucaggcggc 360

-continued ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 77
<211> LENGTH: 771
<212> TYPE: RNA
<213> ORGANISM: Artificial Sequence
<220> FEATURE:
<223> OTHER INFORMATION: Kras (G13D) mRNA construct

<400> SEQUENCE: 77
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga agugguggcg gcggaucuau gaccgaguac 180
aagcuggugg ucgugggcgc cggggacgug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 78
<211> LENGTH: 771
<212> TYPE: RNA
<213> ORGANISM: Artificial Sequence
<220> FEATURE:
<223> OTHER INFORMATION: Kras (G12C) mRNA construct

<400> SEQUENCE: 78
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga agugguggcg gcggaucuau gaccgaguac 180
aagcuggugg ucgugggcgc cugcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 79
<211> LENGTH: 771
<212> TYPE: RNA
<213> ORGANISM: Artificial Sequence
<220> FEATURE:
<223> OTHER INFORMATION: Kras (G12D) mRNA construct

<400> SEQUENCE: 79
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugggcg gcggaucuau gaccgaguac 180
aagcuggugg ucgugggcgc cgacggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360 gguggguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 80
<211> LENGTH: 771
<212> TYPE: RNA
<213> ORGANISM: Artificial Sequence
<220> FEATURE:
<223> OTHER INFORMATION: Kras (G12R) mRNA construct

<400> SEQUENCE: 80
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugggcg gcggaucuau gaccgaguac 180
aagcuggugg ucgugggcgc ccgcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360 gguggguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 81
<211> LENGTH: 771
<212> TYPE: RNA
<213> ORGANISM: Artificial Sequence
<220> FEATURE:
<223> OTHER INFORMATION: Kras (G12V) mRNA construct

<400> SEQUENCE: 81
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggguggcg gcggaucuau gaccgaguac 180
aagcuggugg ucgugggcgc cguggggguc ggcaagagcg cccucaccau ccagcugauc 240
cagaaccacu ucgugggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 82
<211> LENGTH: 771
<212> TYPE: RNA
<213> ORGANISM: Artificial Sequence
<220> FEATURE:
<223> OTHER INFORMATION: Kras (G13D) mRNA construct

<400> SEQUENCE: 82
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga agugguggcg gcggaucuau gaccgaguac 180
aagcuggugg ucgugggcgc cggggacgug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaaucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 83
<211> LENGTH: 771
<212> TYPE: RNA
<213> ORGANISM: Artificial Sequence
<220> FEATURE:
<223> OTHER INFORMATION: Kras (G12C) mRNA construct

<400> SEQUENCE: 83
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugggcg gcggaucuau gaccgaguac 180
aagcuggugg ucgugggcgc cugcggggug ggcaagagcg cccucaccau ccagcugauc 240
cagaaccacu ucgucggcgg cggaggauca ggcggguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 84
<211> LENGTH: 771
<212> TYPE: RNA
<213> ORGANISM: Artificial Sequence
<220> FEATURE:
<223> OTHER INFORMATION: Kras (G12D) mRNA construct

<400> SEQUENCE: 84
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugggcg gcggaucuau gaccgaguac 180
aagcuggugg ucgugggcgc cgacggggug ggcaagagcg cccucaccau ccagcugauc 240
cagaaccacu ucgucggcgg cggaggauca ggcggguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 85
<211> LENGTH: 771
<212> TYPE: RNA
<213> ORGANISM: Artificial Sequence
<220> FEATURE:
<223> OTHER INFORMATION: Kras (G12R) mRNA construct

<400> SEQUENCE: 85
gggagaaagc uuaccauggc cugccugggc uuccagcgcc acaaggccca gcucaaccug 60
gcgacccgga ccuggcccug cacgcuccug uucuuccugc uguucauccc gguguucugc 120

```
gcaggcggag gcggaucugg uggcggagga aguggguggcg gcggaucuau gaccgaguac    180

aagcuggugg ucgugggcgc ccgcggggug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gagaucucaa aggcucuuuu    660

cagagccacc aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa a             771
```

<210> SEQ ID NO 86
<211> LENGTH: 771
<212> TYPE: RNA
<213> ORGANISM: Artificial Sequence
<220> FEATURE:
<223> OTHER INFORMATION: Kras (G12V) mRNA construct

<400> SEQUENCE: 86

```
gggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga aguggguggcg gcggaucuau gaccgaguac    180

aagcuggugg ucgugggcgc cguggggguc ggcaagagcg cccucaccau ccagcugauc    240

cagaaccacu ucgugggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gagaucucaa aggcucuuuu    660

cagagccacc aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa a             771
```

<210> SEQ ID NO 87
<211> LENGTH: 771
<212> TYPE: RNA
<213> ORGANISM: Artificial Sequence
<220> FEATURE:
<223> OTHER INFORMATION: Kras (G13D) mRNA construct

<400> SEQUENCE: 87

```
gggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga aguggguggcg gcggaucuau gaccgaguac    180

aagcuggugg ucgugggcgc cggggacgug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360
```

ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 88
<211> LENGTH: 771
<212> TYPE: RNA
<213> ORGANISM: Artificial Sequence
<220> FEATURE:
<223> OTHER INFORMATION: Kras (G12C) mRNA construct

<400> SEQUENCE: 88
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggcggcg gcggaucuau gaccgaguac 180
aagcuggugg ucgugggcgc cugcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 89
<211> LENGTH: 771
<212> TYPE: RNA
<213> ORGANISM: Artificial Sequence
<220> FEATURE:
<223> OTHER INFORMATION: Kras (G12D) mRNA construct

<400> SEQUENCE: 89
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggcggcg gcggaucuau gaccgaguac 180
aagcuggugg ucgugggcgc cgacggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540

-continued caguuccagc ccuacuucau cccgaucaac ugaggacuag uuauaagacu gacuagcccg 600
augggccucc caacgggccc uccuccccuc cuugcaccga gagaucucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 90
<211> LENGTH: 771
<212> TYPE: RNA
<213> ORGANISM: Artificial Sequence
<220> FEATURE:
<223> OTHER INFORMATION: Kras (G12R) mRNA construct

<400> SEQUENCE: 90
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugcg gcggaucuau gaccgaguac 180
aagcuggugg ucgugggcgc ccgcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 91
<211> LENGTH: 771
<212> TYPE: RNA
<213> ORGANISM: Artificial Sequence
<220> FEATURE:
<223> OTHER INFORMATION: Kras (G12V) mRNA construct

<400> SEQUENCE: 91
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugcg gcggaucuau gaccgaguac 180
aagcuggugg ucgugggcgc cgugggggugc ggcaagagcg cccucaccau ccagcugauc 240
cagaaccacu ucgugggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

-continued

<210> SEQ ID NO 92
<211> LENGTH: 771
<212> TYPE: RNA
<213> ORGANISM: Artificial Sequence
<220> FEATURE:
<223> OTHER INFORMATION: Kras (G13D) mRNA construct

<400> SEQUENCE: 92
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggguggcg gcggaucuau gaccgaguac 180
aagcuggugg ucgugggcgc cggggacgug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg guggugugg uucaggcggc 360 ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucucaa aggcucuuuu 660
cagagccacc aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa a 771

<210> SEQ ID NO 93
<211> LENGTH: 747
<212> TYPE: RNA
<213> ORGANISM: Artificial Sequence
<220> FEATURE:
<223> OTHER INFORMATION: Kras (G12C) mRNA construct

<400> SEQUENCE: 93
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga agugguggcg gcggaucuau gaccgaguac 180
aagcuggugg ucgugggcgc cugcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg guggugugg uucaggcggc 360 ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 94
<211> LENGTH: 747
<212> TYPE: RNA
<213> ORGANISM: Artificial Sequence
<220> FEATURE:

-continued

<223> OTHER INFORMATION: Kras (G12D) mRNA construct

<400> SEQUENCE: 94
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugggcg gcggaucuau gaccgaguac 180
aagcuggugg ucgugggcgc cgacggggug ggcaagagcg cccucaccau ccagcugauc 240
cagaaccacu ucgucggcgg cggaggauca ggcggugggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 95
<211> LENGTH: 747
<212> TYPE: RNA
<213> ORGANISM: Artificial Sequence
<220> FEATURE:
<223> OTHER INFORMATION: Kras (G12R) mRNA construct

<400> SEQUENCE: 95
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugggcg gcggaucuau gaccgaguac 180
aagcuggugg ucgugggcgc ccgcggggug ggcaagagcg cccucaccau ccagcugauc 240
cagaaccacu ucgucggcgg cggaggauca ggcggugggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 96
<211> LENGTH: 747
<212> TYPE: RNA
<213> ORGANISM: Artificial Sequence
<220> FEATURE:
<223> OTHER INFORMATION: Kras (G12V) mRNA construct

<400> SEQUENCE: 96
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga agugguggcg gcggaucuau gaccgaguac 180
aagcuggugg ucgugggcgc cguggggguc ggcaagagcg cccucaccau ccagcugauc 240
cagaaccacu ucgugggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 97
<211> LENGTH: 747
<212> TYPE: RNA
<213> ORGANISM: Artificial Sequence
<220> FEATURE:
<223> OTHER INFORMATION: Kras (G13D) mRNA construct

<400> SEQUENCE: 97
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga agugguggcg gcggaucuau gaccgaguac 180
aagcuggugg ucgugggcgc cggggacgug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 98
<211> LENGTH: 747
<212> TYPE: RNA
<213> ORGANISM: Artificial Sequence
<220> FEATURE:
<223> OTHER INFORMATION: Kras (G12C) mRNA construct

<400> SEQUENCE: 98
aggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga agugguggcg gcggaucuau gaccgaguac 180
aagcuggugg ucgugggcgc cugcggggug ggcaagagcg cccucaccau ccagcugauc 240
cagaaccacu ucgucggcgg cggaggauca ggcgguggug gaagcggagg ugguggaucu 300

-continued gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480 ucccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 99
<211> LENGTH: 747
<212> TYPE: RNA
<213> ORGANISM: Artificial Sequence
<220> FEATURE:
<223> OTHER INFORMATION: Kras (G12D) mRNA construct

<400> SEQUENCE: 99
aggagaaagc uuaccauggc cugccugggc uuccagcgcc acaaggccca gcucaaccug 60
gcgacccgga ccuggcccug cacgcuccug uucuuccugc uguucauccc ggguguucugc 120 gcaggcggag gcggaucugg uggcggagga aguggugggcg gcggaucuau gaccgaguac 180
aagcuggugg ucgugggcgc cgacggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480 ucccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gauuaauaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 100
<211> LENGTH: 747
<212> TYPE: RNA
<213> ORGANISM: Artificial Sequence
<220> FEATURE:
<223> OTHER INFORMATION: Kras (G12R) mRNA construct

<400> SEQUENCE: 100
aggagaaagc uuaccauggc cugccugggc uuccagcgcc acaaggccca gcucaaccug 60
gcgacccgga ccuggcccug cacgcuccug uucuuccugc uguucauccc ggguguucugc 120 gcaggcggag gcggaucugg uggcggagga aguggugggcg gcggaucuau gaccgaguac 180
aagcuggugg ucgugggcgc ccgcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480 ucccccccuga ccacgggggu guacgugaag augccgccca ccgagcccga gugcgagaag 540

```
caguuccagc ccuacuucau cccgaucaac ugaggacuag uuauaagacu gacuagcccg    600

augggccucc caacgggccc uccuccccuc cuugcaccga gauuaauaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaa                                        747


<210> SEQ ID NO 101
<211> LENGTH: 747
<212> TYPE: RNA
<213> ORGANISM: Artificial Sequence
<220> FEATURE:
<223> OTHER INFORMATION: Kras (G12V) mRNA construct

<400> SEQUENCE: 101

aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc cgugggggguc ggcaagagcg cccucaccau ccagcugauc    240

cagaaccacu ucgugggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaa                                        747


<210> SEQ ID NO 102
<211> LENGTH: 747
<212> TYPE: RNA
<213> ORGANISM: Artificial Sequence
<220> FEATURE:
<223> OTHER INFORMATION: Kras (G13D) mRNA construct

<400> SEQUENCE: 102

aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc cggggacgug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gauuaauaaa aaaaaaaaaa    660

aaaaaaaaaa aaaaaaaaaa aaaaaaaaaa aaaaaaaaaa aaaaaaaaaa aaaaaaaaaa    720
```

aaaaaaaaaa aaaaaaaaaa aaaaaaa 747

<210> SEQ ID NO 103
<211> LENGTH: 747
<212> TYPE: RNA
<213> ORGANISM: Artificial Sequence
<220> FEATURE:
<223> OTHER INFORMATION: Kras (G12C) mRNA construct

<400> SEQUENCE: 103
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugcg gcggaucuau gaccgaguac 180
aagcuggugg ucgugggcgc cugcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucuaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 104
<211> LENGTH: 747
<212> TYPE: RNA
<213> ORGANISM: Artificial Sequence
<220> FEATURE:
<223> OTHER INFORMATION: Kras (G12D) mRNA construct

<400> SEQUENCE: 104
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggugcg gcggaucuau gaccgaguac 180
aagcuggugg ucgugggcgc cgacggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360
ggugguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucuaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 105
<211> LENGTH: 747
<212> TYPE: RNA
<213> ORGANISM: Artificial Sequence
<220> FEATURE:
<223> OTHER INFORMATION: Kras (G12R) mRNA construct

<400> SEQUENCE: 105
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga aguggguggcg gcggaucuau gaccgaguac 180
aagcuggugg ucgugggcgc ccgcggggug ggcaagagcg cccucaccau ccagcugauc 240
cagaaccacu ucgucggcgg cggaggauca ggcgguggug gaagcggagg ugguggaucu 300
gccaaguucg uggccgcgug gacccugaag gccgccgccg gugguggugg uucaggcggc 360 gguggguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucuaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 106
<211> LENGTH: 747
<212> TYPE: RNA
<213> ORGANISM: Artificial Sequence
<220> FEATURE:
<223> OTHER INFORMATION: Kras (G12V) mRNA construct

<400> SEQUENCE: 106
gggagaaagc uuaccauggc cugccugggc uuccagcgcc acaaggccca gcucaaccug 60
gcgacccgga ccuggcccug cacgcuccug uucuuccugc uguucauccc gguguucugc 120
gcaggcggag gcggaucugg uggcggagga agugguggcg gcggaucuau gaccgaguac 180
aagcuggugg ucgugggcgc cgugggggguc ggcaagagcg cccucaccau ccagcugauc 240
cagaaccacu ucgugggcgg cggaggauca ggcgguggug gaagcggagg ugguggaucu 300
gccaaguucg uggccgcgug gacccugaag gccgccgccg gugguggugg uucaggcggc 360 gguggguucug gcgguggcgg cucuuuccug cucuggaucc uggccgccgu gagcuccggc 420
cuguucuucu acagcuuccu ccugaccgcg gucucccuga gcaagaugcu caagaagcgc 480
uccccccuga ccacgggggu guacgugaag augccgccca ccgagcccga gugcgagaag 540
caguuccagc ccuacuucau cccgaucaac ugaggacuag uuauaagacu gacuagcccg 600
augggccucc caacgggccc uccuccccuc cuugcaccga gagaucuaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaa 747

<210> SEQ ID NO 107
<211> LENGTH: 747
<212> TYPE: RNA
<213> ORGANISM: Artificial Sequence
<220> FEATURE:
<223> OTHER INFORMATION: Kras (G13D) mRNA construct

<400> SEQUENCE: 107
gggagaaagc uuaccauggc cugccugggc uuccagcgcc acaaggccca gcucaaccug 60

-continued

```
gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc cggggacgug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gagaucuaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaa                                        747
```

<210> SEQ ID NO 108
<211> LENGTH: 747
<212> TYPE: RNA
<213> ORGANISM: Artificial Sequence
<220> FEATURE:
<223> OTHER INFORMATION: Kras (G12C) mRNA construct

<400> SEQUENCE: 108

```
aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc cugcggggug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gagaucuaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaa                                        747
```

<210> SEQ ID NO 109
<211> LENGTH: 747
<212> TYPE: RNA
<213> ORGANISM: Artificial Sequence
<220> FEATURE:
<223> OTHER INFORMATION: Kras (G12D) mRNA construct

<400> SEQUENCE: 109

```
aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga agugguggcg gcggaucuau gaccgaguac    180

aagcuggugg ucgugggcgc cgacggggug ggcaagagcg cccucaccau ccagcugauc    240

cagaaccacu ucgucggcgg cggaggauca ggcgguggug gaagcggagg ugguggaucu    300
```

-continued

```
gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gagaucuaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaa                                        747
```

```
<210> SEQ ID NO 110
<211> LENGTH: 747
<212> TYPE: RNA
<213> ORGANISM: Artificial Sequence
<220> FEATURE:
<223> OTHER INFORMATION: Kras (G12R) mRNA construct

<400> SEQUENCE: 110

aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga aguggugggcg gcggaucuau gaccgaguac    180

aagcuggugg ucgugggcgc ccgcggggug ggcaagagcg cccucaccau ccagcugauc    240

cagaaccacu ucgucggcgg cggaggauca ggcggguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gagaucuaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaa                                        747
```

```
<210> SEQ ID NO 111
<211> LENGTH: 747
<212> TYPE: RNA
<213> ORGANISM: Artificial Sequence
<220> FEATURE:
<223> OTHER INFORMATION: Kras (G12V) mRNA construct

<400> SEQUENCE: 111

aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga aguggugggcg gcggaucuau gaccgaguac    180

aagcuggugg ucgugggcgc cgugggggguc ggcaagagcg cccucaccau ccagcugauc    240

cagaaccacu ucgugggcgg cggaggauca ggcggguggug gaagcggagg ugguggaucu    300

gccaaguucg uggccgcgug gacccugaag gccgccgccg gugguggugg uucaggcggc    360

gguggguucug gcgguggcgg cucuuuccug cucuggaucc uggccgccgu gagcuccggc    420

cuguucuucu acagcuuccu ccugaccgcg gucucccuga gcaagaugcu caagaagcgc    480
```

-continued

```
uccccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gagaucuaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaa                                         747


<210> SEQ ID NO 112
<211> LENGTH: 747
<212> TYPE: RNA
<213> ORGANISM: Artificial Sequence
<220> FEATURE:
<223> OTHER INFORMATION: Kras (G13D) mRNA construct

<400> SEQUENCE: 112

aggagaaagc uuaccauggc cugccugggc uuccagcgcc acaaggccca gcucaaccug     60

gcgacccgga ccuggcccug cacgcuccug uucuuccugc uguucauccc gguguucugc    120

gcaggcggag gcggaucugg uggcggagga aguggcggcg gcggaucuau gaccgaguac    180

aagcuggugg ucgugggcgc cggggacgug ggcaagagcg cccucaccau ccagcugauc    240

cagaaccacu ucgucggcgg cggaggauca ggcgguggug gaagcggagg ugguggaucu    300

gccaaguucg uggccgcgug gacccugaag gccgccgccg gugguggugg uucaggcggc    360

ggugguucug gcgguggcgg cucuuuccug cucuggaucc uggccgccgu gagcuccggc    420

cuguucuucu acagcuuccu ccugaccgcg gucucccuga gcaagaugcu caagaagcgc    480

ucccccuga ccacgggggu guacgugaag augccgccca ccgagcccga gugcgagaag    540

caguuccagc ccuacuucau cccgaucaac ugaggacuag uuauaagacu gacuagcccg    600

augggccucc caacgggccc uccuccccuc cuugcaccga gagaucuaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaa                                         747
```

KRAS VARIANT MRNA MOLECULES

The present application is a national phase application under 35 U.S.C. § 371 of International Application No. PCT/US2019/064976, filed Dec. 6, 2019, which claims the priority benefit of U.S. Provisional Application No. 62/788,285, filed Jan. 4, 2019, and U.S. Provisional Application No. 62/779,858, filed Dec. 14, 2018, the entire contents of each of which are hereby incorporated by reference.

The present application is a national phase application under 35 U.S.C. § 371 of International Application No. PCT/US2019/064976, filed Dec. 6, 2019, which claims the priority benefit of U.S. Provisional Application No. 62/788,285, filed Jan. 4, 2019, and U.S. Provisional Application No. 62/779,858, filed Dec. 14, 2018, the entire contents of each of which are hereby incorporated by reference.

RAS genes (so named for their role in forming rat sarcomas) were the first oncogenes identified in human cancer cells. The three RAS genes encode 188-189 amino acid proteins that share 82%-90% amino acid sequence identity and share near-identical structural and biochemical properties. The RAS (rat sarcoma) protein family members are low-molecular-weight GTP-binding proteins that play a role in regulating cell differentiation, proliferation, and survival. There are three main members of the RAS family: HRAS, NRAS, and KRAS, which comprise the most frequently mutated oncogene family in human cancer, with mutations in RAS being found in approximately 25-30% of human cancers (E Santos, *Genes Cancer* 2011; 2: 344-358).

RAS mutation frequencies are highest in three of the leading causes of cancer deaths in the United States (lung, colorectal, and pancreatic cancer), resulting in intense efforts to develop anti-RAS therapies (Wang et al., *J. Med. Chem.* 2013; 56: 5219-5230; Waters and Der, *Cold Spring Harb Perspect Med.* 2018; 8: a031435; and Stephen et al., *Cancer Cell.* 2014; 25:272-81, doi: 10.1016/j.ccr.2014.02.017).

KRAS is the most frequently mutated RAS isoform, and was shown to be mutated in up to 90% of pancreatic adenocarcinomas, 45% of colorectal cancers, and 25-35% of lung adenocarcinomas (Zeitouni D, et al., *Cancers* (Basel) 2016; 8:45; Tan C and X Du, *World J. Gastroent.* 2012; 18: 5175-5189; and Kempf E, et al., *Eur. Resp. Rev.* 2016; 25: 71-76). KRAS mutations have been observed in pancreatic, colon, small intestine, biliary and lung cancer tumors, and NRAS mutations have been observed in hematopoietic and skin cancers (Hunter J D, et al., *Mol. Cancer Research* 13: 1325 (2015)). RAS mutations were observed in tumors of adrenal gland, biliary tract, bone, breast, cervix, endometrium, lymphoid, kidney, large intestine, liver, lung, esophagus, ovary, pancreas, prostate, salivary gland, skin, small intestine, stomach and testis, and KRAS is the most frequently mutated isoform of RAS, present in 22% of tumors analysed in the COSMIC dataset (Prior I A, et al., *Cancer Research* 71: 2457 (2012)).

However, despite more than three decades of intense effort, effective KRAS inhibitors have yet to reach cancer patients, and KRAS-driven cancers are among the most difficult to treat and are sometimes excluded from therapies. The Ras proteins have been termed "undruggable," based primarily on the inability to identify an effective chemical inhibitor.

Thus, there remains an unmet medical need for an effective anti-cancer therapy for patients having tumors with KRAS mutations.

The present invention provides an mRNA molecule comprising mRNA sequence encoding an amino acid sequence comprising a CTLA4 signal peptide, a KRAS variant peptide, a PADRE-derived T helper epitope sequence, and a CTLA4 transmembrane domain, or portion thereof. In a preferred embodiment, the KRAS variant peptide comprises 29 contiguous amino acid residues of KRAS variant peptide sequence In one preferred embodiment, the mRNA molecule of the present invention is formulated as a lipid nanoparticle, e.g., in a pharmaceutical composition. In another embodiment, the lipid nanoparticle, e.g., in a pharmaceutical composition, comprises 1, 2, 3, 4 or 5 mRNA molecules which are formulated as a lipid nanoparticle, wherein each individual mRNA molecule encodes a different KRAS variant peptide. In another preferred embodiment, the lipid nanoparticle, e.g., in a pharmaceutical composition, comprises 5 mRNA molecules, wherein each individual mRNA molecule encodes a different KRAS variant peptide. In another preferred embodiment, the lipid nanoparticle, e.g., in a pharmaceutical composition, comprises 4 mRNA molecules, wherein each individual mRNA molecule encodes a different KRAS variant peptide. In another preferred embodiment, the lipid nanoparticle, e.g., in a pharmaceutical composition, comprises 3 mRNA molecules, wherein each individual mRNA molecule encodes a different KRAS variant peptide. In another preferred embodiment, the lipid nanoparticle, e.g., in a pharmaceutical composition, comprises 2 mRNA molecules, wherein each individual mRNA molecule encodes a different KRAS variant peptide. In another embodiment, the lipid nanoparticle, e.g., in a pharmaceutical composition, comprises 1 mRNA molecules.

In another preferred embodiment, one or more individual mRNA molecules, each encoding a different KRAS variant peptide, is/are mixed prior to formulation as a lipid nanoparticle. In another preferred embodiment, 1, 2, 3, 4, or 5, individual mRNA molecules, each encoding a particular KRAS variant peptide, is/are mixed prior to formulation as a lipid nanoparticle. In another preferred embodiment, 5 individual mRNA molecules, each encoding a different KRAS variant peptide are mixed together prior to formulation as a lipid nanoparticle.

In one preferred embodiment, the lipid nanoparticle formulation comprises one or more mRNA molecules of the invention, a phosphocholine (e.g., distearoylphosphocholine (DSPC), or 1,2-distearoyl-sn-glycero-3-phosphocholine), a pegylated lipid (e.g., 2-mPEG2000-n,n ditetradecylacetamide), a sterol (e.g., cholesterol) and a cationic lipid derived from Formula (LNP-III) herein (e.g, the lipid of LNP III-3 in Table 4 herein). In another embodiment, the lipid nanoparticle comprises one or more mRNA molecules of the invention, 1,2-distearoyl-sn-glycero-3-phosphocholine (DSPC), 2-mPEG2000-n,n ditetradecylacetamide, cholesterol and the lipid of LNP III-3 in Table 4 herein.

In another preferred embodiment, the KRAS variant peptide comprises the KRAS G12C variant amino acid residue, the KRAS G12D variant amino acid residue, the KRAS G12V variant amino acid residue, the KRAS G12R variant amino acid residue, or the KRAS G13D variant amino acid residue.

In another preferred embodiment, the mRNA molecule further comprises a 3'-UTR sequence. In another embodiment, the mRNA molecule further comprises a 5'-UTR sequence and a 3'-UTR sequence.

In another preferred embodiment, the mRNA does not contain sequence encoding any other functional elements. In another preferred embodiment, the mRNA does not encode a stimulator of interferon genes (STING) peptide or polypeptide.

In another preferred embodiment, the KRAS variant peptide comprises the amino acid sequence of SEQ ID NO: 8, SEQ ID NO: 9, SEQ ID NO: 10, SEQ ID NO: 11 or SEQ ID NO: 12 (Table 1), which amino acid sequences can be preferably encoded, respectively, by nucleic acids set forth in columns three and four of Table 1.

TABLE 1

| KRAS variant (neo-epitope) | SEQ ID NO: (amino acid) | SEQ ID NO: (wt nucleic acid) | SEQ ID NO: (optimized nucleic acid) |
|---|---|---|---|
| G12C | 8 | 13 | 18 or 23 or 28 |
| G12D | 9 | 14 | 19 or 24 or 29 |
| G12R | 10 | 15 | 20 or 25 or 30 |
| G12V | 11 | 16 | 21 or 26 or 31 |
| G13D | 12 | 17 | 22 or 27 or 32 |

In another preferred embodiment, the mRNA molecule is an mRNA molecule set forth in a sequence identifier in Table 2.

TABLE 2

| KRAS variant (neo-epitope) | KRAS Peptide Amino Acid SEQ ID NO: | Full Encoded Amino Acid SEQ ID NO: | mRNA coding sequence SEQ ID NO: | One preferred embodiment of mRNA construct SEQ ID NOs: |
|---|---|---|---|---|
| G12C | 8 | 48 | 58, 63, 68, 73, 78, 83, 88, 93, 98, 103 or 108 | 63, 58 or 68 |
| G12D | 9 | 49 | 59, 64, 69, 74, 79, 84, 89, 94, 99, 104 or 109 | 64, 59 or 69 |
| G12R | 10 | 50 | 60, 65, 70, 75, 80, 85, 90, 95, 100, 105 or 110 | 65, 60 or 70 |
| G12V | 11 | 51 | 61, 66, 71, 76, 81, 86, 91, 96, 101, 106 or 111 | 66, 61 or 71 |
| G13D | 12 | 52 | 62, 67, 72, 77, 82, 87, 92, 97, 102, 107 or 112 | 67, 62 or 72 |

In another preferred embodiment, the mRNA molecule is an mRNA molecule set forth in SEQ ID NO: 63, SEQ ID NO: 64, SEQ ID NO: 65, SEQ ID NO: 66 or SEQ ID NO: 67 (Table 2).

In another preferred embodiment, the mRNA molecule is an mRNA molecule set forth in SEQ ID NO: 58, SEQ ID NO: 59, SEQ ID NO: 60, SEQ ID NO: 61 or SEQ ID NO: 62 (Table 2).

In another preferred embodiment, the mRNA molecule encodes a KRAS variant peptide or polypeptide set forth in SEQ ID NO: 48, SEQ ID NO: 49, SEQ ID NO: 50, SEQ ID NO: 51 or SEQ ID NO: 52 (Table 3). In another preferred embodiment, the molecule set forth in SEQ ID NO: 53, SEQ ID NO: 54, SEQ ID NO: 55, SEQ ID NO: 56 or SEQ ID NO: 57.

TABLE 3

| Identifier of KRAS neoepitopes (aa position) | Signal peptide (aa position) | SEQ ID NO: amino acid | SEQ ID NO: optimized nucleic acid |
|---|---|---|---|
| G12C (1-29) | CTLA4 (1-35) | 48 | 53 |
| G12D (1-29) | CTLA4 (1-35) | 49 | 54 |
| G12R (1-29) | CTLA4 (1-35) | 50 | 55 |
| G12V (1-29) | CTLA4 (1-35) | 51 | 56 |
| G13D (1-29) | CTLA4 (1-35) | 52 | 57 |

In another preferred embodiment, the mRNA molecule encodes an amino acid sequence comprising a KRAS G12C variant peptide. In another preferred embodiment, the KRAS G12C variant peptide is SEQ ID NO: 8. In another preferred embodiment, the mRNA molecule encodes an amino acid sequence comprising SEQ ID NO: 48. In another preferred embodiment, the mRNA molecule encodes an amino acid sequence comprising SEQ ID NO: 53. In another preferred embodiment, the mRNA molecule comprises SEQ ID NO: 58. In another preferred embodiment, the mRNA molecule comprises SEQ ID NO: 63.

In another preferred embodiment, the mRNA molecule encodes an amino acid sequence comprising a KRAS G12D variant peptide. In another preferred embodiment, the KRAS G12D variant peptide is SEQ ID NO: 9. In another preferred embodiment, the mRNA molecule encodes an amino acid sequence comprising SEQ ID NO: 49. In another preferred embodiment, the mRNA molecule encodes an amino acid sequence comprising SEQ ID NO: 54. In another preferred embodiment, the mRNA molecule comprises SEQ ID NO: 59. In another preferred embodiment, the mRNA molecule comprises SEQ ID NO: 64.

In another preferred embodiment, the mRNA molecule encodes an amino acid sequence comprising a KRAS G12R variant peptide. In another preferred embodiment, the KRAS G12R variant peptide is SEQ ID NO: 10. In another preferred embodiment, the mRNA molecule encodes an amino acid sequence comprising SEQ ID NO: 50. In another preferred embodiment, the mRNA molecule encodes an amino acid sequence comprising SEQ ID NO: 55. In another preferred embodiment, the mRNA molecule comprises SEQ ID NO: 60. In another preferred embodiment, the mRNA molecule comprises SEQ ID NO: 65.

In another preferred embodiment, the mRNA molecule encodes an amino acid sequence comprising a KRAS G12V variant peptide. In another preferred embodiment, the KRAS G12V variant peptide is SEQ ID NO: 11. In another preferred embodiment, the mRNA molecule encodes an amino acid sequence comprising SEQ ID NO: 51. In another preferred embodiment, the mRNA molecule encodes an amino acid sequence comprising SEQ ID NO: 56. In another preferred embodiment, the mRNA molecule comprises SEQ ID NO: 61. In another preferred embodiment, the mRNA molecule comprises SEQ ID NO: 66.

In another preferred embodiment, the mRNA molecule encodes an amino acid sequence comprising a KRAS G13D variant peptide. In another preferred embodiment, the KRAS G13D variant peptide is SEQ ID NO: 12. In another preferred embodiment, the mRNA molecule encodes an amino acid sequence comprising SEQ ID NO: 52. In another preferred embodiment, the mRNA molecule encodes an amino acid sequence comprising SEQ ID NO: 57. In another preferred embodiment, the mRNA molecule comprises SEQ ID NO: 62. In another preferred embodiment, the mRNA molecule comprises SEQ ID NO: 67.

According to a particularly preferred embodiment, the mRNA molecule further comprises at least one 5'-sequence and/or 3'-UTR sequence.

The present invention also provides a pharmaceutical composition comprising the mRNA molecule of the invention herein, and one or more pharmaceutically acceptable carriers or excipients.

In a preferred embodiment, the pharmaceutical composition comprises 1, 2, 3, 4 or 5 different mRNA molecules, each mRNA molecule encoding a different KRAS variant peptide.

In another preferred embodiment, the pharmaceutical composition comprises an mRNA molecule encoding a single KRAS variant peptide. In another preferred embodiment, the pharmaceutical composition comprises 2 different mRNA molecules, each mRNA molecule encoding a different KRAS variant peptide. In another preferred embodiment, the pharmaceutical composition comprises 3 mRNA molecules, each mRNA molecule encoding a different KRAS variant peptide. In another preferred embodiment, the pharmaceutical composition comprises 4 mRNA molecules, each mRNA molecule encoding a different KRAS variant peptide. In another preferred embodiment, the pharmaceutical composition comprises 5 mRNA molecules, each mRNA encoding a different KRAS variant peptide.

In another preferred embodiment, the pharmaceutical composition comprises an mRNA molecule that encodes an amino acid sequence comprising a KRAS G12C variant peptide. In another preferred embodiment, the KRAS G12C variant peptide is SEQ ID NO: 8. In another preferred embodiment, the mRNA molecule encodes an amino acid sequence comprising SEQ ID NO: 48. In another preferred embodiment, the mRNA molecule encodes an amino acid sequence comprising SEQ ID NO: 53.

In another preferred embodiment, the pharmaceutical composition comprises an mRNA molecule that encodes an amino acid sequence comprising a KRAS G12D variant. In another preferred embodiment, the KRAS G12D variant peptide is SEQ ID NO: 9. In another preferred embodiment, the mRNA molecule encodes an amino acid sequence comprising SEQ ID NO: 49. In another preferred embodiment, the mRNA molecule encodes an amino acid sequence comprising SEQ ID NO: 54.

In another preferred embodiment, the pharmaceutical composition comprises an mRNA molecule that encodes an amino acid sequence comprising a KRAS G12R variant peptide. In another preferred embodiment, the KRAS G12R variant peptide is SEQ ID NO: 10. In another preferred embodiment, the mRNA molecule encodes an amino acid sequence comprising SEQ ID NO: 50. In another preferred embodiment, the mRNA molecule encodes an amino acid sequence comprising SEQ ID NO: 55. In another preferred embodiment, the pharmaceutical composition comprises an mRNA molecule that encodes an amino acid sequence comprising a KRAS G12V variant peptide. In another preferred embodiment, the KRAS G12V variant peptide is SEQ ID NO: 11. In another preferred embodiment, the mRNA molecule encodes an amino acid sequence comprising SEQ ID NO: 51. In another preferred embodiment, the mRNA molecule encodes an amino acid sequence comprising SEQ ID NO: 56. In another preferred embodiment, the pharmaceutical composition comprises an mRNA molecule that encodes an amino acid sequence comprising a KRAS G13D variant peptide. In another preferred embodiment, the KRAS G13D variant peptide is SEQ ID NO: 12. In another preferred embodiment, the mRNA molecule encodes an amino acid sequence comprising SEQ ID NO: 52. In another preferred embodiment, the mRNA molecule encodes an amino acid sequence comprising SEQ ID NO: 57.

In another preferred embodiment, the pharmaceutical composition comprises an mRNA molecule that encodes an amino acid sequence comprising a KRAS G12C variant peptide and an mRNA molecule that encodes an amino acid sequence comprising a KRAS G12D variant peptide. In another preferred embodiment, the KRAS G12C variant peptide is SEQ ID NO: 8, and the KRAS G12D variant peptide is SEQ ID NO: 9. In another preferred embodiment, the pharmaceutical composition comprises an mRNA molecule encoding the amino acid sequence of SEQ ID NO: 48, and an mRNA molecule encoding the amino acid sequence of SEQ ID NO: 49. In another preferred embodiment, the pharmaceutical composition comprises an mRNA molecule encoding the amino acid sequence of SEQ ID NO: 53, and an mRNA molecule encoding the amino acid sequence of SEQ ID NO: 54. In another preferred embodiment, the pharmaceutical composition comprises an mRNA molecule comprising SEQ ID NO: 58, and an mRNA molecule comprising SEQ ID NO: 59. In another preferred embodiment, the pharmaceutical composition comprises an mRNA molecule comprising SEQ ID NO: 63, and an mRNA molecule comprising SEQ ID NO: 64. In another preferred embodiment, the pharmaceutical composition comprises an mRNA molecule that encodes an amino acid sequence comprising a KRAS G12D variant peptide and an mRNA molecule that encodes an amino acid sequence comprising a KRAS G12V variant peptide. In another preferred embodiment, the KRAS G12D variant peptide is SEQ ID NO: 9, and the KRAS G12V variant peptide is SEQ ID NO: 11. In another preferred embodiment, the pharmaceutical composition comprises an mRNA molecule encoding the amino acid sequence of SEQ ID NO: 49, and an mRNA molecule encoding the amino acid sequence of SEQ ID NO: 51. In another preferred embodiment, the pharmaceutical composition comprises an mRNA molecule encoding the amino acid sequence of SEQ ID NO: 54, and an mRNA molecule encoding the amino acid sequence of SEQ ID NO: 56. In another preferred embodiment, the pharmaceutical composition comprises an mRNA molecule comprising SEQ ID NO: 59, and an mRNA molecule comprising SEQ ID NO: 61. In another preferred embodiment, the pharmaceutical composition comprises an mRNA molecule comprising SEQ ID NO: 64, and an mRNA molecule comprising SEQ ID NO: 66.

In another preferred embodiment, the pharmaceutical composition comprises an mRNA molecule that encodes an amino acid sequence comprising a KRAS G12D variant peptide and an mRNA molecule that encodes an amino acid sequence comprising a KRAS G12R variant peptide. In another preferred embodiment, the KRAS G12D variant peptide is SEQ ID NO: 9, and the KRAS G12R variant peptide is SEQ ID NO: 10. In another preferred embodiment, the pharmaceutical composition comprises an mRNA molecule encoding the amino acid sequence of SEQ ID NO: 49, and an mRNA molecule encoding the amino acid sequence of SEQ ID NO: 50. In another preferred embodiment, the pharmaceutical composition comprises an mRNA molecule encoding the amino acid sequence of SEQ ID NO: 54, and an mRNA molecule encoding the amino acid sequence of SEQ ID NO: 55. In another preferred embodiment, the pharmaceutical composition comprises an mRNA molecule comprising SEQ ID NO: 59, and an mRNA molecule comprising SEQ ID NO: 60. In another preferred embodiment, the pharmaceutical composition comprises an mRNA molecule comprising SEQ ID NO: 64, and an mRNA molecule comprising SEQ ID NO: 65.

In another preferred embodiment, the pharmaceutical composition comprises an mRNA molecule that encodes an amino acid sequence comprising a KRAS G12D variant peptide and an mRNA molecule that encodes an amino acid sequence comprising a KRAS G13D variant peptide. In another preferred embodiment, the KRAS G12D variant peptide is SEQ ID NO: 9, and the KRAS G13D variant peptide is SEQ ID NO: 12. In another preferred embodiment, the pharmaceutical composition comprises an mRNA molecule encoding the amino acid sequence of SEQ ID NO: 49, and an mRNA molecule encoding the amino acid sequence of SEQ ID NO: 52. In another preferred embodiment, the pharmaceutical composition comprises an mRNA molecule encoding the amino acid sequence of SEQ ID NO: 54, and an mRNA molecule encoding the amino acid sequence of SEQ ID NO: 57. In another preferred embodiment, the pharmaceutical composition comprises an mRNA molecule comprising SEQ ID NO: 59, and an mRNA molecule comprising SEQ ID NO: 62. In another preferred embodiment, the pharmaceutical composition comprises an mRNA molecule comprising SEQ ID NO: 64, and an mRNA molecule comprising SEQ ID NO: 67.

In another preferred embodiment, the pharmaceutical composition comprises an mRNA molecule that encodes an amino acid sequence comprising a KRAS G12C variant peptide and an mRNA molecule that encodes an amino acid sequence comprising a KRAS G12V variant peptide. In another preferred embodiment, the KRAS G12C variant peptide is SEQ ID NO: 8, and the KRAS G12V variant peptide is SEQ ID NO: 11. In another preferred embodiment, the pharmaceutical composition comprises an mRNA molecule encoding the amino acid sequence of SEQ ID NO: 48, and an mRNA molecule encoding the amino acid sequence of SEQ ID NO: 51. In another preferred embodiment, the pharmaceutical composition comprises an mRNA molecule encoding the amino acid sequence of SEQ ID NO: 53, and an mRNA molecule encoding the amino acid sequence of SEQ ID NO: 56. In another preferred embodiment, the pharmaceutical composition comprises an mRNA molecule comprising SEQ ID NO: 58, and an mRNA molecule comprising SEQ ID NO: 61. In another preferred embodiment, the pharmaceutical composition comprises an mRNA molecule comprising SEQ ID NO: 63, and an mRNA molecule comprising SEQ ID NO: 66.

In another preferred embodiment, the pharmaceutical composition comprises an mRNA molecule that encodes an amino acid sequence comprising a KRAS G12C variant peptide and an mRNA molecule that encodes an amino acid sequence comprising a KRAS G12R variant peptide. In another preferred embodiment, the KRAS G12C variant peptide is SEQ ID NO: 8, and the KRAS G12R variant peptide is SEQ ID NO: 10. In another preferred embodiment, the pharmaceutical composition comprises an mRNA molecule encoding the amino acid sequence of SEQ ID NO: 48, and an mRNA molecule encoding the amino acid sequence of SEQ ID NO: 50. In another preferred embodiment, the pharmaceutical composition comprises an mRNA molecule encoding the amino acid sequence of SEQ ID NO: 53, and an mRNA molecule encoding the amino acid sequence of SEQ ID NO: 55. In another preferred embodiment, the pharmaceutical composition comprises an mRNA molecule comprising SEQ ID NO: 58, and an mRNA molecule comprising SEQ ID NO: 60. In another preferred embodiment, the pharmaceutical composition comprises an mRNA molecule comprising SEQ ID NO: 63, and an mRNA molecule comprising SEQ ID NO: 65.

In another preferred embodiment, the pharmaceutical composition comprises an mRNA molecule that encodes an amino acid sequence comprising a KRAS G12C variant peptide and an mRNA molecule that encodes an amino acid sequence comprising a KRAS G13D variant peptide. In another preferred embodiment, the KRAS G12C variant peptide is SEQ ID NO: 8, and the KRAS G13D variant peptide is SEQ ID NO: 12. In another preferred embodiment, the pharmaceutical composition comprises an mRNA molecule encoding the amino acid sequence of SEQ ID NO: 48, and an mRNA molecule encoding the amino acid sequence of SEQ ID NO: 52. In another preferred embodiment, the pharmaceutical composition comprises an mRNA molecule encoding the amino acid sequence of SEQ ID NO: 53, and an mRNA molecule encoding the amino acid sequence of SEQ ID NO: 57. In another preferred embodiment, the pharmaceutical composition comprises an mRNA molecule comprising SEQ ID NO: 58, and an mRNA molecule comprising SEQ ID NO: 62. In another preferred embodiment, the pharmaceutical composition comprises an mRNA molecule comprising SEQ ID NO: 63, and an mRNA molecule comprising SEQ ID NO: 67.

In another preferred embodiment, the pharmaceutical composition comprises an mRNA molecule that encodes an amino acid sequence comprising a KRAS G12R variant peptide and an mRNA molecule that encodes an amino acid sequence comprising a KRAS G12V variant peptide. In another preferred embodiment, the KRAS G12R variant peptide is SEQ ID NO: 10, and the KRAS G12V variant peptide is SEQ ID NO: 11. In another preferred embodiment, the pharmaceutical composition comprises an mRNA molecule encoding the amino acid sequence of SEQ ID NO: 50, and an mRNA molecule encoding the amino acid sequence of SEQ ID NO: 51. In another preferred embodiment, the pharmaceutical composition comprises an mRNA molecule encoding the amino acid sequence of SEQ ID NO: 55, and an mRNA molecule encoding the amino acid sequence of SEQ ID NO: 56. In another preferred embodiment, the pharmaceutical composition comprises an mRNA molecule comprising SEQ ID NO: 60, and an mRNA molecule comprising SEQ ID NO: 61. In another preferred embodiment, the pharmaceutical composition comprises an mRNA molecule comprising SEQ ID NO: 65, and an mRNA molecule comprising SEQ ID NO: 66.

In another preferred embodiment, the pharmaceutical composition comprises an mRNA molecule that encodes an amino acid sequence comprising a KRAS G12V variant peptide and an mRNA molecule that encodes an amino acid sequence comprising a KRAS G13D variant peptide. In another preferred embodiment, the KRAS G12V variant peptide is SEQ ID NO: 11, and the KRAS G13D variant peptide is SEQ ID NO: 12. In another preferred embodiment, the pharmaceutical composition comprises an mRNA molecule encoding the amino acid sequence of SEQ ID NO: 51, and an mRNA molecule encoding the amino acid sequence of SEQ ID NO: 52. In another preferred embodiment, the pharmaceutical composition comprises an mRNA molecule encoding the amino acid sequence of SEQ ID NO: 56, and an mRNA molecule encoding the amino acid sequence of SEQ ID NO: 57. In another preferred embodiment, the pharmaceutical composition comprises an mRNA molecule comprising SEQ ID NO: 61, and an mRNA molecule comprising SEQ ID NO: 62. In another preferred embodiment, the pharmaceutical composition comprises an mRNA molecule comprising SEQ ID NO: 66, and an mRNA molecule comprising SEQ ID NO: 67.

In another preferred embodiment, the pharmaceutical composition comprises an mRNA molecule that encodes an amino acid sequence comprising a KRAS G12R variant peptide and an mRNA molecule that encodes an amino acid sequence comprising a KRAS G13D variant peptide. In another preferred embodiment, the KRAS G12R variant peptide is SEQ ID NO: 10, and the KRAS G13D variant peptide is SEQ ID NO: 12. In another preferred embodiment, the pharmaceutical composition comprises an mRNA molecule encoding the amino acid sequence of SEQ ID NO: 50, and an mRNA molecule encoding the amino acid sequence of SEQ ID NO: 52. In another preferred embodiment, the pharmaceutical composition comprises an mRNA molecule encoding the amino acid sequence of SEQ ID NO: 55, and an mRNA molecule encoding the amino acid sequence of SEQ ID NO: 57. In another preferred embodiment, the pharmaceutical composition comprises an mRNA molecule comprising SEQ ID NO: 60, and an mRNA molecule comprising SEQ ID NO: 62. In another preferred embodiment, the pharmaceutical composition comprises an mRNA molecule comprising SEQ ID NO: 65, and an mRNA molecule comprising SEQ ID NO: 67.

In another preferred embodiment, the pharmaceutical composition comprises an mRNA molecule that encodes an amino acid sequence comprising a KRAS G12D variant peptide, an mRNA molecule that encodes an amino acid sequence comprising a KRAS G12C variant peptide, and an mRNA molecule that encodes an amino acid sequence comprising a KRAS G12V variant peptide. In another preferred embodiment, the KRAS G12C variant peptide is SEQ ID NO: 8, the KRAS G12D variant peptide is SEQ ID NO: 9, and the KRAS G12V variant peptide is SEQ ID NO: 11. In another preferred embodiment, the pharmaceutical composition comprises an mRNA molecule encoding the amino acid sequence of SEQ ID NO: 48, an mRNA molecule encoding the amino acid sequence of SEQ ID NO: 49, an mRNA molecule encoding the amino acid sequence of SEQ ID NO: 51. In another preferred embodiment, the pharmaceutical composition comprises an mRNA molecule encoding the amino acid sequence of SEQ ID NO: 53, an mRNA molecule encoding the amino acid sequence of SEQ ID NO: 54, and an mRNA molecule encoding the amino acid sequence of SEQ ID NO: 56. In another preferred embodiment, the pharmaceutical composition comprises an mRNA molecule comprising SEQ ID NO: 58, an mRNA molecule comprising SEQ ID NO: 59, and an mRNA molecule comprising SEQ ID NO: 61. In another preferred embodiment, the pharmaceutical composition comprises an mRNA molecule comprising SEQ ID NO: 63, an mRNA molecule comprising SEQ ID NO: 64, and an mRNA molecule comprising SEQ ID NO: 66.

In another preferred embodiment, the pharmaceutical composition comprises an mRNA molecule that encodes an amino acid sequence comprising a KRAS G12D variant peptide, an mRNA molecule that encodes an amino acid sequence comprising a KRAS G12C variant peptide, and an mRNA molecule that encodes an amino acid sequence comprising a KRAS G12R variant peptide. In another preferred embodiment, the KRAS G12C variant peptide is SEQ ID NO: 8, the KRAS G12D variant peptide is SEQ ID NO: 9, and the KRAS G12R variant peptide is SEQ ID NO: 10. In another preferred embodiment, the pharmaceutical composition comprises an mRNA molecule encoding the amino acid sequence of SEQ ID NO: 48, an mRNA molecule encoding the amino acid sequence of SEQ ID NO: 49, an mRNA molecule encoding the amino acid sequence of SEQ ID NO: 50. In another preferred embodiment, the pharmaceutical composition comprises an mRNA molecule encoding the amino acid sequence of SEQ ID NO: 53, an mRNA molecule encoding the amino acid sequence of SEQ ID NO: 54, and an mRNA molecule encoding the amino acid sequence of SEQ ID NO: 55. In another preferred embodiment, the pharmaceutical composition comprises an mRNA molecule comprising SEQ ID NO: 58, an mRNA molecule comprising SEQ ID NO: 59, and an mRNA molecule comprising SEQ ID NO: 60. In another preferred embodiment, the pharmaceutical composition comprises an mRNA molecule comprising SEQ ID NO: 63, an mRNA molecule comprising SEQ ID NO: 64, and an mRNA molecule comprising SEQ ID NO: 65.

In another preferred embodiment, the pharmaceutical composition comprises an mRNA molecule that encodes an amino acid sequence comprising a KRAS G12D variant peptide, an mRNA molecule that encodes an amino acid sequence comprising a KRAS G12C variant peptide, and an mRNA molecule that encodes an amino acid sequence comprising a KRAS G13D variant peptide. In another preferred embodiment, the KRAS G12C variant peptide is SEQ ID NO: 8, the KRAS G12D variant peptide is SEQ ID NO: 9, and the KRAS G13D variant peptide is SEQ ID NO: 12. In another preferred embodiment, the pharmaceutical composition comprises an mRNA molecule encoding the amino acid sequence of SEQ ID NO: 48, an mRNA molecule encoding the amino acid sequence of SEQ ID NO: 49, an mRNA molecule encoding the amino acid sequence of SEQ ID NO: 52. In another preferred embodiment, the pharmaceutical composition comprises an mRNA molecule encoding the amino acid sequence of SEQ ID NO: 53, an mRNA molecule encoding the amino acid sequence of SEQ ID NO: 54, and an mRNA molecule encoding the amino acid sequence of SEQ ID NO: 57. In another preferred embodiment, the pharmaceutical composition comprises an mRNA molecule comprising SEQ ID NO: 58, an mRNA molecule comprising SEQ ID NO: 59, and an mRNA molecule comprising SEQ ID NO: 62. In another preferred embodiment, the pharmaceutical composition comprises an mRNA molecule comprising SEQ ID NO: 63, an mRNA molecule comprising SEQ ID NO: 64, and an mRNA molecule comprising SEQ ID NO: 67.

In another preferred embodiment, the pharmaceutical composition comprises an mRNA molecule that encodes an amino acid sequence comprising the KRAS G12D variant peptide, an mRNA molecule that encodes an amino acid sequence comprising the KRAS G12R variant peptide, and an mRNA molecule that encodes an amino acid sequence comprising the KRAS G12V variant peptide. In another preferred embodiment, the KRAS G12D variant peptide is SEQ ID NO: 9, the KRAS G12R variant peptide is SEQ ID NO: 10, and the KRAS G12V variant peptide is SEQ ID NO: 11. In another preferred embodiment, the pharmaceutical composition comprises an mRNA molecule encoding the amino acid sequence of SEQ ID NO: 49, an mRNA molecule encoding the amino acid sequence of SEQ ID NO: 50, an mRNA molecule encoding the amino acid sequence of SEQ ID NO: 51. In another preferred embodiment, the pharmaceutical composition comprises an mRNA molecule encoding the amino acid sequence of SEQ ID NO: 54, an mRNA molecule encoding the amino acid sequence of SEQ ID NO: 55, and an mRNA molecule encoding the amino acid sequence of SEQ ID NO: 56. In another preferred embodiment, the pharmaceutical composition comprises an mRNA molecule comprising SEQ ID NO: 59, an mRNA molecule comprising SEQ ID NO: 60, and an mRNA molecule comprising SEQ ID NO: 61. In another preferred embodiment, the pharmaceutical composition comprises an mRNA molecule comprising SEQ ID NO: 64, an mRNA molecule comprising SEQ ID NO: 65, and an mRNA molecule comprising SEQ ID NO: 66.

In another preferred embodiment, the pharmaceutical composition comprises an mRNA molecule that encodes an amino acid sequence comprising the KRAS G12D variant peptide, an mRNA molecule that encodes an amino acid sequence comprising the KRAS G12V variant peptide, and an mRNA molecule that encodes an amino acid sequence comprising the KRAS G13D variant peptide. In another preferred embodiment, the KRAS G12D variant peptide is SEQ ID NO: 9, the KRAS G12V variant peptide is SEQ ID NO: 11, and the KRAS G13D variant peptide is SEQ ID NO: 12. In another preferred embodiment, the pharmaceutical composition comprises an mRNA molecule encoding the amino acid sequence of SEQ ID NO: 49, an mRNA molecule encoding the amino acid sequence of SEQ ID NO: 51, an mRNA molecule encoding the amino acid sequence of SEQ ID NO: 52. In another preferred embodiment, the pharmaceutical composition comprises an mRNA molecule encoding the amino acid sequence of SEQ ID NO: 54, an mRNA molecule encoding the amino acid sequence of SEQ ID NO: 56, and an mRNA molecule encoding the amino acid sequence of SEQ ID NO: 57. In another preferred embodiment, the pharmaceutical composition comprises an mRNA molecule comprising SEQ ID NO: 59, an mRNA molecule comprising SEQ ID NO: 61, and an mRNA molecule comprising SEQ ID NO: 62. In another preferred embodiment, the pharmaceutical composition comprises an mRNA molecule comprising SEQ ID NO: 64, an mRNA molecule comprising SEQ ID NO: 66, and an mRNA molecule comprising SEQ ID NO: 67.

In another preferred embodiment, the pharmaceutical composition comprises an mRNA molecule that encodes an amino acid sequence comprising the KRAS G12D variant peptide, an mRNA molecule that encodes an amino acid sequence comprising the KRAS G12R variant peptide, and an mRNA molecule that encodes an amino acid sequence comprising the KRAS G13D variant peptide. In another preferred embodiment, the KRAS G12D variant peptide is SEQ ID NO: 9, the KRAS G12R variant peptide is SEQ ID NO: 10, and the KRAS G13D variant peptide is SEQ ID NO: 12. In another preferred embodiment, the pharmaceutical composition comprises an mRNA molecule encoding the amino acid sequence of SEQ ID NO: 49, an mRNA molecule encoding the amino acid sequence of SEQ ID NO: 50, an mRNA molecule encoding the amino acid sequence of SEQ ID NO: 52. In another preferred embodiment, the pharmaceutical composition comprises an mRNA molecule encoding the amino acid sequence of SEQ ID NO: 54, an mRNA molecule encoding the amino acid sequence of SEQ ID NO: 55, and an mRNA molecule encoding the amino acid sequence of SEQ ID NO: 57. In another preferred embodiment, the pharmaceutical composition comprises an mRNA molecule comprising SEQ ID NO: 59, an mRNA molecule comprising SEQ ID NO: 60, and an mRNA molecule comprising SEQ ID NO: 62. In another preferred embodiment, the pharmaceutical composition comprises an mRNA molecule comprising SEQ ID NO: 64, an mRNA molecule comprising SEQ ID NO: 65, and an mRNA molecule comprising SEQ ID NO: 67.

In another preferred embodiment, the pharmaceutical composition comprises an mRNA molecule that encodes an amino acid sequence comprising the KRAS G12C variant peptide, an mRNA molecule that encodes an amino acid sequence comprising the KRAS G12R variant peptide, and an mRNA molecule that encodes an amino acid sequence comprising the KRAS G12V variant peptide. In another preferred embodiment, the KRAS G12C variant peptide is SEQ ID NO: 8, the KRAS G12R variant peptide is SEQ ID NO: 10, and the KRAS G12V variant peptide is SEQ ID NO: 11. In another preferred embodiment, the pharmaceutical composition comprises an mRNA molecule encoding the amino acid sequence of SEQ ID NO: 48, an mRNA molecule encoding the amino acid sequence of SEQ ID NO: 50, an mRNA molecule encoding the amino acid sequence of SEQ ID NO: 51. In another preferred embodiment, the pharmaceutical composition comprises an mRNA molecule encoding the amino acid sequence of SEQ ID NO: 53, an mRNA molecule encoding the amino acid sequence of SEQ ID NO: 55, and an mRNA molecule encoding the amino acid sequence of SEQ ID NO: 56. In another preferred embodiment, the pharmaceutical composition comprises an mRNA molecule comprising SEQ ID NO: 58, an mRNA molecule comprising SEQ ID NO: 60, and an mRNA molecule comprising SEQ ID NO: 61. In another preferred embodiment, the pharmaceutical composition comprises an mRNA molecule comprising SEQ ID NO: 63, an mRNA molecule comprising SEQ ID NO: 65, and an mRNA molecule comprising SEQ ID NO: 66.

In another preferred embodiment, the pharmaceutical composition comprises an mRNA molecule that encodes an amino acid sequence comprising the KRAS G12C variant peptide, an mRNA molecule that encodes an amino acid sequence comprising the KRAS G12V variant peptide, and an mRNA molecule that encodes an amino acid sequence comprising the KRAS G13D variant peptide. In another preferred embodiment, the KRAS G12C variant peptide is SEQ ID NO: 8, and the KRAS G12V variant peptide is SEQ ID NO: 11, and the KRAS G13D variant peptide is SEQ ID NO: 12. In another preferred embodiment, the pharmaceutical composition comprises an mRNA molecule encoding the amino acid sequence of SEQ ID NO: 48, an mRNA molecule encoding the amino acid sequence of SEQ ID NO: 51, an mRNA molecule encoding the amino acid sequence of SEQ ID NO: 52. In another preferred embodiment, the pharmaceutical composition comprises an mRNA molecule encoding the amino acid sequence of SEQ ID NO: 53, an mRNA molecule encoding the amino acid sequence of SEQ ID NO: 56, and an mRNA molecule encoding the amino acid sequence of SEQ ID NO: 57. In another preferred embodiment, the pharmaceutical composition comprises an mRNA molecule comprising SEQ ID NO: 58, an mRNA molecule comprising SEQ ID NO: 61, and an mRNA molecule comprising SEQ ID NO: 62. In another preferred embodiment, the pharmaceutical composition comprises an mRNA molecule comprising SEQ ID NO: 63, an mRNA molecule comprising SEQ ID NO: 66, and an mRNA molecule comprising SEQ ID NO: 67.

In another preferred embodiment, the pharmaceutical composition comprises an mRNA molecule that encodes an amino acid sequence comprising the KRAS G12C variant peptide, an mRNA molecule that encodes an amino acid sequence comprising the KRAS G12R variant peptide, and an mRNA molecule that encodes an amino acid sequence comprising the KRAS G13D variant peptide. In another preferred embodiment, the KRAS G12C variant peptide is SEQ ID NO: 8, the KRAS G12R variant peptide is SEQ ID NO: 10, and the KRAS G13D variant peptide is SEQ ID NO: 12. In another preferred embodiment, the pharmaceutical composition comprises an mRNA molecule encoding the amino acid sequence of SEQ ID NO: 48, an mRNA molecule encoding the amino acid sequence of SEQ ID NO: 50, an mRNA molecule encoding the amino acid sequence of SEQ ID NO: 52. In another preferred embodiment, the pharmaceutical composition comprises an mRNA molecule encoding the amino acid sequence of SEQ ID NO: 53, an mRNA molecule encoding the amino acid sequence of SEQ ID NO: 55, and an mRNA molecule encoding the amino acid sequence of SEQ ID NO: 57. In another preferred embodiment, the pharmaceutical composition comprises an mRNA molecule comprising SEQ ID NO: 58, an mRNA molecule comprising SEQ ID NO: 60, and an mRNA molecule comprising SEQ ID NO: 62. In another preferred embodiment, the pharmaceutical composition comprises an mRNA molecule comprising SEQ ID NO: 63, an mRNA molecule comprising SEQ ID NO: 65, and an mRNA molecule comprising SEQ ID NO: 67.

In another preferred embodiment, the pharmaceutical composition comprises an mRNA molecule that encodes an amino acid sequence comprising a KRAS G12R variant peptide, an mRNA molecule that encodes an amino acid sequence comprising a KRAS G12V variant peptide, and an mRNA molecule that encodes an amino acid sequence comprising a KRAS G13D variant peptide. In another preferred embodiment, the KRAS G12R variant peptide is SEQ ID NO: 10, the KRAS G12V variant peptide is SEQ ID NO: 11, and the KRAS G13D variant peptide is SEQ ID NO: 12. In another preferred embodiment, the pharmaceutical composition comprises an mRNA molecule encoding the amino acid sequence of SEQ ID NO: 50, an mRNA molecule encoding the amino acid sequence of SEQ ID NO: 51, an mRNA molecule encoding the amino acid sequence of SEQ ID NO: 52. In another preferred embodiment, the pharmaceutical composition comprises an mRNA molecule encoding the amino acid sequence of SEQ ID NO: 55, an mRNA molecule encoding the amino acid sequence of SEQ ID NO: 56, and an mRNA molecule encoding the amino acid sequence of SEQ ID NO: 57. In another preferred embodiment, the pharmaceutical composition comprises an mRNA molecule comprising SEQ ID NO: 60, an mRNA molecule comprising SEQ ID NO: 61, and an mRNA molecule comprising SEQ ID NO: 62. In another preferred embodiment, the pharmaceutical composition comprises an mRNA molecule comprising SEQ ID NO: 65, an mRNA molecule comprising SEQ ID NO: 66, and an mRNA molecule comprising SEQ ID NO: 67.

In another preferred embodiment, the pharmaceutical composition comprises an mRNA molecule that encodes an amino acid sequence comprising a KRAS G12C variant peptide, an mRNA molecule that encodes an amino acid sequence comprising a KRAS G12D variant peptide, an mRNA molecule that encodes an amino acid sequence comprising a KRAS G12R variant peptide, and an mRNA molecule that encodes an amino acid sequence comprising a KRAS G12V variant peptide. In another preferred embodiment, the KRAS G12C variant peptide is SEQ ID NO: 8, the KRAS G12D variant peptide is SEQ ID NO: 9, the KRAS G12R variant peptide is SEQ ID NO: 10, and the KRAS G12V variant peptide is SEQ ID NO: 11. In another preferred embodiment, the pharmaceutical composition comprises an mRNA molecule encoding the amino acid sequence of SEQ ID NO: 48, an mRNA molecule encoding the amino acid sequence of SEQ ID NO: 49, an mRNA molecule encoding the amino acid sequence of SEQ ID NO: 50, and an mRNA molecule encoding the amino acid sequence of SEQ ID NO: 51. In another preferred embodiment, the pharmaceutical composition comprises an mRNA molecule encoding the amino acid sequence of SEQ ID NO: 53, an mRNA molecule encoding the amino acid sequence of SEQ ID NO: 54, an mRNA molecule encoding the amino acid sequence of SEQ ID NO: 55, and an mRNA molecule encoding the amino acid sequence of SEQ ID NO: 56. In another preferred embodiment, the pharmaceutical composition comprises an mRNA molecule comprising SEQ ID NO: 58, an mRNA molecule comprising SEQ ID NO: 59, an mRNA molecule comprising SEQ ID NO: 60, and an mRNA molecule comprising SEQ ID NO: 61. In another preferred embodiment, the pharmaceutical composition comprises an mRNA molecule comprising SEQ ID NO: 63, an mRNA molecule comprising SEQ ID NO: 64, an mRNA molecule comprising SEQ ID NO: 65, and an mRNA molecule comprising SEQ ID NO: 66.

In another preferred embodiment, the pharmaceutical composition comprises an mRNA molecule that encodes an amino acid sequence comprising a KRAS G12C variant peptide, an mRNA molecule that encodes an amino acid sequence comprising a KRAS G12D variant peptide, an mRNA molecule that encodes an amino acid sequence comprising a KRAS G12V variant peptide, and an mRNA molecule that encodes an amino acid sequence comprising a KRAS G13D variant peptide. In another preferred embodiment, the KRAS G12C variant peptide is SEQ ID NO: 8, the KRAS G12D variant peptide is SEQ ID NO: 9, the KRAS G12V variant peptide is SEQ ID NO: 11, and the KRAS G13D variant peptide is SEQ ID NO: 12. In another preferred embodiment, the pharmaceutical composition comprises an mRNA molecule encoding the amino acid sequence of SEQ ID NO: 48, an mRNA molecule encoding the amino acid sequence of SEQ ID NO: 49, an mRNA molecule encoding the amino acid sequence of SEQ ID NO: 51, and an mRNA molecule encoding the amino acid sequence of SEQ ID NO: 52. In another preferred embodiment, the pharmaceutical composition comprises an mRNA molecule encoding the amino acid sequence of SEQ ID NO: 53, an mRNA molecule encoding the amino acid sequence of SEQ ID NO: 54, an mRNA molecule encoding the amino acid sequence of SEQ ID NO: 56, and an mRNA molecule encoding the amino acid sequence of SEQ ID NO: 57. In another preferred embodiment, the pharmaceutical composition comprises an mRNA molecule comprising SEQ ID NO: 58, an mRNA molecule comprising SEQ ID NO: 59, an mRNA molecule comprising SEQ ID NO: 61, and an mRNA molecule comprising SEQ ID NO: 62. In another preferred embodiment, the pharmaceutical composition comprises an mRNA molecule comprising SEQ ID NO: 63, an mRNA molecule comprising SEQ ID NO: 64, an mRNA molecule comprising SEQ ID NO: 66, and an mRNA molecule comprising SEQ ID NO: 67.

In another preferred embodiment, the pharmaceutical composition comprises an mRNA molecule that encodes an amino acid sequence comprising a KRAS G12C variant peptide, an mRNA molecule that encodes an amino acid sequence comprising a KRAS G12D variant peptide, an mRNA molecule that encodes an amino acid sequence comprising a KRAS G12R variant peptide, and an mRNA molecule that encodes an amino acid sequence comprising a KRAS G13D variant peptide. In another preferred embodiment, the KRAS G12C variant peptide is SEQ ID NO: 8, the KRAS G12D variant peptide is SEQ ID NO: 9, the KRAS G12R variant peptide is SEQ ID NO: 10, and the KRAS G13D variant peptide is SEQ ID NO: 12. In another preferred embodiment, the pharmaceutical composition comprises an mRNA molecule encoding the amino acid sequence of SEQ ID NO: 48, an mRNA molecule encoding the amino acid sequence of SEQ ID NO: 49, an mRNA molecule encoding the amino acid sequence of SEQ ID NO:

50, and an mRNA molecule encoding the amino acid sequence of SEQ ID NO: 52. In another preferred embodiment, the pharmaceutical composition comprises an mRNA molecule encoding the amino acid sequence of SEQ ID NO: 53, an mRNA molecule encoding the amino acid sequence of SEQ ID NO: 54, an mRNA molecule encoding the amino acid sequence of SEQ ID NO: 55, and an mRNA molecule encoding the amino acid sequence of SEQ ID NO: 57. In another preferred embodiment, the pharmaceutical composition comprises an mRNA molecule comprising SEQ ID NO: 58, an mRNA molecule comprising SEQ ID NO: 59, an mRNA molecule comprising SEQ ID NO: 60, and an mRNA molecule comprising SEQ ID NO: 62. In another preferred embodiment, the pharmaceutical composition comprises an mRNA molecule comprising SEQ ID NO: 63, an mRNA molecule comprising SEQ ID NO: 64, an mRNA molecule comprising SEQ ID NO: 65, and an mRNA molecule comprising SEQ ID NO: 67.

In another preferred embodiment, the pharmaceutical composition comprises an mRNA molecule that encodes an amino acid sequence comprising a KRAS G12D variant peptide, an mRNA molecule that encodes an amino acid sequence comprising a KRAS G12V variant peptide, an mRNA molecule that encodes an amino acid sequence comprising a KRAS G12R variant peptide, and an mRNA molecule that encodes an amino acid sequence comprising a KRAS G13D variant peptide. In another preferred embodiment, the KRAS G12D variant peptide is SEQ ID NO: 9, the KRAS G12R variant peptide is SEQ ID NO: 10, the KRAS G12V variant peptide is SEQ ID NO: 11, and the KRAS G13D variant peptide is SEQ ID NO: 12. In another preferred embodiment, the pharmaceutical composition comprises an mRNA molecule encoding the amino acid sequence of SEQ ID NO: 49, an mRNA molecule encoding the amino acid sequence of SEQ ID NO: 50, an mRNA molecule encoding the amino acid sequence of SEQ ID NO: 51, and an mRNA molecule encoding the amino acid sequence of SEQ ID NO: 52. In another preferred embodiment, the pharmaceutical composition comprises an mRNA molecule encoding the amino acid sequence of SEQ ID NO: 54, an mRNA molecule encoding the amino acid sequence of SEQ ID NO: 55, an mRNA molecule encoding the amino acid sequence of SEQ ID NO: 56, and an mRNA molecule encoding the amino acid sequence of SEQ ID NO: 57. In another preferred embodiment, the pharmaceutical composition comprises an mRNA molecule comprising SEQ ID NO: 59, an mRNA molecule comprising SEQ ID NO: 60, an mRNA molecule comprising SEQ ID NO: 61, and an mRNA molecule comprising SEQ ID NO: 62. In another preferred embodiment, the pharmaceutical composition comprises an mRNA molecule comprising SEQ ID NO: 64, an mRNA molecule comprising SEQ ID NO: 65, an mRNA molecule comprising SEQ ID NO: 66, and an mRNA molecule comprising SEQ ID NO: 67.

In another preferred embodiment, the pharmaceutical composition comprises an mRNA molecule that encodes an amino acid sequence comprising a KRAS G12C variant peptide, an mRNA molecule that encodes an amino acid sequence comprising a KRAS G12V variant peptide, an mRNA molecule that encodes an amino acid sequence comprising a KRAS G12R variant peptide, and an mRNA molecule that encodes an amino acid sequence comprising a KRAS G13D variant peptide. In another preferred embodiment, the KRAS G12C variant peptide is SEQ ID NO: 8, the KRAS G12R variant peptide is SEQ ID NO: 10, the KRAS G12V variant peptide is SEQ ID NO: 11, and the KRAS G13D variant peptide is SEQ ID NO: 12. In another preferred embodiment, the pharmaceutical composition comprises an mRNA molecule encoding the amino acid sequence of SEQ ID NO: 48, an mRNA molecule encoding the amino acid sequence of SEQ ID NO: 50, an mRNA molecule encoding the amino acid sequence of SEQ ID NO: 51, and an mRNA molecule encoding the amino acid sequence of SEQ ID NO: 52. In another preferred embodiment, the pharmaceutical composition comprises an mRNA molecule encoding the amino acid sequence of SEQ ID NO: 53, an mRNA molecule encoding the amino acid sequence of SEQ ID NO: 55, an mRNA molecule encoding the amino acid sequence of SEQ ID NO: 56, and an mRNA molecule encoding the amino acid sequence of SEQ ID NO: 57. In another preferred embodiment, the pharmaceutical composition comprises an mRNA molecule comprising SEQ ID NO: 58, an mRNA molecule comprising SEQ ID NO: 60, an mRNA molecule comprising SEQ ID NO: 61, and an mRNA molecule comprising SEQ ID NO: 62. In another preferred embodiment, the pharmaceutical composition comprises an mRNA molecule comprising SEQ ID NO: 63, an mRNA molecule comprising SEQ ID NO: 65, an mRNA molecule comprising SEQ ID NO: 66, and an mRNA molecule comprising SEQ ID NO: 67.

In another preferred embodiment, the pharmaceutical composition comprises an mRNA molecule that encodes an amino acid sequence comprising a KRAS G12C variant peptide, an mRNA molecule that encodes an amino acid sequence comprising a KRAS G12D variant peptide, an mRNA molecule that encodes an amino acid sequence comprising a KRAS G12R variant peptide, an mRNA molecule that encodes an amino acid sequence comprising a KRAS G12V variant peptide, and an mRNA molecule that encodes an amino acid sequence comprising a KRAS G13D variant peptide. In another preferred embodiment, the KRAS G12C variant peptide is SEQ ID NO: 8, the KRAS G12D variant peptide is SEQ ID NO: 9, the KRAS G12R variant peptide is SEQ ID NO: 10, the KRAS G12V variant peptide is SEQ ID NO: 11, and the KRAS G13D variant peptide is SEQ ID NO: 12. In another preferred embodiment, the pharmaceutical composition comprises an mRNA molecule encoding the amino acid sequence of SEQ ID NO: 48, an mRNA molecule encoding the amino acid sequence of SEQ ID NO: 49, an mRNA molecule encoding the amino acid sequence of SEQ ID NO: 50, an mRNA molecule encoding the amino acid sequence of SEQ ID NO: 51, and an mRNA molecule encoding the amino acid sequence of SEQ ID NO: 52. In another preferred embodiment, pharmaceutical composition comprise an mRNA molecule encoding the amino acid sequence of SEQ ID NO: 53, an mRNA molecule encoding the amino acid sequence of SEQ ID NO: 54, an mRNA molecule encoding the amino acid sequence of SEQ ID NO: 55, an mRNA molecule encoding the amino acid sequence of SEQ ID NO: 56, and an mRNA molecule encoding the amino acid sequence of SEQ ID NO: 57. In another preferred embodiment, the pharmaceutical composition comprises an mRNA molecule comprising SEQ ID NO: 58, an mRNA molecule comprising SEQ ID NO: 59, an mRNA molecule comprising SEQ ID NO: 60, an mRNA molecule comprising SEQ ID NO: 61, and an mRNA molecule comprising SEQ ID NO: 62. In another preferred embodiment, the pharmaceutical composition comprises an mRNA molecule comprising SEQ ID NO: 63, an mRNA molecule comprising SEQ ID NO: 64, an mRNA molecule comprising SEQ ID NO: 65, an mRNA molecule comprising SEQ ID NO: 66, and an mRNA molecule comprising SEQ ID NO: 67.

In another preferred embodiment, the pharmaceutical composition further comprises a cationic lipid, a sterol, a neutral lipid, and a PEG lipid.

In another preferred embodiment, the pharmaceutical composition comprises: one or more of the mRNA molecules set forth in SEQ ID NOS: 63-67; cholesterol; 2-mPEG2000-n,n ditetradecylacetamide; 1,2-distearoyl-sn-glycero-3-phosphocholine (DSPC); and the cationic lipid

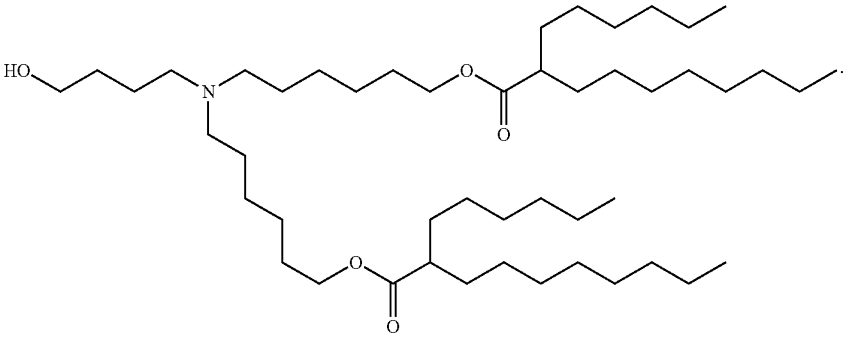 [SMILES: CCCCCCCCC(CCCCCC)C(=O)OCCCCCCN(CCCCO)CCCCCCOC(=O)C(CCCCCC)CCCCCCCC]

In another preferred embodiment, the molar ratio of cationic lipid:DSPC:cholesterol:PEG-lipid is approximately 50:10:38.5:1.5, 47.5:10:40.8:1.7 or 47.4:10:40.9:1.7 mol %.

In another preferred embodiment, the pharmaceutical composition comprising one or more of the mRNA molecules set forth in SEQ ID NOS: 58-62; cholesterol; 2-mPEG2000-n,n ditetradecylacetamide; 1,2-distearoyl-sn-glycero-3-phosphocholine (DSPC); and the cationic lipid

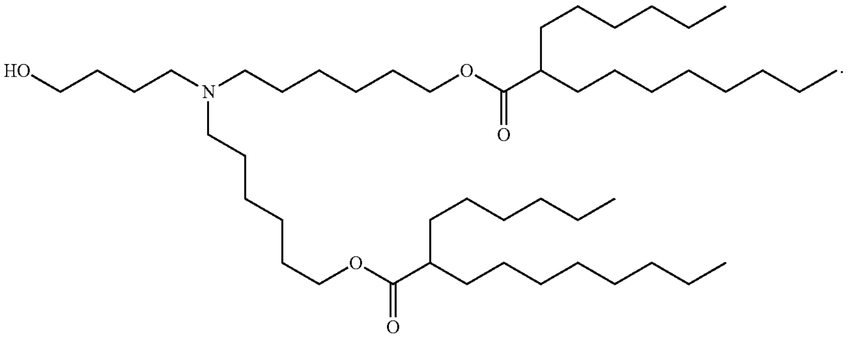 [SMILES: CCCCCCCCC(CCCCCC)C(=O)OCCCCCCN(CCCCO)CCCCCCOC(=O)C(CCCCCC)CCCCCCCC]

In another preferred embodiment, the molar ratio of cationic lipid:DSPC:cholesterol:PEG-lipid is approximately 50:10:38.5:1.5, 47.5:10:40.8:1.7 or preferably 47.4:10:40.9:1.7 mol %.

The present invention also provides a kit comprising the mRNA molecule(s) according to any one of claims 1-16 and optionally instructions with information on the administration and dosage of the mRNA molecule(s).

In one preferred embodiment, the present invention provides the mRNA molecule of the invention or the pharmaceutical composition of the invention for human administration.

According to a further aspect, the invention relates to the mRNA molecule or the pharmaceutical composition of the invention for use in the treatment of cancer. Thus, the present invention provides a method for treating cancer, comprising administering an effective amount of one or more mRNA molecules of the present invention to a subject in need thereof. In one embodiment, the cancer is a solid tumor cancer that is bladder cancer, breast cancer, cervical cancer, colorectal cancer, endometrial cancer, head and neck cancer, liver cancer, lung cancer, non-small cell lung cancer, melanoma, ovarian cancer, pancreatic cancer, prostate cancer, renal cancer, stomach (gastric) cancer, testicular cancer, thyroid cancer, or uterine cancer.

In a particularly preferred embodiment, the cancer is a non-small cell lung cancer (NSCLC), colorectal cancer (CRC) or pancreatic cancer.

In another preferred embodiment, the lung cancer is non-small cell lung cancer. In another preferred embodiment, the non-small cell lung cancer is a squamous cell carcinoma, large cell carcinoma or an adenocarcinoma. In another preferred embodiment, the non-small cell lung cancer is advanced and/or metastatic non-small cell lung cancer, even more preferably unresectable and/or advanced non-small cell lung cancer. In another preferred embodiment, the non-small cell lung cancer is advanced and/or metastatic non-small cell lung cancer is refractory to standard of care treatments. In another preferred embodiment, the non-small cell lung cancer is a nonmetastatic resectable non-small cell lung cancer or non-small cell lung cancer after surgical resection without evidence of residual disease or non-small cell lung cancer amenable to chemoradiation therapy of after chemoradiation therapy without evidence of residual disease.

In another preferred embodiment the colorectal cancer is a colon cancer or a rectal cancer. In another preferred embodiment, the colorectal cancer is advanced and/or metastatic colorectal cancer, even more preferably advanced and/or metastatic hypermutated cancers with either microsatellite instability (MSI) or non-hypermutated, microsatellite stability (MSS). In another preferred embodiment, the colorectal cancer is a resectable colorectal cancer, rectal cancer amenable to or after chemoradiation therapy or a colorectal cancer after surgical resection without evidence of residual disease with either microsatellite instability (MSI) or non-hypermutated, microsatellite stability (MSS).

In another preferred embodiment, the colorectal cancer is a resectable colorectal cancer, rectal cancer amenable to or after chemoradiation therapy or a colorectal cancer after surgical resection without evidence of residual disease with either microsatellite instability (MSI) or non-hypermutated, microsatellite stability (MSS).

In another preferred embodiment the pancreatic cancer is a pancreatic cancer. In another preferred embodiment, the pancreatic cancer is advanced and/or metastatic pancreatic cancer. In another preferred embodiment, the pancreatic cancer is a resectable pancreatic cancer or amenable to or after chemoradiation or a pancreatic cancer after surgical resection without evidence of residual disease.

In another preferred embodiment, the subject to whom the mRNA molecule is administered has been tumor-typed. In one embodiment, the subject has been tumor-typed for one or more of the KRAS G12D, G12C, G12R, G12V or G13D mutations. In another preferred embodiment, the subject to whom the mRNA is administered has been HLA-typed. In another preferred embodiment, the subject to whom the mRNA is administered has been both tumor-typed and HLA-typed.

In another preferred embodiment, the subject to whom the mRNA molecule is administered has not been tumor-typed. In one embodiment, the subject has been tumor-typed for one or more of the KRAS G12D, G12C, G12R, G12V or G13D mutations. In another preferred embodiment, the subject to whom the mRNA is administered has not been HLA-typed. In another preferred embodiment, the subject to whom the mRNA is administered has not been either tumor-typed or HLA-typed.

The mRNA molecule or the pharmaceutical composition of the invention can be administered parenterally, e.g., subcutaneously, intravenously, intramuscularly, intradermally, intranodally or intraperitoneally. In another embodiment, the mRNA molecule is administered intramuscularly.

According to a further aspect, the invention thus relates to the mRNA molecule or the pharmaceutical composition of the invention, for use as a medicament, in particular for the treatment of cancer. In one preferred embodiment, the mRNA molecule is administered intramuscularly. In another preferred embodiment, the mRNA molecule is administered subcutaneously.

The invention further relates to the use of an mRNA molecule or the pharmaceutical composition of the invention in the manufacture of a medicament for treating cancer.

In another preferred embodiment, the present invention provides a method of treating cancer, comprising the administration of an effective amount of an mRNA molecule of the present invention in simultaneous, separate, or sequential combination with one or more anti-tumor agents. Non-limiting examples of anti-tumor agents include ramucirumab, necitumumab, olaratumab, galunisertib, abemaciclib, regorafenib, erlotinib, crizotinib, cisplatin, carboplatin, dacarbazine, liposomal doxorubicin, docetaxel, cyclophosphamide and doxorubicin, navelbine, eribulin, paclitaxel, nab-paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), FOLFIRINOX (leucovorin, fluorouracil, oxaliplatin and irinotecan), pemetrexed, gemcitabine, cetuximab, an EGFR inhibitor, a Raf inhibitor, a B-Raf inhibitor, a CDK4/6 inhibitor, an idoleamine 2,3-dioxygenase inhibitor, a TGFbeta inhibitor, and a TGFbeta receptor inhibitor.

In another preferred embodiment, the present invention provides a method of treating cancer, comprising the administration of an effective amount of an mRNA molecule of the present invention in simultaneous, separate, or sequential combination with one or more immuno-oncology agents. Non-limiting examples of immuno-oncology agents include nivolumab, ipilimumab, pidilizumab, pembrolizumab, tremelimumab, urelumab, lirilumab, atezolizumab, durvalumab, avelumab and the anti-PD-L1 antibody LY3300054 (the heavy and light chain sequences of which are forth in WO 2017/034916 and US 2017/0058033 as SEQ ID NOs: 10 and 11, respectively).

In another preferred embodiment, the present invention provides a method of treating cancer, comprising the administration of an effective amount of an mRNA molecule of the present invention without simultaneous, separate, or sequential combination with one or more immuno-oncology agents.

In another preferred embodiment, the present invention provides a method of treating cancer, comprising the administration of an effective amount of an mRNA molecule of the present invention in simultaneous, separate, or sequential combination with radiation therapy.

In another preferred embodiment, the present invention provides a method of treating cancer, comprising the administration of an effective amount of an mRNA molecule of the present invention in simultaneous, separate, or sequential combination with surgery.

The present invention also provides an mRNA molecule of the invention for use in therapy.

The present invention also provides an mRNA molecule of the invention for use in treating cancer. In one preferred embodiment, the cancer is a solid tumor cancer that is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, gastric cancer, testicular cancer, thyroid cancer, uterine cancer or urothelial cancer. In another embodiment, the lung cancer is non-small cell lung cancer.

The present invention also provides an mRNA molecule of the invention for the manufacture of a medicament for the treatment of cancer. In one preferred embodiment, the cancer is a solid tumor cancer that is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, gastric cancer, testicular cancer, thyroid cancer, uterine cancer or urothelial cancer. In another embodiment, the lung cancer is non-small cell lung cancer.

In one embodiment, the subject to whom the mRNA molecule or the pharmaceutical composition according to the invention is administered may be a subject with a tumor or cancer disease selected from:

- non-small cell lung cancer (NSCLC), preferably advanced and/or metastatic NSCLC, even more preferably unresectable and/or advanced NSCLC;
- colorectal cancer (CRC), preferably advanced and/or metastatic CRC, even more preferably advanced and/or metastatic hypermutated cancers with either microsatellite instability (MSI) or non-hypermutated, microsatellite stability (MSS); or pancreatic cancer, preferably advanced and/or metastatic pancreatic cancer, even more preferably unresectable and/or advanced pancreatic cancer.

In one embodiment, the subject to whom the mRNA molecule or the pharmaceutical composition according to the invention is administered may be a subject with a tumor or cancer disease preferably as defined herein, more preferably a disease selected from the group consisting of non-small cell lung cancer (NSCLC), preferably advanced and/or metastatic NSCLC, even more preferably unresectable and/or advanced NSCLC, colorectal cancer (CRC), preferably colon cancer and rectal cancer, even more preferably advanced and/or metastatic hypermutated cancers with either microsatellite instability (MSI) or non-hypermutated, microsatellite stability (MSS), or pancreatic cancer, preferably pancreatic adenocarcinoma, who received or receives chemotherapy (e.g. first-line or second-line chemotherapy), radiotherapy, chemoradiation (combination of chemotherapy and radiotherapy), kinase inhibitors, antibody therapy and/or checkpoint modulators (e.g. CTLA4 inhibitors, PD-1 pathway inhibitors), or a subject who has achieved a complete response, partial response, stable disease after having received one or more of the treatments specified above.

In some embodiments, the subject to whom the mRNA molecule or the pharmaceutical composition according to the invention is administered may be a subject with a tumor or cancer disease, preferably as defined herein, more preferably a disease selected from the group consisting of non-small cell lung cancer (NSCLC), preferably advanced and/or metastatic NSCLC, even more preferably unresectable and/or advanced NSCLC, colorectal cancer (CRC), preferably colon cancer and rectal cancer or pancreatic cancer, preferably pancreatic adenocarcinoma, who received or receives a compound conventionally used in any of these diseases as described herein.

In some embodiments, the subject to whom the mRNA molecule or the pharmaceutical composition according to the invention is administered may be a subject with a tumor or cancer disease, preferably NSCLC, more preferably advanced and/or metastatic NSCLC, receiving or having received at least one of the following treatments:

- pre-operatively (neoadjuvant chemotherapy) and/or post-operatively (adjuvant) chemotherapy;
- surgery, or preferably initial surgery for a primary tumor;
- radiation therapy;
- checkpoint modulator monotherapy, preferably targeting CTLA4, PD1 (such as pembrolizumab) or PD-L1 (such as LY3300054);
- combination therapy with interleukins, such as IL-10 or pegylated IL-10;
- combination therapy of checkpoint modulators preferably targeting CTLA4, PD1 (such as pembrolizumab) or PD-L1 (such as LY3300054), and chemotherapy;
- platinum-based chemotherapy, using compounds such as cisplatin or carboplatin, preferably in combination with pemetrexed or gemcitabine;
- compounds that target the EGFR signalling pathway, such as the antibody cetuximab, or tyrosine kinase inhibitors, such as erlotinib, gefitinib, afatinib or osimertinib;
- compounds that acting as an ALK (anaplastic lymphoma kinase) and ROS1 (c-ros oncogene 1) inhibitor, using compounds such as crizotinib; or
- compounds that target the vascular endothelial growth factor (VEGF), such as the antibody bevacizumab.

In some embodiments, the subject to whom the mRNA molecule or the pharmaceutical composition according to the invention is administered may be a subject with a tumor or cancer disease, preferably CRC (colorectal cancer), more preferably advanced and/or metastatic hypermutated cancers with either microsatellite instability (MSI) or non-hypermutated, microsatellite stable (MSS) cancers, receiving or having received at least one of the following treatments:

- surgery, or preferably initial surgery for a primary tumor;
- chemotherapy;
- radiotherapy;
- targeted therapy;
- immunotherapy;
- combination of two or more of surgery, radiotherapy, chemotherapy, targeted therapy, and immunotherapy;
- pre-operatively (neoadjuvant chemotherapy) and/or post-operatively (adjuvant) chemotherapy;
- chemotherapy using compounds such as Fluorouracil (5-FU, Adrucil), Capecitabine (Xeloda), Irinotecan (Camptosar), Oxaliplatin (Eloxatin), Trifluridine/tipiracil (TAS-102, Lonsurf);
- compounds which stop or reduce angiogenesis, such as bevacizumab (Avastin);
- compounds that inhibit the epidermal growth factor receptor (EGFR) such as cetuximab (Erbitux) or panitumumab (Vectibix); or
- compounds which target immune checkpoints, preferably CTLA4, PD1 or PD-L1, such as pembrolizumab (Keytruda) which targets PD-1 receptor, nivolumab (Opdivo), or the anti-PD-L1 antibody LY3300054;
- the combination of nivolumab and ipilimumab (Yervoy);

In some embodiments, the subject to whom the mRNA molecule or the pharmaceutical composition according to the invention is administered may be a subject with a tumor or cancer disease, preferably pancreatic cancer, more preferably advanced and/or metastatic pancreatic cancer, more preferably pancreatic adenocarcinoma, receiving or having received at least one of the following treatments:

- surgery, or preferably initial surgery for a primary tumor;
- radiotherapy;
- chemotherapy;
- combination of surgery, radiotherapy, and chemotherapy;
- combination therapy with interleukins, such as IL-10 or pegylated IL-10;
- pre-operatively (neoadjuvant) and/or post-operatively (adjuvant) chemotherapy;
- chemotherapy, using compounds such as gemcitabine or Fluorouracil (5-FU), irinotecan, oxaliplatin or nab-paclitaxel;
- compounds that target the EGFR signalling pathway, using compounds such as erlotinib;
- the combination of gemcitabine with erlotinib;
- compounds supporting the digestive system, using compounds such as proton-pump inhibitors, H2 antagonists or metoclopramide; or
- compounds targeting immune checkpoints, such as pembrolizumab, nivolumab, ipilimumab, or LY3300054.

The mRNA molecule or pharmaceutical compositions, or kit of the invention may be administered to a subject in need by a regimen that one of ordinary skill in the art would determine to be clinically appropriate.

In one embodiment, one or more mRNA molecules of the invention is/are administered to a subject at a dosage of about 1, 5, 10, 20, 30, 40, 100, 300 or 1000 μg. In another embodiment, one or more mRNA molecules of the invention is/are administered to a subject at a dosage of about 1 μg. In another embodiment, one or more mRNA molecules of the invention is/are administered to a subject at a dosage of about 5 μg. In another embodiment, one or more mRNA molecules of the invention is/are administered to a subject at a dosage of about 10 μg. In another embodiment, one or more mRNA molecules of the invention is/are administered to a subject at a dosage of about g. In another embodiment, one or more mRNA molecules of the invention is/are administered to a subject at a dosage of about 40 μg. In another embodiment, one or more mRNA molecules of the invention is/are administered to a subject at a dosage of about 100 μg. In another embodiment, one or more mRNA molecules of the invention is/are administered to a subject at a dosage of about 300 μg. In another embodiment, one or more mRNA molecules of the invention is/are administered to a subject at a dosage of about 1000 μg. In another embodiment, one or more mRNA molecules of the invention is/are administered in combination with an immune-oncology agent, such as an anti-PD-1 antibody, an anti-PD-L1 antibody (such as LY3300054), or a pegylated IL-10 molecule.

In one embodiment, one or more mRNA molecules of the invention is/are administered to a subject for a duration of 3, 4, 5, 6, 12, 18 or 24 months. In another embodiment, one or more mRNA molecules of the invention is/are administered to a subject for a duration of 3 months. In another embodiment, one or more mRNA molecules of the invention is/are administered to a subject for a duration of 4 months. In another embodiment, one or more mRNA molecules of the invention is/are administered to a subject for a duration of 5 months. In another embodiment, one or more mRNA molecules of the invention is administered to a subject for up to 6 months. In another embodiment, one or more mRNA molecules of the invention is/are administered in combination with an immune-oncology agent, such as an anti-PD-1 antibody, an anti-PD-L1 antibody (LY3300054), or a pegylated IL-10 molecule.

In another embodiment, one or more mRNA molecules of the invention is/are administered to a subject at a dosage of about 1, 5, 10, 20, 30, 40, 100, 300 or 1000 μg, and for a duration of a duration of 3, 4, 5 or 6 months.

The present invention also provides an mRNA molecule encoding an amino acid sequence comprising a CTLA4 signal peptide, a KRAS variant peptide, a PADRE-derived T helper epitope sequence, and a CTLA4 immune response activating signal transduction protein sequence particularly preferably for use as a medicament. In a preferred embodiment, the KRAS variant peptide comprises 29 contiguous amino acid residues of KRAS variant peptide sequence.

The present invention also provides an mRNA molecule comprising mRNA sequence encoding an amino acid sequence comprising a CTLA4 signal peptide, a KRAS variant peptide, a PADRE-derived T helper epitope sequence, and a CTLA4 immune response activating signal transduction protein sequence for use in the treatment of cancer, wherein the cancer is preferably a solid tumor cancer that is particularly preferably selected from bladder cancer, breast cancer, cervical cancer, colorectal cancer, endometrial cancer, head and neck cancer, liver cancer, lung cancer, non-small cell lung cancer, melanoma, ovarian cancer, pancreatic cancer, prostate cancer, renal cancer, gastric cancer, testicular cancer, thyroid cancer, or uterine cancer. In a preferred embodiment, the KRAS variant peptide comprises 29 contiguous amino acid residues of KRAS variant peptide sequence.

In a further preferred aspect, the present invention provides a kit comprising the mRNA molecule or the pharmaceutical composition of the invention, and optionally a liquid vehicle and/or optionally technical instructions with information on the appropriate administration and dosage of the mRNA molecule or the composition.

Although the present invention is described in detail below, it is to be understood that this invention is not limited to the particular methodologies, protocols and reagents described herein as these may vary. It is also to be understood that the terminology used herein is not intended to limit the scope of the present invention. Unless defined otherwise herein, all technical and scientific terms used herein have the same meanings as commonly understood by one of ordinary skill in the art.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The term "about" in relation to a numerical value x means x±10%.

In the present invention, if not otherwise indicated, different features of alternatives and embodiments may be combined with each other.

The term "HLA" refers to human leukocyte antigen, which is a cell surface molecule that presents variant peptides to the T-cell receptor. The term "HLA-typed subject" refers to a subject for whom the human leukocyte antigen profile in that subject has been determined. Methods for determining HLA type are well known to those of ordinary skill in the art, as shown, for example, in Rajalingam R, et al., *Molecular Diagnostics, Techniques and Applications for the Clinical Laboratory* 2010, pages 367-379, Academic Press; and Choo S Y, *Yonsei Medical Journal* 48: 11 (2007). Non-limiting methods for determining HLA type include cellular typing, gene sequencing, phenotyping, and haplotyping. The terms "HLA-typed subject" and "human leukocyte antigen-typed subject" are synonymous.

A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

As used herein, RNA means ribonucleic acid, and mRNA means messenger RNA. The mRNA of the invention may be prepared using any method known in the art, including chemical synthesis such as e.g. solid phase RNA synthesis, as well as in vitro methods, such as RNA in vitro transcription reactions. In a preferred embodiment, the artificial RNA, preferably the mRNA is obtained by RNA in vitro transcription. Accordingly, in one embodiment, the RNA of the invention is an in vitro transcribed RNA, preferably an in vitro-transcribed mRNA.

The term "tumor-typed subject" refers to a subject in whom the type of KRAS mutation(s) exhibited by the subject's tumor have been determined. In one embodiment, the subject has been tumor-typed for one or more of the KRAS G12D, G12C, G12R, G12V or G13D mutations. Methods of KRAS tumor typing are known to those of ordinary skill in the art, e.g., see Hunter J D, et al., *Mol. Cancer Research* 13: 1325 (2015); Prior I A, et al., *Cancer Research* 71: 2457 (2012); Tan C and D Xiang, *World J. Gastroenterol.* 18: 5171 (2012).

The term "treatment" or "treating" of a disease includes preventing or protecting against the disease (that is, causing the clinical symptoms not to develop); inhibiting the disease (i.e., arresting or suppressing the development of clinical symptoms; and/or relieving the disease (i.e., causing the regression of clinical symptoms).

In a preferred embodiment, the term "subject" refers to a human.

The present invention is based, in part, on finding that mRNA encoding KRAS-mutant peptides can be taken up, and the encoded peptides processed, and presented by antigen presenting cells (APCs) at levels sufficient to be recognized by pre-existing T cells, which can distinguish between mutant and wild type RAS sequence. T cell interaction leads to an amplification of the mutant RAS-specific T cell population which subsequently can seek out and kill RAS-mutant tumor cells. This invention uses a signal sequence from a "targeting" protein such as cytotoxic T-lymphocyte protein 4 (CTLA4), which is known as a "fast recycling" protein that is readily and recurrently internalized to enter the endosomal pathways, which intersect MHC class I and in particular also MHC class II pathways. By fusing KRAS-derived antigens to the "targeting" sequences, the antigens can be routed to MHC class I and MHC class II processing compartments—independently of the target cell type—and effect their expression and presentation of MHC I and in particular MHC II.

To that end, mRNA molecules encoding KRAS-derived antigens/epitopes are fused to nucleic acid sequences encoding suitable "targeting" sequences. The "targeting" sequences typically comprise or consist of the full-length amino acid sequence of a protein, or preferably its transmembrane (and optionally cytoplasmic) domains, preferably together with a suitable signal peptide. By fusing nucleic acid sequences encoding KRAS-derived antigens to such "targeting" sequences, the KRAS-derived antigens/epitopes are preferably localized to the plasma membrane, and are recycled to cellular compartments where the MHC class I and II processing and loading take place, like the endoplasmic reticulum, endosomes or the lysosome. The targeting strategy presented herein exploits the fast-recycling characteristics conferred by amino acid sequences (in particular transmembrane domains) derived from the group of immune-response activating signal transduction ($IRST_{epm}$) proteins residing in the plasma membrane of immune cells. By effectively routing variant peptides or proteins to the plasma membrane and effecting their anchorage therein, and subsequent recycling to cellular compartments intersecting with the MHC processing and loading pathways via the fused $IRST_{epm}$-derived protein domains, the presentation of encoded antigens/epitopes by MHC class I and MHC class II in recipient cells, and therefore the induction of antigen-specific immune responses against the immunogenic epitopes or whole antigens by nucleic acid-based vaccines, is preferably increased. The targeting approach presented herein therefore exploits the common pathways of fast-recycling of membrane-bound $IRST_{epm}$-proteins, instead of using state-of-the-art approaches of directing the translated variant proteins or peptides directly to endosomal/lysosomal compartments via the fusion of different trafficking sequences.

The term "immune-response-activating signal transduction" refers to the cascade of processes by which a signal interacts with a receptor, causing a change in the level or activity of a second messenger or other downstream target, and ultimately leading to activation or perpetuation of an immune response.

As used herein, the term "(protein/amino acid sequence) variant" in general refers to "sequence variants", i.e. proteins or (poly-)peptides comprising an amino acid sequence that differs in at least one amino acid residue from a reference (or "parent") amino acid sequence of a reference (or "parent") protein or (poly-)peptide. "Variant" proteins/(poly-)peptides comprise, in their amino acid sequence, at least one amino acid mutation, substitution, insertion or deletion as compared to their respective reference sequence.

The term "KRAS-derived variant peptide or protein" refers to a (poly-)peptide comprising, capable of providing at least one (functional) KRAS epitope or neoepitope. A KRAS variant peptide or protein is one that exhibits a mutation of at least one amino acid residue, compared to the wild-type KRAS peptide or protein sequence. The KRAS G12C, G12D, G12V, G12R and G13D variants are examples of KRAS variants that can be found in a KRAS variant peptide.

KRAS-derived variant peptides are joined to selected domains or full-length proteins derived from the fast-recycling immune-response activating signal transduction protein CTLA4. A signal peptide and transmembrane domain can be included to optimize transport to and anchorage on the external site of the plasma membrane. Additionally, a suitable linker can be included to facilitate the presentation of immunogenic peptides by the MHC class I and class II molecules. T helper cell epitopes can included to increase the induction of antigen-specific immune responses against the encoded KRAS-derived epitopes.

The terms "epitope" "neo-epitope" refer to a part or fragment of a variant peptide or protein (antigen) that is recognized by the immune system. Neoepitopes can be used as a disease-specific target, from which a diseased tissue cannot easily escape immune surveillance, which in the case of cancer will result in enhanced tumor control. Epitopes may comprise from about 5 to about 20 or even more amino acids. Epitopes may be "conformational" (or "discontinuous"), i.e. composed of discontinuous sequences of the amino acids of the variant peptide or protein that they are derived from, but brought together in the three-dimensional structure of e.g. a MHC-complex, or "linear", i.e. consist of a continuous sequence of amino acids of the variant peptides or proteins that they are derived from.

According to a preferred embodiment of the invention, the KRas-derived variant peptide or protein comprises or consists of mutant KRAS variants, comprising neoepitopes derived from mutant KRas. Particularly preferred are neoepitopes derived from one or more of the mutant KRas variants G12C, G12D, G12V, G12R and G13D.

According to a particularly preferred embodiment of the invention the mRNA molecule further encodes at least one signal peptide, particularly preferred from CTLA4, and particularly CTLA4 (NM_005214.4) amino acid residues 1-35 (SEQ ID NO: 3), which can be encoded by any one of the nucleic acid sequences of SEQ ID NOS: 4, 5, 6 or 7.

Accordingly, the mRNA molecule of the invention preferably encodes at least one signal peptide preferably comprising or consisting of an amino acid sequence as defined by SEQ ID NO: 3 or a fragment, derivative or variant thereof. Preferably, the mRNA sequence encoding the CTLA4-derived signal peptide comprises or consists of a nucleic acid sequence as set forth in any one of SEQ ID NOs: 4, 5, 6 or 7, wherein SEQ ID NO. 5 is particularly preferred.

According to a particularly preferred embodiment of the invention the mRNA molecule further encodes at least one transmembrane domain, or portion thereof, particularly preferred from CTLA4, and particularly CTLA4 amino acid residues 162-223 (SEQ ID NO: 42, which can be encoded by any one of the nucleic acid sequences of SEQ ID NOSNOs: 43, 44, 45, 46, or 47. According to preferred embodiments, the at least one coding region of the mRNA molecule according to the invention further encodes at least one linker.

The term "linker" refers to peptide linkers, i.e. typically short (i.e. comprising 1-150 amino acids, preferably 1-50 amino acids, more preferably 1 to 20 amino acids, and even more preferably, 15 amino acids), linear amino acid sequences connecting or linking two polypeptide sequences. Preferably, the linker(s) is/are non-immunogenic, i.e. do not trigger an immune response. Linkers may be employed to connect or link at least two components of the variant fusion protein encoded by the mRNA molecule of the invention. The coding region of the mRNA molecule according to the invention may encode at least one linker, or a plurality of at least 2, 3, 4, 5, 6, 7, 8, 9 or 10 identical or different linkers, as described herein. In case a plurality of linkers is encoded by the mRNA molecule it is particularly preferred that the linkers differ in their amino acid sequence and/or nucleic acid sequence encoding the respective linkers.

Nonlimiting examples of linkers are disclosed in WO 2002/014478, WO 2001/008636, WO 2013/171505, WO 2008/017517 and WO 1997/047648.

According to preferred embodiments, the mRNA molecule of the invention encodes, in its at least one coding region, at least one linker, which is preferably a non-immunogenic linker, preferably comprising or consisting of an amino acid sequence according to SEQ ID NO: 35.

Accordingly, the mRNA molecule of the invention preferably comprises, in its at least one coding region, at least one nucleic acid sequence comprising or consisting of a nucleic acid sequence according to any one of SEQ ID NOs: 36, 37, 38, 39, 40 or 41, and preferably any one of SEQ ID NOs: 37, 38 or 39.

In a preferred embodiment of the invention the mRNA molecule, further encodes at least one T helper epitope. The term "T helper epitope" refers to a variant determinant capable of binding to MHC molecules, preferably MHC Class II molecules, thereby being recognized by $CD4^+$ T helper (Th) cells. Thus, T helper epitopes may advantageously be used to induce or enhance $CD4^+$ Th cell responses, CTL responses (preferably including increased cell-mediated immunity and enhanced, e.g., anti-tumor immune responses).

"PADRE" (pan DR epitope peptides") as described in WO 95/07707 and in Alexander J et al., 1994, Immunity 1: 751-761, with or without carrying D-amino acids in the C- and N-termini, are preferred T helper epitopes in the context of the present invention.

According to preferred embodiments, the mRNA molecule of the invention encodes, in its at least one coding region, at least one T helper epitope, preferably SEQ ID NO: 33, and is preferably encoded by the RNA of SEQ ID NO: 34.

The mRNA molecule according to the invention may be mono-, bi-, or multicistronic. "Bi- or multicistronic" RNAs typically comprise two (bicistronic) or more (multicistronic) open reading frames (ORF).

According to preferred embodiments, the mRNA molecule of the invention may be "sequence-modified", i.e. may comprise at least one sequence modification as described below.

According to preferred embodiments, the mRNA molecule of the invention, may be modified, and thus stabilized, by modifying its guanosine/cytosine (G/C) content, preferably by modifying the G/C content of the at least one coding sequence.

In one preferred embodiment, the A/U content in the environment of the ribosome binding site of the mRNA molecule of the invention is increased compared to the A/U content in the environment of the ribosome binding site of its respective wild-type mRNA. This modification (an increased A/U content around the ribosome binding site) can increase the efficiency of ribosome binding to the mRNA molecule. An effective binding of the ribosomes to the ribosome binding site (Kozak sequence) in turn has the effect of an efficient translation of the mRNA molecule of the invention.

In one preferred embodiment, the mRNA molecule of the invention may be modified with respect to potentially destabilizing sequence elements. Particularly, the coding sequence and/or the 5' and/or 3' untranslated region of the mRNA molecule may be modified compared to the respective wild-type mRNA (or the other wild-type nucleic acid) such that it contains no destabilizing sequence elements, the encoded amino acid sequence of the modified mRNA molecule preferably not being modified compared to its respective wild-type mRNA.

In one preferred embodiment, mRNA molecules as defined herein, may be modified by the addition of a so-called "5' cap" structure, which preferably stabilizes the mRNA molecule in vivo, as described herein. Further, mRNA comprising a cap structure is characterized by increased translation efficiency in vivo and reduced innate immune stimulation. A "5'-cap" is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an mRNA. A 5'-cap structure (e.g. m7GpppN) is the 5'-cap structure, which naturally occurs in mRNA transcribed by polymerase II and is therefore preferably not considered as modification comprised in a "modified" mRNA in this context. Accordingly, the term "modified" mRNA molecule, may comprise a m7GpppN, ARCA Cap, Cap1 as 5'-cap structure and additionally at least one further modification as defined herein.

The 5'-cap may be added using a 5'-5'-triphosphate linkage (e.g. triphosphate linkage underlined: m7<u>GpppN</u>). Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety, cap1 (methylation of the ribose of the adjacent nucleotide of m7G), cap2 (additional methylation of the ribose of the 2nd nucleotide downstream of the m7G), cap3 (additional methylation of the ribose of the 3rd nucleotide downstream of the m7G), cap4 (methylation of the ribose of the 4th nucleotide downstream of the m7G), ARCA (anti-reverse cap analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine. These modified 5'-cap structures may be regarded as at least one “modification” in the context of the present invention.

Accordingly, in a preferred embodiment, the mRNA, of the invention may comprise a 5'-cap structure, or a modified 5' cap structure. Preferably, the mRNA molecule, may comprise a 5'-Cap structure selected from m7GpppN, ARCA Cap or Cap1.

In a preferred embodiment, the 5'-cap structure may suitably be added co-transcriptionally using cap-analogues as defined herein in an RNA in vitro transcription reaction as defined herein. Preferred cap-analogues in the context of the invention are m7G(5')ppp(5')G (m7G) or 3'-O-Me-m7G(5') ppp(5')G. Further preferred cap-analogues in the context of the invention are m7G(5')ppp(5')(2'OMeA)pG or m7G(5') ppp(5')(2'OMeG)pG to co-transcriptionally generate cap1 structures (e.g. CleanCap®).

In one preferred embodiment, the mRNA molecule comprises a cap1 structure, wherein the cap1 structure is obtainable by co-transcriptional capping. A cap1 structure comprising mRNA has several advantageous features in the context of the invention, including an increased translation efficiency and a reduced stimulation of the innate immune system.

According to a further preferred embodiment, the mRNA molecule of the invention may contain a poly(A) sequence. A “poly(A) sequence”, also called “poly(A) tail” or “3'-poly (A) tail”, is typically understood to be a sequence of adenosine nucleotides, e.g., of up to about 400 adenosine nucleotides, e.g. from about 20 to about 400, preferably from about 50 to about 400, more preferably from about 50 to about 300, even more preferably from about 50 to about 250, most preferably from about 60 to about 250 adenosine nucleotides. As used herein, a poly(A) sequence may also comprise about 10 to 200 adenosine nucleotides, preferably about 10 to 100 adenosine nucleotides, more preferably about 40 to 80 adenosine nucleotides or even more preferably about 50 to 70 adenosine nucleotides. A poly(A) sequence is typically located at the 3'end of an RNA, in particular a mRNA.

In one preferred embodiment, the mRNA molecule of the invention may contain at its 3' terminus a poly(A) tail of typically about 10 to 200 adenosine nucleotides, preferably about 10 to 100 adenosine nucleotides, more preferably about 40 to 80 adenosine nucleotides or even more preferably about 50 to 70 adenosine nucleotides.

In a preferred embodiment, the poly(A) sequence, suitable located at the 3' terminus (e.g. downstream of the 3' UTR as defined herein), comprises 10 to 500 adenosine nucleotides, 10 to 200 adenosine nucleotides, 40 to 200 adenosine nucleotides, 40 to 150 adenosine nucleotides or 30 to 150 adenosine nucleotides. In a particularly preferred embodiment, the poly(A) sequence comprises about 64 adenosine nucleotides. In further particularly preferred embodiments, the poly(A) sequence comprises about 75 adenosine nucleotides. In another preferred embodiment, the poly(A) sequence comprises about 100 adenosine nucleotides.

According to a preferred embodiment, the mRNA molecule of the invention may contain a poly(C) tail on the 3' terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides. In a particularly preferred embodiment, the poly(C) sequence comprises about 30 cytosine nucleotides.

The term “poly(C) sequence” as used herein will be recognized and understood by the person of ordinary skill in the art, and are for example intended to be a sequence of cytosine nucleotides, typically located at the 3'-end of an RNA, of up to about 200 cytosine nucleotides. In the context of the present invention, a poly(C) sequence may be located within an mRNA or any other nucleic acid molecule, such as in a DNA serving as template for the generation of an RNA, preferably an mRNA, e.g., by transcription the DNA template (e.g., plasmid DNA or PCR product).

In particularly preferred embodiments, the coding RNA of the invention does comprise a poly(A) sequence as defined herein, preferably 100 adenosine nucleotides located (exactly) at the 3' terminus, and does not comprise a poly(C) sequence.

According to a preferred embodiment, the mRNA molecule of the invention may comprise at least one 5'- and/or 3'-UTR element. A “UTR element” comprises or consists of a nucleic acid sequence, which is derived from the 5'- or 3'-UTR of any naturally occurring gene or which is derived from a fragment, a homolog or a variant of the 5'- or 3'-UTR of a gene.

In one preferred embodiment, the coding region of the mRNA molecule according to the invention may be located downstream of a 5' UTR element as defined herein and/or upstream of a 3'UTR element as defined herein. Preferably, if the mRNA molecule according to the invention comprises at least one 3' UTR element and at least one 5' UTR element, the coding region may be located between the at least one 5' UTR element and the at least one 3' UTR element.

Preferably, the mRNA molecule of the invention may comprise a 3' UTR element, which is derived from a gene, preferably an alpha-globin gene. Particularly preferred is a 3' UTR element of SEQ ID NO: 1.

In a preferred embodiment, the mRNA molecule of the first aspect of the invention comprises at least one histone stem-loop.

The term “histone stem-loop” as used herein will be recognized and understood by the person of ordinary skill in the art, and is e.g. intended to refer to nucleic acid sequences that are predominantly found in histone mRNAs. Particularly prefer histone stem-loop sequences are encoded by SEQ ID NOS: 2. In a preferred embodiment the mRNA molecule of the invention comprises or consists of RNA sequences set forth in any one of SEQ ID NOS: 58-72. In a particularly preferred embodiment the mRNA molecule of the invention comprises or consists of RNA sequences set forth in any one of SEQ ID NOs: 63, 64, 65, 66 or 67. In embodiments, the coding RNA of the invention comprises a 3'-terminal sequence element. Said 3'-terminal sequence element comprises a poly(A) sequence and a histone-stem-loop sequence, wherein said sequence element is located at the 3' terminus (exactly at the 3' terminus) of the RNA of the invention. In a particularly preferred embodiment the mRNA molecule of the invention comprises or consists of RNA sequences set forth in any one of SEQ ID NOs: 73-112

According to a preferred embodiment, the mRNA molecule of the invention may be provided in a "naked" form, i.e. without being associated with any further vehicle, transfection or complexation agent for increasing the transfection efficiency and/or the immunostimulatory properties of the mRNA molecule or of any other nucleic acid.

In one preferred embodiment, the mRNA molecule of the invention may be provided in a composition. In further aspects, the present invention thus provides a composition comprising at least one mRNA molecule, according to the invention, and optionally a carrier. Therein, the at least one mRNA molecule may be associated with a suitable vehicle, transfection or complexation agent for increasing the transfection efficiency and/or the immunostimulatory properties of the mRNA molecule. Optionally, the composition may be a pharmaceutical composition, as described in further detail below.

The mRNA molecule of the present invention can be complexed or associated with one or more (poly)cationic compounds, preferably with (poly-)cationic polymers, (poly-)cationic peptides or proteins, e.g. protamine, (poly-) cationic polysaccharides and/or [(poly-)cationic]lipids. The other nucleic acid as described herein may also be complexed with lipids, thereby forming lipoplexes, liposomes or preferably lipid nanoparticles (LNPs).

According to a preferred embodiment, the mRNA molecule of the pharmaceutical composition may be complexed with one or more lipids, thereby forming lipoplexes, liposomes or preferably lipid nanoparticles (LNPs).

The mRNA molecule of the pharmaceutical composition may thus be provided in the form of a lipid-based formulation. The term "lipid nanoparticle", also referred to as "LNP", is not restricted to any particular morphology, and include any morphology generated when a cationic lipid and optionally one or more further lipids are combined, e.g. in an aqueous environment and/or in the presence of RNA. Preferably, the term lipid nanoparticle (LNP) is understood as comprising the terms "liposome", "lipid complex", and "lipoplex".

It is also envisaged that any other nucleic acid as described herein in the context of the present invention, e.g. immunostimulatory nucleic acids or the like, may be complexed with one or more lipids, thereby forming lipoplexes, liposomes or preferably lipid nanoparticles (LNPs) as described in the context of the invention. Furthermore, lipoplexes, liposomes or preferably lipid nanoparticles (LNPs) may comprise the mRNA molecules, of the invention, and further any other nucleic acid as described herein.

The mRNA molecule of the pharmaceutical composition may be complexed or associated with lipids (in particular cationic and/or neutral lipids) to form one or more lipid nanoparticles. Preferably, lipid nanoparticles (LNPs) comprise: (a) at least one mRNA molecule of the invention, (b) a cationic lipid, (c) an aggregation reducing agent (such as polyethylene glycol (PEG) lipid or PEG-modified lipid), (d) optionally a non-cationic lipid (such as a neutral lipid), and (e) optionally, a sterol. In particular, LNPs may comprise, in addition to the at least one mRNA molecule of the invention, (i) at least one cationic lipid; (ii) a neutral lipid; (iii) a sterol, e.g., cholesterol; and (iv) a PEG-modified lipid, preferably in a molar ratio of about 20-60% cationic lipid: 5-25% neutral lipid: 25-55% sterol; 0.5-15% PEG-lipid.

LNPs typically comprise a cationic lipid and one or more excipient selected from neutral lipids, charged lipids, steroids and polymer conjugated lipids (e.g. PEGylated lipid). The mRNA molecule of the invention may be encapsulated in the lipid portion of the LNP or an aqueous space enveloped by some or the entire lipid portion of the LNP. The mRNA molecule of the invention may also be associated and complexed with the LNP. An LNP may comprise any lipid capable of forming a particle to which the nucleic acids are attached, or in which the one or more nucleic acids are encapsulated. Preferably, the LNP comprises one or more cationic lipids, and one or more stabilizing lipids. Stabilizing lipids include neutral lipids and PEGylated lipids.

The cationic lipid of an LNP may be cationisable, i.e. it becomes protonated as the pH is lowered below the pK of the ionizable group of the lipid, but is progressively more neutral at higher pH values. At pH values below the pK, the lipid is then able to associate with negatively charged nucleic acids. In certain embodiments, the cationic lipid comprises a zwitterionic lipid that assumes a positive charge on pH decrease.

(i) Cationic Lipids

LNPs may include any cationic lipid suitable for forming a lipid nanoparticle. Preferably, the cationic lipid carries a net positive charge at about physiological pH.

The cationic lipid may be an amino lipid. As used herein, the term "amino lipid" is meant to include those lipids having one or two fatty acid or fatty alkyl chains and an amino head group (including an alkylamino or dialkylamino group) that may be protonated to form a cationic lipid at physiological pH.

The cationic lipid may be, for example, N,N-dioleyl-N,N-dimethylammonium chloride (DODAC), N,N-distearyl-N,N-dimethylammonium bromide (DDAB), 1,2-dioleoyltrimethyl ammonium propane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-ylinolenyloxy-N,N-dimethylaminopropane (7-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethyl-aminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta-[d][1,3]dioxol-5-amine, (6Z,9Z,28Z,31Z)-heptatriaconta-6,9,28,31-tetraen-19-yl 4-(dimethylamino) butanoate (MC3), 1,1'-(2-(4-(2-((2-(bis(2-hydroxydodecyl) amino)ethyl)(2-hydroxydodecyl)amino)ethyl)piperazin-1-yl)ethylazanediyl)-didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28,31-tetraen-19-yl 4-(di-methylamino)

butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31Z)-heptatriaconta-6,9,28,31-tetraen-19-yloxy)-N,N-dimethyl-butan-1-amine (MC4 Ether), or any combination of any of the foregoing.

Other cationic lipids include, but are not limited to, N,N-distearyl-N,N-dimethylammonium bromide (DDAB), 3P—(N—(N',N'-dimethylaminoethane)-carbamoyl)cholesterol (DC-Chol), N-(1-(2,3-dioleyloxy)propyl)-N-2-(spermine-carboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al, PNAS, 107(5), 1864-69, 2010. In some embodiments, the lipid is selected from the group consisting of 98N12-5, C12-200, and ckk-E12.

In one embodiment, the further cationic lipid is an amino lipid. Representative amino lipids include, but are not limited to, 1,2-dilinoleyoxy-3-(dimethylamino)acetoxypropane (DLin-DAC), 1,2-dilinoleyoxy-3morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3dimethylaminopropane (DLin-2-DMAP), 1,2-dilinoleyloxy-3-trimethylaminopropane chloride salt (DLin-TMA·Cl), 1,2-dilinoleoyl-3-trimethylaminopropane chloride salt (DLin-TAP·Cl), 1,2-dilinoleyloxy-3-(N-methylpiperazino)propane (DLin-MPZ), 3-(N,Ndilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA), 2,2-dilinoleyl-4-(2-dimethylaminoethyl)-[1,3]-dioxolane (DLin-KC2-DMA); dilinoleyl-methyl-4-dimethylaminobutyrate (DLin-MC3-DMA); MC3 (US20100324120).

In one embodiment, the at least one mRNA molecule may be formulated in an aminoalcohol lipidoid. Aminoalcohol lipidoids which may be used in the present invention may be prepared by the methods described in U.S. Pat. No. 8,450,298. Suitable (ionizable) lipids can also be the compounds as disclosed in Tables 1, 2 and 3 and as defined in claims 1-24 of WO2017/075531A1.

In another embodiment, ionizable lipids can also be the compounds as disclosed in WO2015/074085A1 (i.e. ATX-001 to ATX-032 or the compounds as specified in claims 1-26), U.S. Appl. Nos. 61/905,724 and 15/614,499 or U.S. Pat. Nos. 9,593,077 and 9,567,296.

In that context, any lipid derived from generic Formula (LNP-I)

(LNP-I)

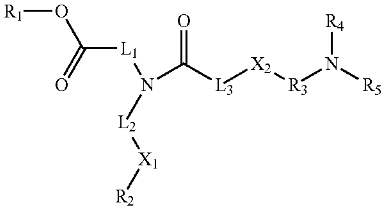

wherein, $R_1$ and $R_2$ are the same or different, each a linear or branched alkyl consisting of 1 to 9 carbons, an alkenyl or alkynyl consisting of 2 to 11 carbons, $L_1$ and $L_2$ are the same or different, each a linear alkylene or alkenylene consisting of 5 to 18 carbons, or forming a heterocycle with N, $X_1$ is a bond, or is —CO—O— whereby $-L_2$-CO—O—$R_2$ is formed, $X_2$ is S or O, $L_3$ is a bond or a linear or branched alkylene consisting of 1 to 6 carbons, or forming a heterocycle with N, $R_3$ is a linear or branched alkylene consisting of 1 to 6 carbons, and $R_4$ and $R_5$ are the same or different, each hydrogen or a linear or branched alkyl consisting of 1 to 6 carbons; or a pharmaceutically acceptable salt thereof may be suitably used.

In other embodiments, suitable cationic lipids can also be the compounds as disclosed in WO2017/117530A1 (i.e. lipids 13, 14, 15, 16, 17, 18, 19, 20, or the compounds as specified in the claims).

In that context, any lipid derived from generic Formula (LNP-II)

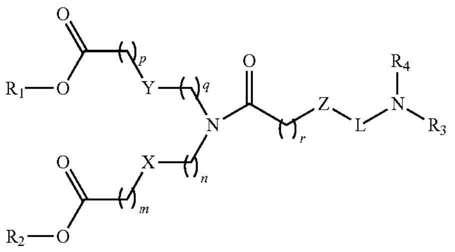

wherein

X is a linear or branched alkylene or alkenylene, monocyclic, bicyclic, or tricyclic arene or heteroarene;

Y is a bond, an ethene, or an unsubstituted or substituted aromatic or heteroaromatic ring; Z is S or 0;

L is a linear or branched alkylene of 1 to 6 carbons;

$R_3$ and $R_4$ are independently a linear or branched alkyl of 1 to 6 carbons;

$R_1$ and $R_2$ are independently a linear or branched alkyl or alkenyl of 1 to 20 carbons; r is 0 to 6; and m, n, p, and q are independently 1 to 18;

wherein when n=q, m=p, and $R_1$=$R_2$, then X and Y differ;

wherein when X=Y, n=q, m=p, then $R_1$ and $R_2$ differ;

wherein when X=Y, n=q, and $R_1$=$R_2$, then m and p differ; and wherein when X=Y, m=p, and $R_1$=$R_2$, then n and q differ;

or a pharmaceutically acceptable salt thereof.

In preferred embodiments, a lipid may be used derived from Formula (LNP-II), wherein, X is a bond, linear or branched alkylene, alkenylene, or monocyclic, bicyclic, or tricyclic arene or heteroarene; Y is a monocyclic, bicyclic, or tricyclic arene or heteroarene; Z is S or O; L is a linear or branched alkylene of 1 to 6 carbons; $R_3$ and $R_4$ are independently a linear or branched alkyl of 1 to 6 carbons; $R_1$ and $R_2$ are independently a linear or branched alkyl or alkenyl of 1 to 20 carbons; r is 0 to 6; and m, n, p, and q are independently 1 to 18; or a pharmaceutically acceptable salt thereof may be suitably used.

In preferred embodiments, ionizable lipids may also be selected from the lipid compounds disclosed in PCT application PCT/EP2017/077517 (i.e. lipid compounds derived form Formula I, II, and III of PCT/EP2017/077517, or lipid compounds as specified in Claims 1 to 12 of PCT/EP2017/077517), the disclosure of PCT/EP2017/077517. In that context, lipid compounds disclosed in Table 7 of PCT/EP2017/077517 (e.g. lipid compounds derived from Formula I-1 to I-41) and lipid compounds disclosed in Table 8 of PCT/EP2017/077517 (e.g. lipid compounds derived from Formula II-1 to II-36) may be suitably used in the context of the invention. Accordingly, Formula I-1 to Formula I-41 and Formula II-1 to Formula II-36 of PCT/EP2017/077517, and the specific disclosure relating thereto.

In particularly preferred embodiments, a suitable lipid may be a cationic lipid according to Formula (LNP-III)

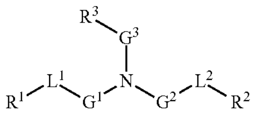

or a pharmaceutically acceptable salt, tautomer, prodrug or stereoisomer thereof, wherein, $R^1$, $R^2$, $R^3$, $L^1$, $L^2$, $G^1$, $G^2$, and $G^3$ are as below.

Formula (LNP-III) is further defined in that:

one of $L^1$ or $L^2$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, —$NR^aC$(═O)$NR^a$—, —OC(═O)$NR^a$— or —$NR^aC$(═O)O—, and the other of $L^1$ or $L^2$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, —$NR^aC$(═O)$NR^a$—, —OC(═O)$NR^a$— or —$NR^aC$(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(═O)$OR^4$, —OC(═O)$R^4$ or —$NR^5C$(═O)$R^4$;

$R^4$ is $C_1$-$C_{12}$ alkyl;

$R^5$ is H or $C_1$-$C_6$ alkyl; and x is 0, 1 or 2.

In some of the foregoing embodiments of Formula (LNP-III), the lipid has one of the following structures (LNP-IIIA) or (LNP-IIIB):

(LNP-IIIA)

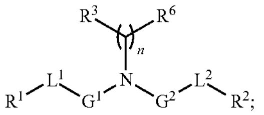

-continued (LNP-IIIB)

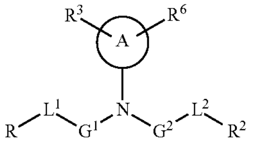

wherein:

A is a 3 to 8-membered cycloalkyl or cycloalkylene ring;

$R^6$ is, at each occurrence, independently H, OH or $C_1$-$C_{24}$ alkyl; n is an integer ranging from 1 to 15.

In some of the foregoing embodiments of Formula (LNP-III), the lipid has structure (LNP-IIIA), and in other embodiments, the lipid has structure (LNP-IIIB).

In other embodiments of Formula (LNP-III), the lipid has one of the following structures (LNP-IIIC) or (LNP-IIID):

(LNP-IIIC)

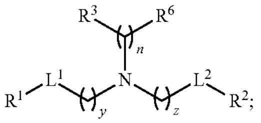

(LNP-IIID)

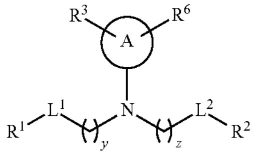

wherein y and z are each independently integers ranging from 1 to 12.

In any of the foregoing embodiments of Formula (LNP-III), one of $L^1$ or $L^2$ is —O(C═O)—. For example, in some embodiments each of $L^1$ and $L^2$ are —O(C═O)—. In some different embodiments of any of the foregoing, $L^1$ and $L^2$ are each independently —(C═O)O— or —O(C═O)—. For example, in some embodiments each of $L^1$ and $L^2$ is —(C═O)O—.

In preferred embodiments, the cationic lipid of the LNP is a compound of Formula (LNP-III), wherein:

$L^1$ and $L^2$ are each independently —O(C═O)— or (C═O)—O—;

$G^3$ is $C_1$-$C_{24}$ alkylene or $C_1$-$C_{24}$ alkenylene; and $R^3$ is H or $OR^5$.

In some different embodiments of Formula (LNP-III), the lipid has one of the following structures (LNP-IIIE) or (LNP-IIIF):

(LNP-IIIE)

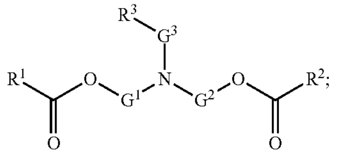

(LNP-IIIF)

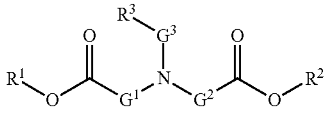

In some of the foregoing embodiments of Formula (LNP-III), the lipid has one of the following structures (LNP-IIIG), (LNP-IIIH), (LNP-IIII), or (LNP-IIIJ):

(LNP-IIIG)

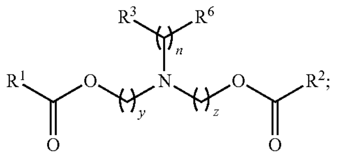

(LNP-IIIH)

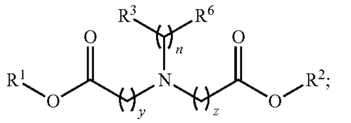

(LNP-IIII)

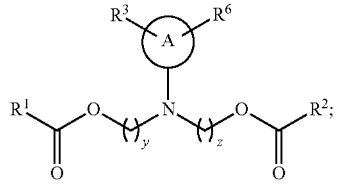

(LNP- IIIJ)

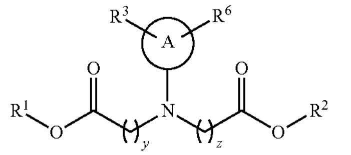

In some of the foregoing embodiments of Formula (LNP-III), n is an integer ranging from 2 to 12, for example from 2 to 8 or from 2 to 4. In some embodiments, n is 3, 4, 5 or 6. In some embodiments, n is 3. In some embodiments, n is 4. In some embodiments, n is 5. In some embodiments, n is 6. In some other of the foregoing embodiments of Formula (LNP-III), y and z are each independently an integer ranging from 2 to 10. For example, in some embodiments, y and z are each independently an integer ranging from 4 to 9 or from 4 to 6. In some of the foregoing embodiments of Formula (LNP-III), $R^6$ is H. In other of the foregoing embodiments, $R^6$ is $C_1$-$C_{24}$ alkyl. In other embodiments, $R^6$ is OH. In some embodiments of Formula (LNP-III), $G^3$ is unsubstituted. In other embodiments, $G^3$ is substituted. In various different embodiments, $G^3$ is linear $C_1$-$C_{24}$ alkylene or linear $C_1$-$C_{24}$ alkenylene. In some other foregoing embodiments of Formula (LNP-III), $R^1$ or $R^2$, or both, is C6-$C_{24}$ alkenyl. For example, in some embodiments, $R^1$ and $R^2$ each, independently have the following structure:

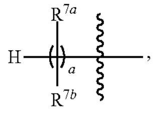
, wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12. In some of the foregoing embodiments of Formula (LNP-III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, C1-$C_8$ alkyl is methyl, ethyl, n-propyl, iso-propyl, n-butyl, iso-butyl, tert-butyl, n-hexyl or n-octyl.

In different embodiments of Formula (LNP-III), $R^1$ or $R^2$, or both, has one of the following structures:

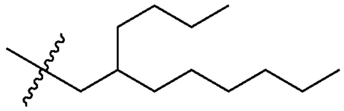
;

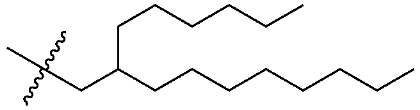
;

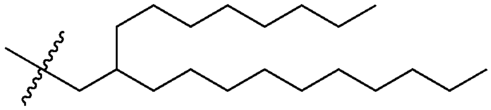
;

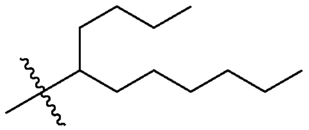
;

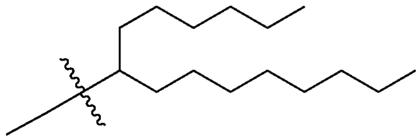
;

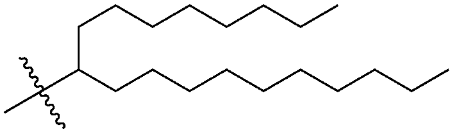
;

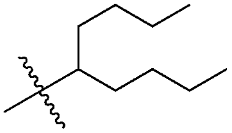
;

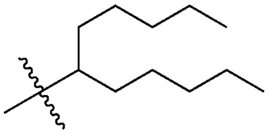
;

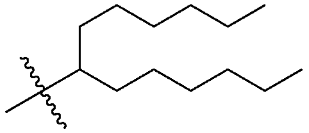
;

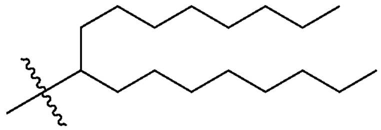
.

In preferred embodiments, the cationic lipid of the LNP is a compound of formula (LNP-III), wherein:

$L^1$ and $L^2$ are each independently —O(C═O)— or (C═O)—O—; and $R^1$ and $R^2$ each independently have one of the following structures:

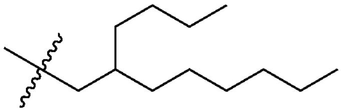 ;

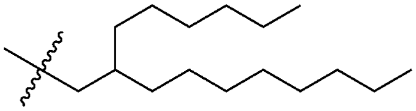 ;

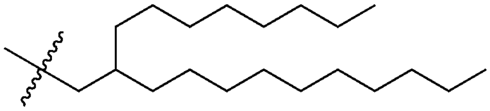 ;

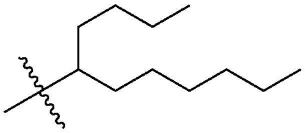 ;

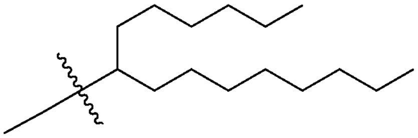 ;

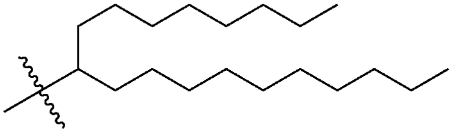 ;

-continued

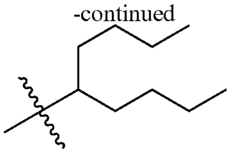 ;

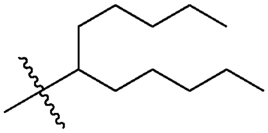 ;

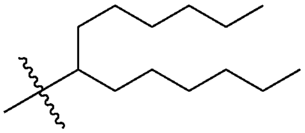 ;

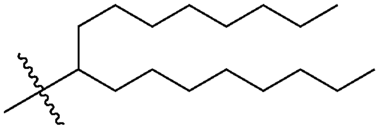 .

In some of the foregoing embodiments of Formula (LNP-III), $R^3$ is OH, CN, —C(═O)OR$^4$, —OC(═O)R$^4$ or —NHC(═O)R$^4$. In some embodiments, $R^4$ is methyl or ethyl.

In preferred embodiments, the cationic lipid of the LNP is a compound of Formula (LNP-III), wherein $R^3$ is OH.

In particularly preferred embodiment, the mRNA of the invention is complexed with one or more lipids thereby forming lipid nanoparticles (LNP), wherein the LNP is selected from structures (LNP-III-1) to (LNP-III-36) (Table 4 herein).

TABLE 4

Representative lipid compounds derived from Formula (LNP-III)

| No. | Structure |
| --- | --- |
| LNP-III-1 | 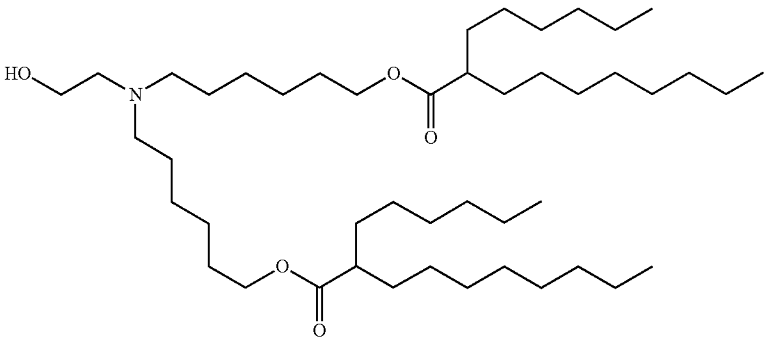 [SMILES: CCCCCCCCC(CCCCCC)C(=O)OCCCCCCN(CCO)CCCCCCOC(=O)C(CCCCCC)CCCCCCCC] |

TABLE 4-continued
| Representative lipid compounds derived from Formula (LNP-III) | |
|---|---|
| No. | Structure |
| LNP-III-2 | 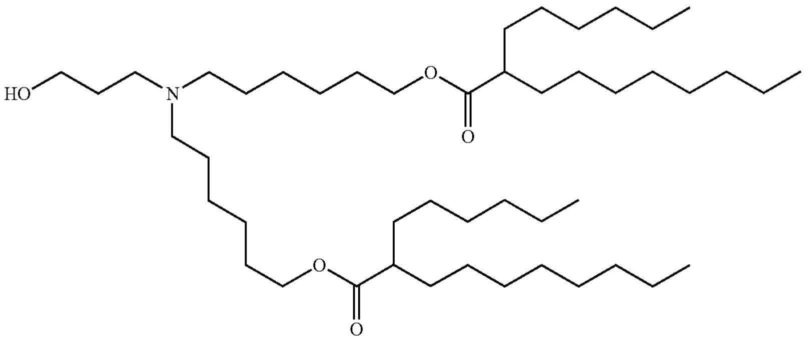 [SMILES: CCCCCCCCC(CCCCCC)C(=O)OCCCCCCN(CCCO)CCCCCCOC(=O)C(CCCCCC)CCCCCCCC] |
| LNP-III-3 | 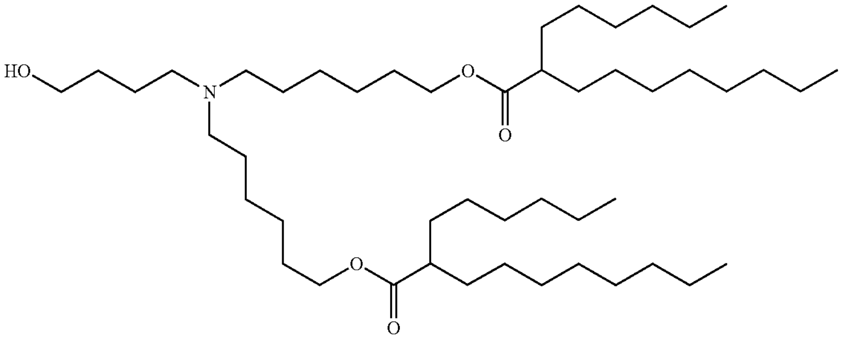 [SMILES: CCCCCCCCC(CCCCCC)C(=O)OCCCCCCN(CCCCO)CCCCCCOC(=O)C(CCCCCC)CCCCCCCC] |
| LNP-III-4 | 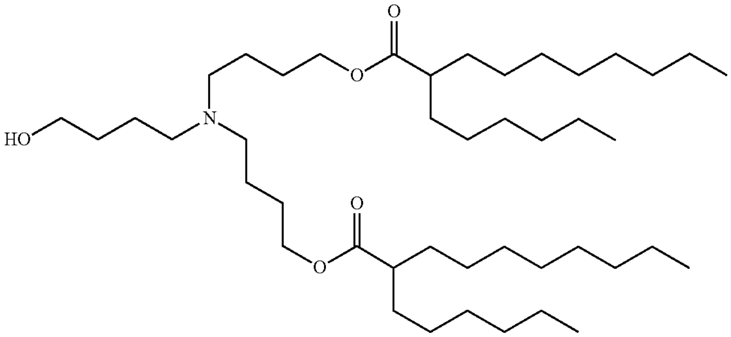 [SMILES: CCCCCCCCC(CCCCCC)C(=O)OCCCCN(CCCCO)CCCCOC(=O)C(CCCCCC)CCCCCCCC] |
| LNP-III-5 | 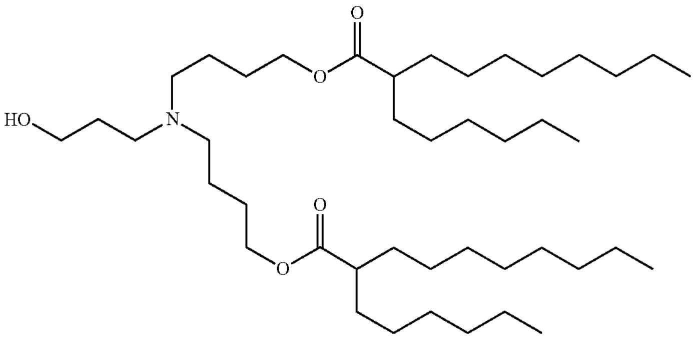 [SMILES: CCCCCCCCC(CCCCCC)C(=O)OCCCCN(CCCO)CCCCOC(=O)C(CCCCCC)CCCCCCCC] |

TABLE 4-continued
| Representative lipid compounds derived from Formula (LNP-III) | |
|---|---|
| No. | Structure |
| LNP-III-6 | 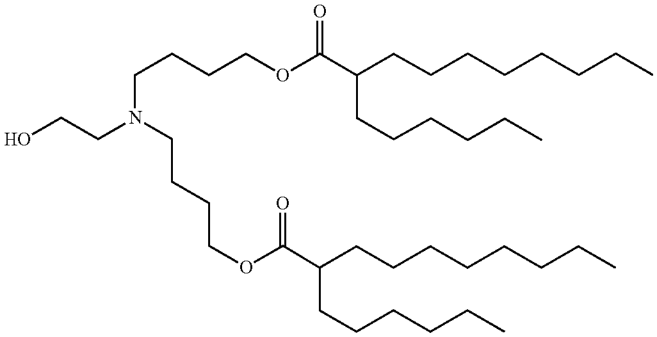 [SMILES: CCCCCCCCC(CCCCCC)C(=O)OCCCCN(CCO)CCCCOC(=O)C(CCCCCC)CCCCCCCC] |
| LNP-III-7 | 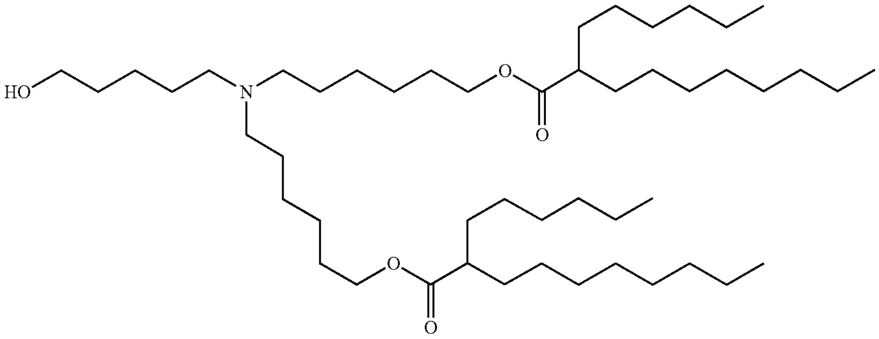 [SMILES: CCCCCCCCC(CCCCCC)C(=O)OCCCCCCN(CCCCCO)CCCCCCOC(=O)C(CCCCCC)CCCCCCCC] |
| LNP-III-8 | 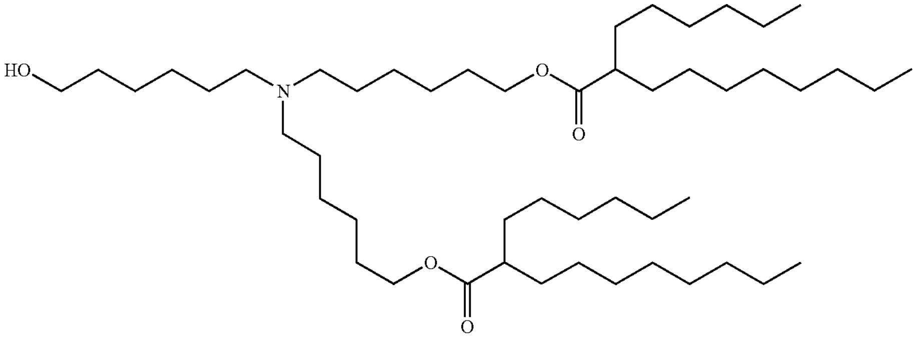 [SMILES: CCCCCCCCC(CCCCCC)C(=O)OCCCCCCN(CCCCCCO)CCCCCCOC(=O)C(CCCCCC)CCCCCCCC] |
| LNP-III-9 | 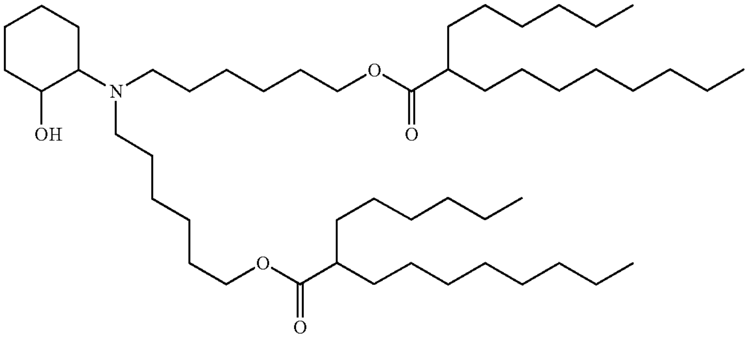 [SMILES: CCCCCCCCC(CCCCCC)C(=O)OCCCCCCN(CCCCCCOC(=O)C(CCCCCC)CCCCCCCC)C1CCCCC1O] |

TABLE 4-continued
| Representative lipid compounds derived from Formula (LNP-III) | |
|---|---|
| No. | Structure |
| LNP-III-10 | 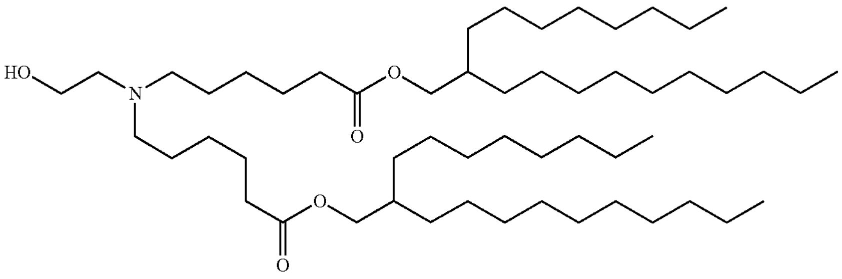 [SMILES: CCCCCCCCCCC(CCCCCCCC)COC(=O)CCCCCN(CCO)CCCCCC(=O)OCC(CCCCCCCC)CCCCCCCCCC] |
| LNP-III-11 | 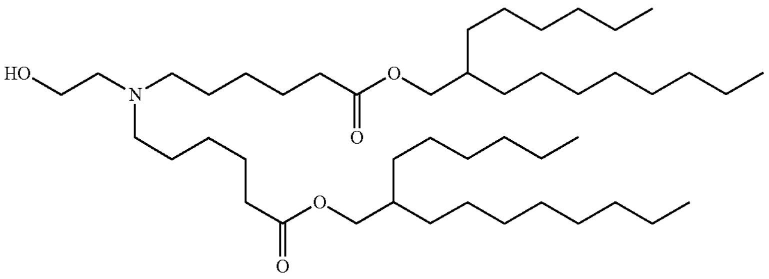 [SMILES: CCCCCCCCC(CCCCCC)COC(=O)CCCCCN(CCO)CCCCCC(=O)OCC(CCCCCC)CCCCCCCC] |
| LNP-III-12 | 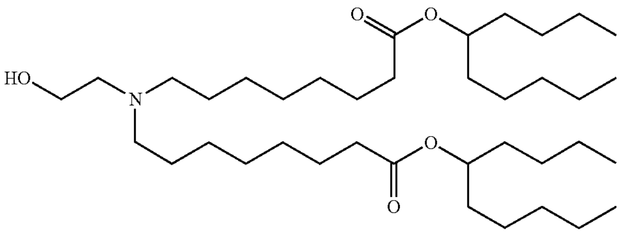 [SMILES: CCCCCC(CCCC)OC(=O)CCCCCCCN(CCO)CCCCCCCC(=O)OC(CCCC)CCCCC] |
| LNP-III-13 | 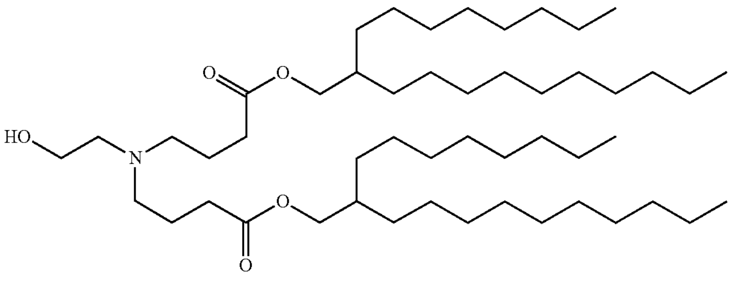 [SMILES: CCCCCCCCCCC(CCCCCCCC)COC(=O)CCCN(CCO)CCCC(=O)OCC(CCCCCCCC)CCCCCCCCCC] |
| LNP-III-14 | 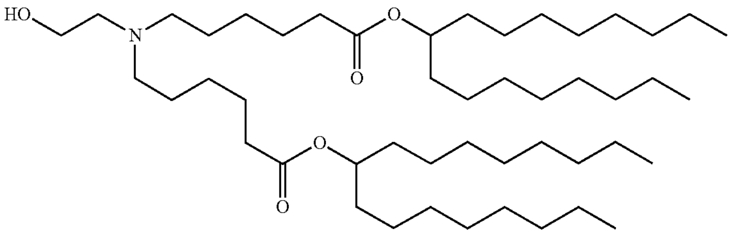 [SMILES: CCCCCCCCC(CCCCCCCC)OC(=O)CCCCCN(CCO)CCCCCC(=O)OC(CCCCCCCC)CCCCCCCC] |

TABLE 4-continued
| Representative lipid compounds derived from Formula (LNP-III) | |
|---|---|
| No. | Structure |
| LNP-III-15 | 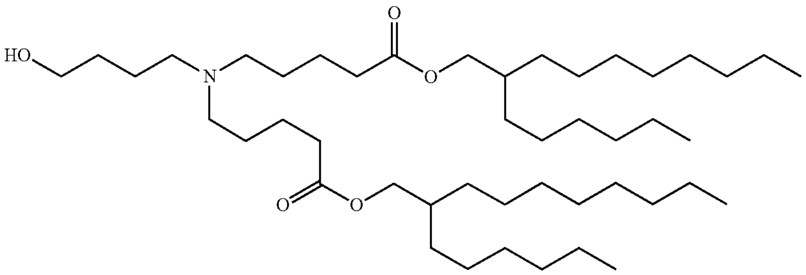 [SMILES: CCCCCCCCC(CCCCCC)COC(=O)CCCCN(CCCCO)CCCCC(=O)OCC(CCCCCC)CCCCCCCC] |
| LNP-III-16 | 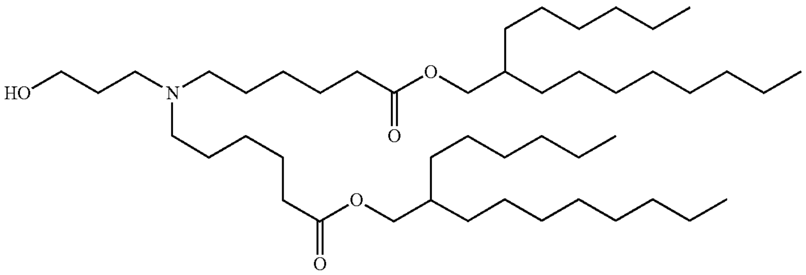 [SMILES: CCCCCCCCC(CCCCCC)COC(=O)CCCCCN(CCCO)CCCCCC(=O)OCC(CCCCCC)CCCCCCCC] |
| LNP-III-17 | 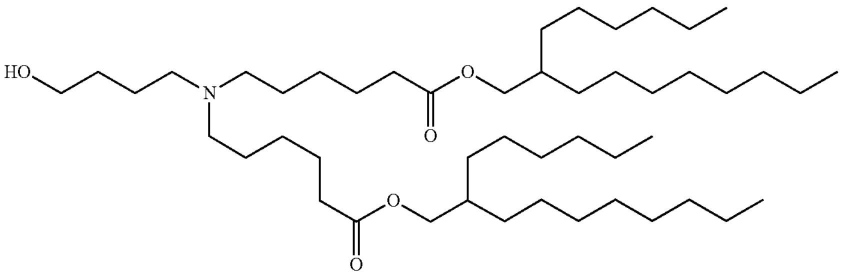 [SMILES: CCCCCCCCC(CCCCCC)COC(=O)CCCCCN(CCCCO)CCCCCC(=O)OCC(CCCCCC)CCCCCCCC] |
| LNP-III-18 | 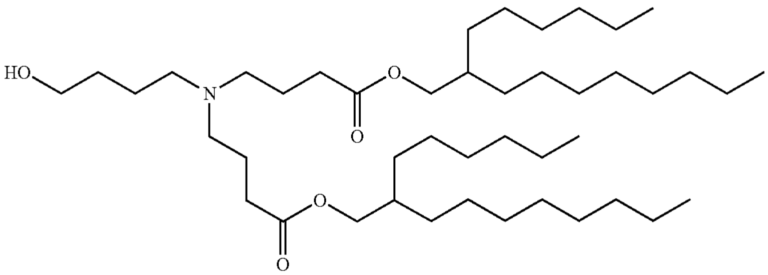 [SMILES: CCCCCCCCC(CCCCCC)COC(=O)CCCN(CCCCO)CCCC(=O)OCC(CCCCCC)CCCCCCCC] |
| LNP-III-19 | 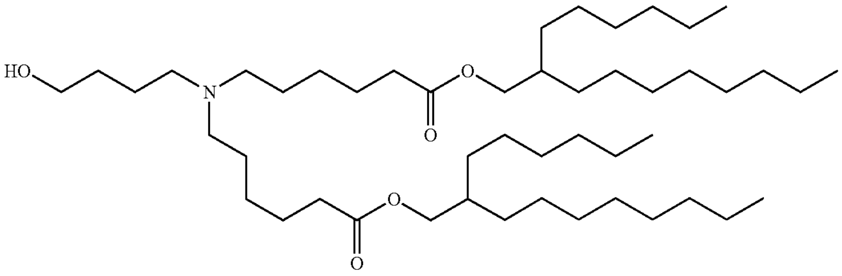 [SMILES: CCCCCCCCC(CCCCCC)COC(=O)CCCCCN(CCCCO)CCCCCC(=O)OCC(CCCCCC)CCCCCCCC] |

TABLE 4-continued
| Representative lipid compounds derived from Formula (LNP-III) | |
|---|---|
| No. | Structure |
| LNP-III-20 | 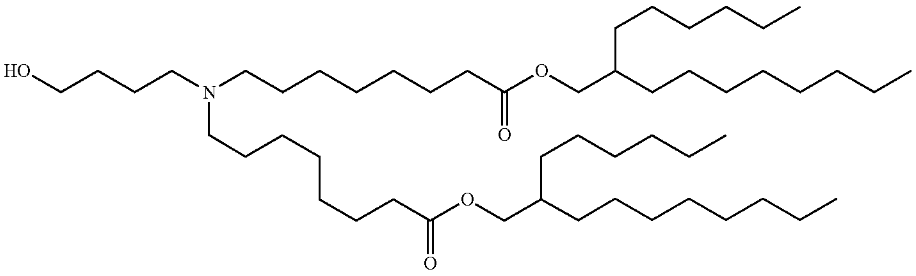 [SMILES: CCCCCCCCC(CCCCCC)COC(=O)CCCCCCCN(CCCCO)CCCCCCCC(=O)OCC(CCCCCC)CCCCCCCC] |
| LNP-III-21 | 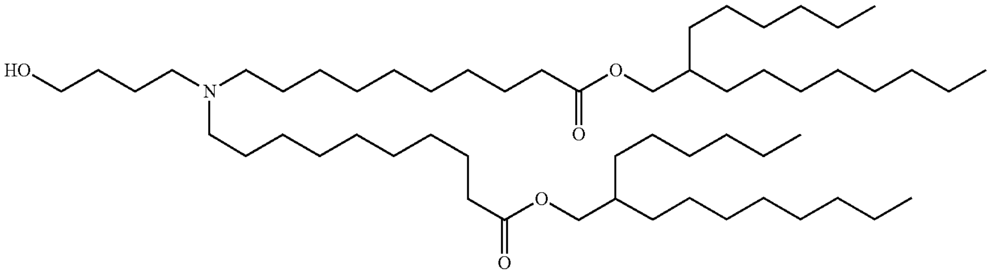 [SMILES: CCCCCCCCC(CCCCCC)COC(=O)CCCCCCCCCN(CCCCO)CCCCCCCCCC(=O)OCC(CCCCCC)CCCCCCCC] |
| LNP-III-22 | 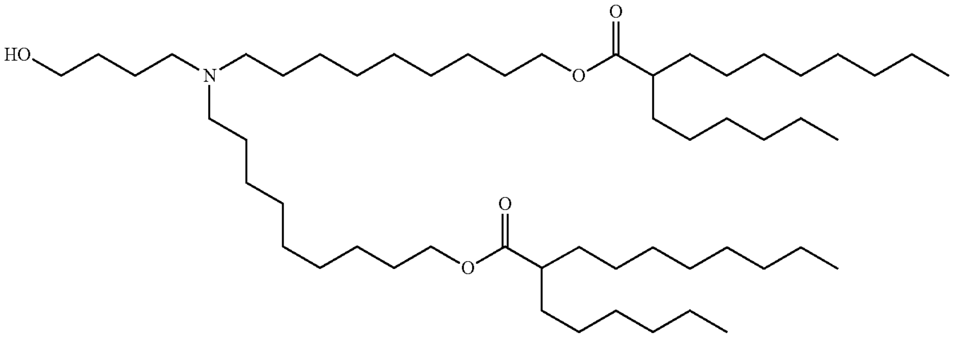 [SMILES: CCCCCCCCC(CCCCCC)C(=O)OCCCCCCCCCN(CCCCO)CCCCCCCCCOC(=O)C(CCCCCC)CCCCCCCC] |
| LNP-III-23 | 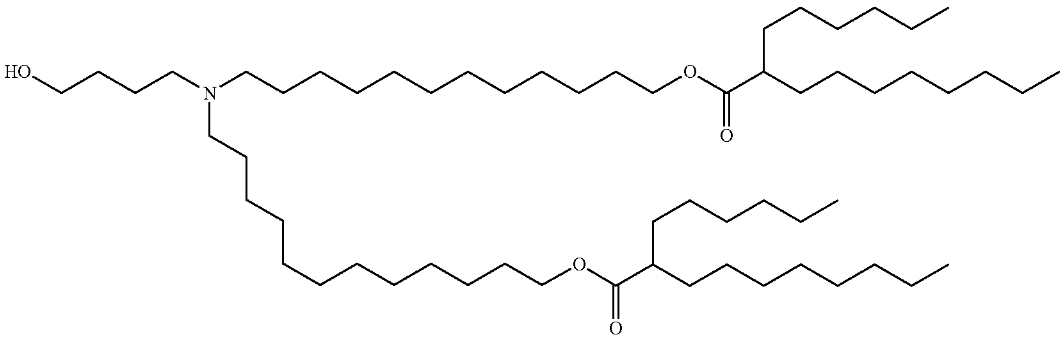 [SMILES: CCCCCCCCC(CCCCCC)C(=O)OCCCCCCCCCCCCN(CCCCO)CCCCCCCCCCCCOC(=O)C(CCCCCC)CCCCCCCC] |

TABLE 4-continued
| Representative lipid compounds derived from Formula (LNP-III) | |
|---|---|
| No. | Structure |
| LNP-III-24 | 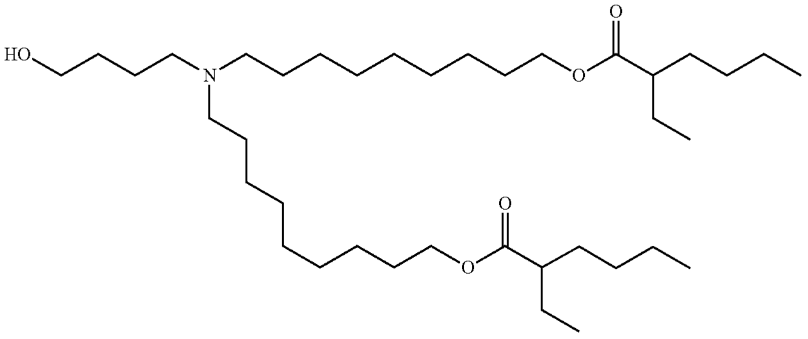 [SMILES: CCCCC(CC)C(=O)OCCCCCCCCCN(CCCCO)CCCCCCCCCOC(=O)C(CC)CCCC] |
| LNP-III-25 | 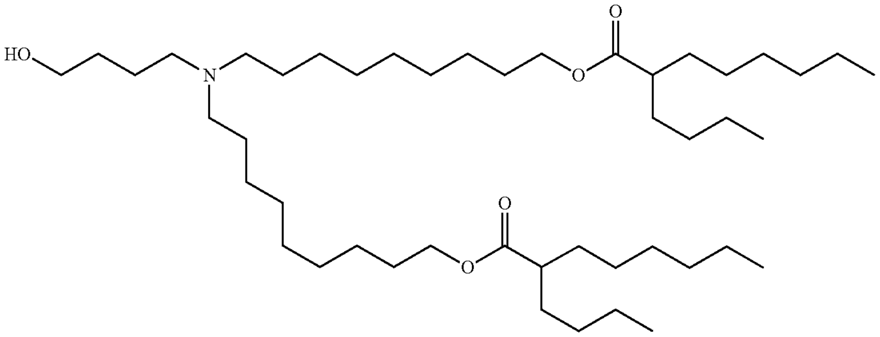 [SMILES: CCCCCCC(CCCC)C(=O)OCCCCCCCCCN(CCCCO)CCCCCCCCCOC(=O)C(CCCC)CCCCCC] |
| LNP-III-26 | 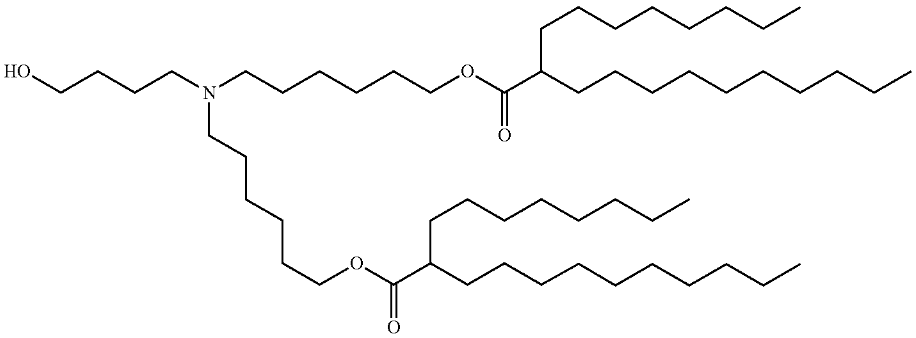 [SMILES: CCCCCCCCCCC(CCCCCCCC)C(=O)OCCCCCCN(CCCCO)CCCCCCOC(=O)C(CCCCCCCC)CCCCCCCCCC] |
| LNP-III-27 | 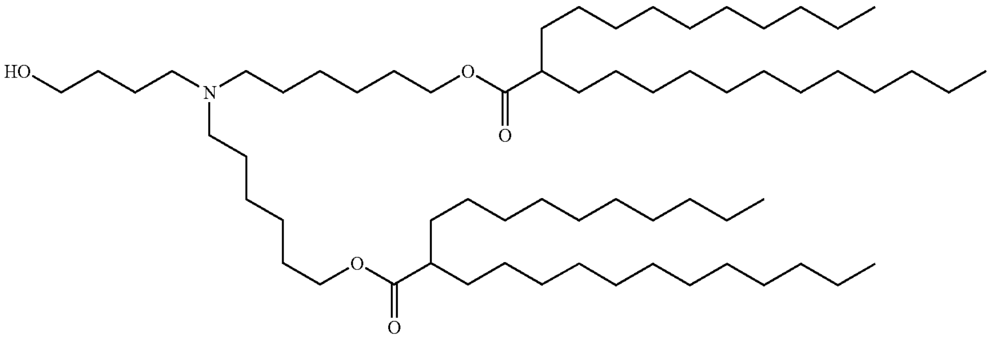 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |

TABLE 4-continued
| Representative lipid compounds derived from Formula (LNP-III) | |
|---|---|
| No. | Structure |
| LNP-III-28 | 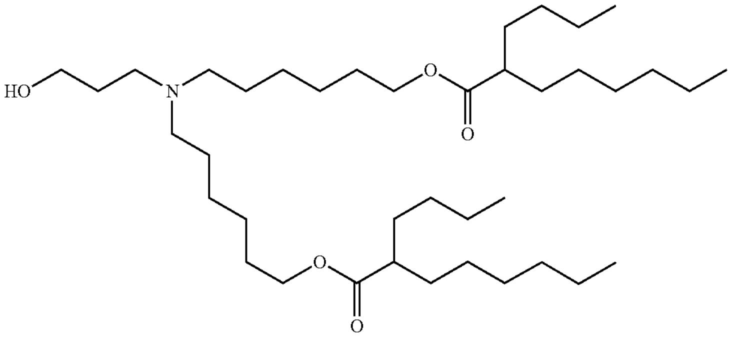 [SMILES: CCCCCCC(CCCC)C(=O)OCCCCCCN(CCCO)CCCCCCOC(=O)C(CCCC)CCCCCC] |
| LNP-III-29 | 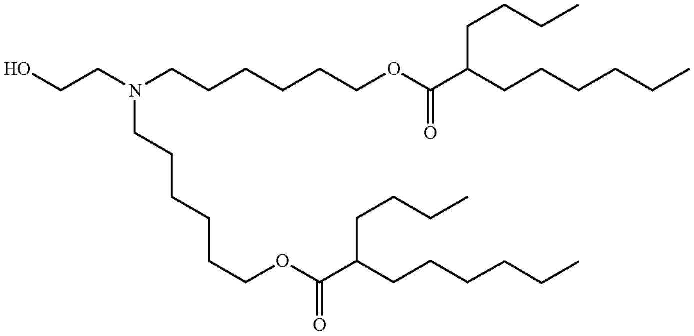 [SMILES: CCCCCCC(CCCC)C(=O)OCCCCCCN(CCO)CCCCCCOC(=O)C(CCCC)CCCCCC] |
| LNP-III-30 | 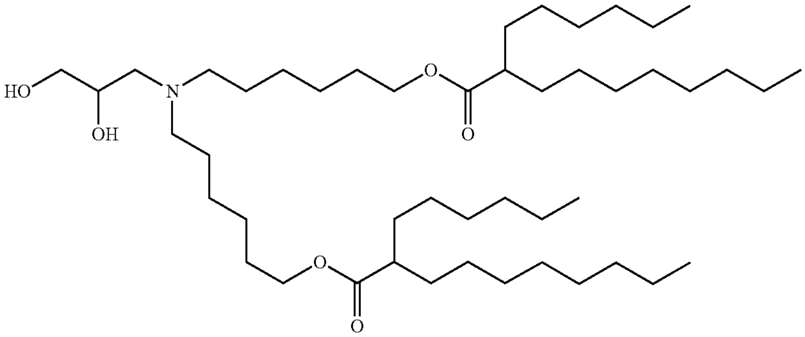 [SMILES: CCCCCCCCC(CCCCCC)C(=O)OCCCCCCN(CCCCCCOC(=O)C(CCCCCC)CCCCCCCC)CC(O)CO] |
| LNP-III-31 | 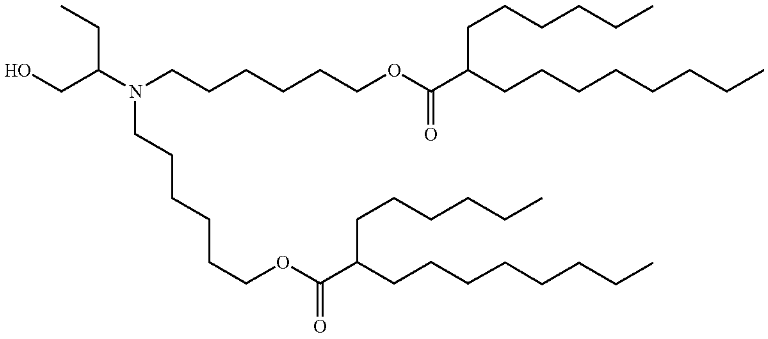 [SMILES: CCCCCCCCC(CCCCCC)C(=O)OCCCCCCN(CCCCCCOC(=O)C(CCCCCC)CCCCCCCC)C(CC)CO] |

TABLE 4-continued
| Representative lipid compounds derived from Formula (LNP-III) | |
|---|---|
| No. | Structure |
| LNP-III-32 | 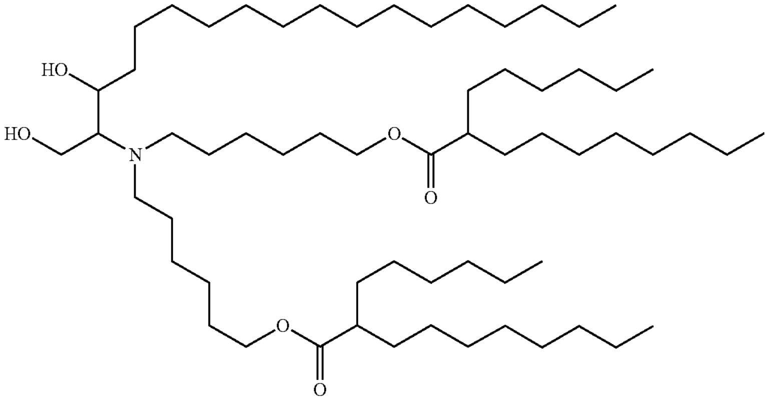 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |
| LNP-III-33 | 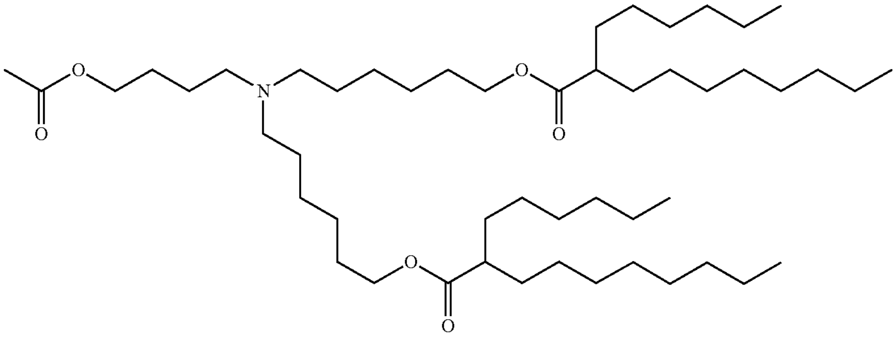 [SMILES: CCCCCCCCC(CCCCCC)C(=O)OCCCCCCN(CCCCCCOC(=O)C(CCCCCC)CCCCCCCC)CCCCOC(C)=O] |
| LNP-III-34 | 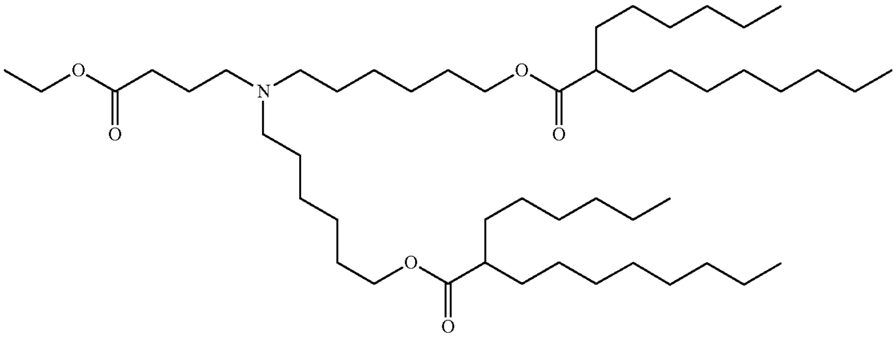 [SMILES: CCCCCCCCC(CCCCCC)C(=O)OCCCCCCN(CCCCCCOC(=O)C(CCCCCC)CCCCCCCC)CCCC(=O)OCC] |
| LNP-III-35 | 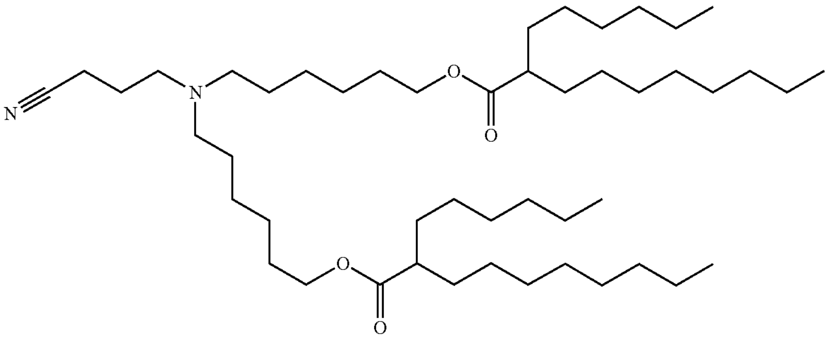 [SMILES: CCCCCCCCC(CCCCCC)C(=O)OCCCCCCN(CCCC#N)CCCCCCOC(=O)C(CCCCCC)CCCCCCCC] |

TABLE 4-continued

Representative lipid compounds derived from Formula (LNP-III)

| No. | Structure |
| --- | --- |
| LNP-III-36 | 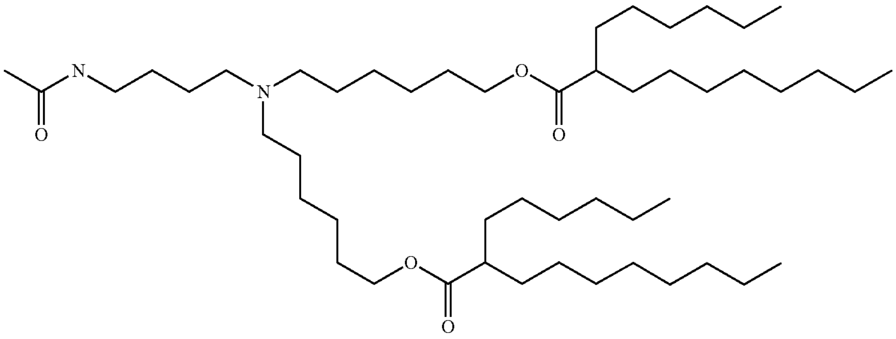 |

In a preferred embodiment, the LNPs comprise a lipid of Formula (LNP-III), at least one mRNA molecule of the invention, and one or more excipient preferably selected from neutral lipids, steroids and PEGylated lipids. In particularly preferred embodiments the lipid of Formula (LNP-III) is compound (LNP-III-3). In some embodiments the lipid of Formula (LNP-III) is compound (LNP-JJJ-7).

In another preferred embodiment, the LNP comprises a cationic lipid selected from:

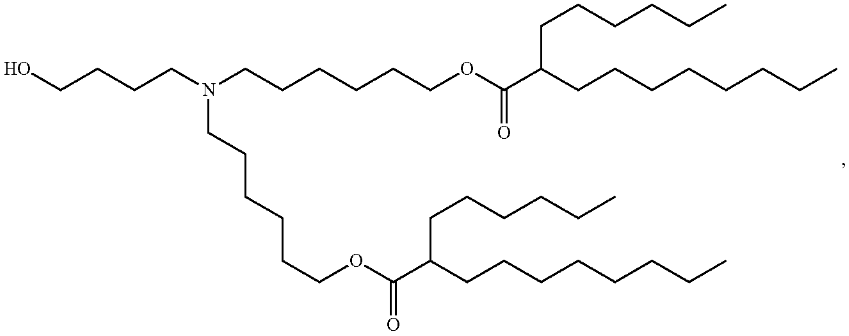

,

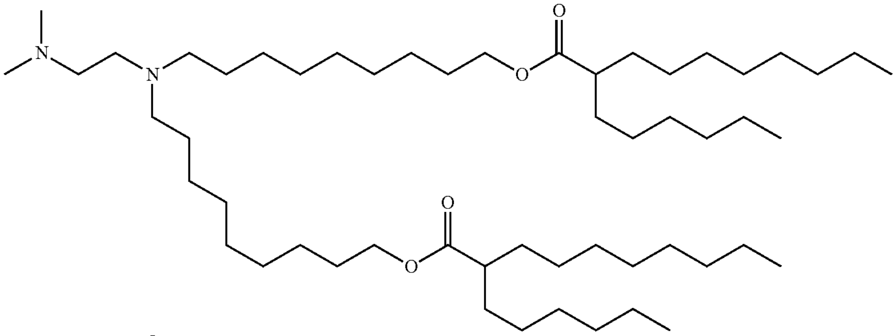

,

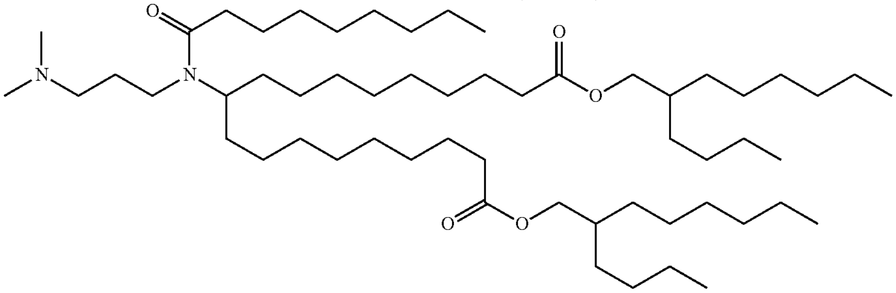

and

-continued

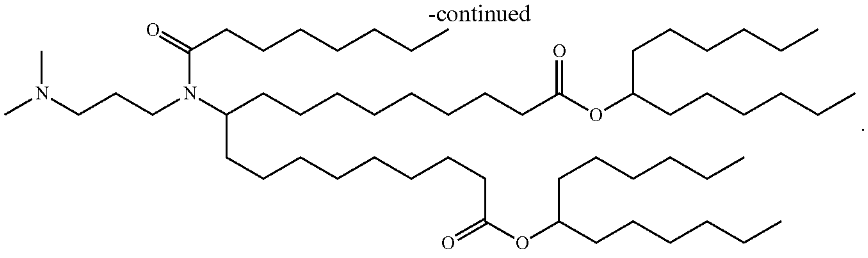

In a particularly preferred embodiment, the mRNA, of the invention is complexed with one or more lipids thereby forming lipid nanoparticles (LNP), wherein the LNP comprises the following cationic lipid (lipid according to Formula LNP-III-3 of Table 4:

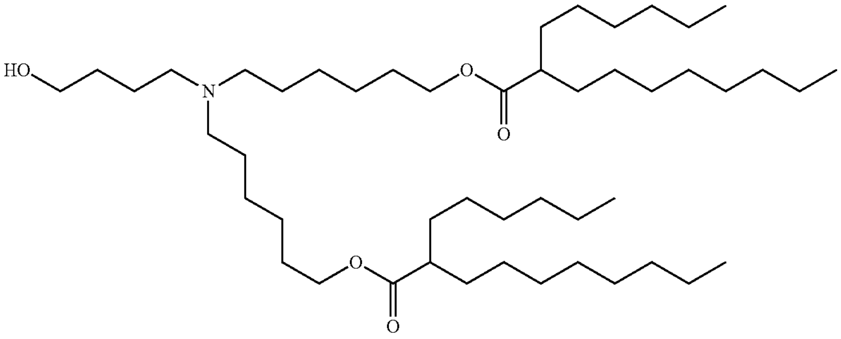 [SMILES: CCCCCCCCC(CCCCCC)C(=O)OCCCCCCN(CCCCO)CCCCCCOC(=O)C(CCCCCC)CCCCCCCC]

In one preferred embodiment, the cationic lipid as defined herein, preferably as disclosed in Table 4, more preferably cationic lipid compound LNP-III-3, is present in the LNP in an amount from about 30 to about 95 mole percent, relative to the total lipid content of the LNP. If more than one cationic lipid is incorporated within the LNP, such percentages apply to the combined cationic lipids.

In another preferred embodiment, the cationic lipid is present in the LNP in an amount from about 30 to about 70 mole percent. In one embodiment, the cationic lipid is present in the LNP in an amount from about 40 to about 60 mole percent, such as about 40, 41, 42, 43, 44, 45, 46, 47, 48, 49, 50, 51, 52, 53, 54, 55, 56, 57, 58, 59 or 60 mole percent, respectively. In embodiments, the cationic lipid is present in the LNP in an amount from about 47 to about 48 mole percent, such as about 47.0, 47.1, 47.2, 47.3, 47.4, 47.5, 47.6, 47.7, 47.8, 47.9, 50.0 mole percent, respectively, wherein 47.7 mole percent are particularly preferred.

The cationic lipid can be present in a ratio of from about 20 mol % to about 70 or 75 mol % or from about 45 to about 65 mol % or about 20, 25, 30, 35, 40, 45, 50, 55, 60, 65, or about 70 mol % of the total lipid present in the LNP. In further embodiments, the LNPs comprise from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle). In some embodiments, the ratio of cationic lipid to nucleic acid, preferably to the mRNA of the invention, is from about 3 to about 15, such as from about 5 to about 13 or from about 7 to about 11. In one preferred embodiment, the ration of cationic lipid to nucleic acid, preferably to an mRNA of the invention, is about 6.

In one preferred embodiment, the LNP comprises a combination or mixture of any the lipids described above.

In one preferred embodiment, amino or cationic lipids as defined herein have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of lipids have to be present in the charged or neutral form. Lipids having more than one protonatable or deprotonatable group, or which are zwitterionic, are not excluded and may likewise suitable in the context of the present invention.

In one preferred embodiment, the protonatable lipids have a pKa of the protonatable group in the range of about 4 to about 11, e.g., a pKa of about 5 to about 7.

LNPs can comprise two or more (different) cationic lipids. The cationic lipids may be selected to contribute different advantageous properties. For example, cationic lipids that differ in properties such as amine pKa, chemical stability, half-life in circulation, half-life in tissue, net accumulation in tissue, or toxicity can be used in the LNP. In particular, the cationic lipids can be chosen so that the properties of the mixed-LNP are more desirable than the properties of a single-LNP of individual lipids.

The amount of the permanently cationic lipid or lipidoid may be selected taking the amount of the nucleic acid cargo into account. In one embodiment, these amounts are selected such as to result in an N/P ratio of the nanoparticle(s) or of the composition in the range from about 0.1 to about 20. In this context, the N/P ratio is defined as the mole ratio of the nitrogen atoms ("N") of the basic nitrogen-containing groups of the lipid or lipidoid to the phosphate groups ("P") of the RNA which is used as cargo. The N/P ratio may be calculated on the basis that, for example, 1 g RNA typically contains about 3 nmol phosphate residues, provided that the RNA exhibits a statistical distribution of bases. The "N"-value of the lipid or lipidoid may be calculated on the basis of its molecular weight and the relative content of permanently cationic and—if present—cationisable groups.

LNP in vivo characteristics and behavior can be modified by addition of a hydrophilic polymer coating, e.g. polyethylene glycol (PEG), to the LNP surface to confer steric stabilization. Furthermore, LNPs can be used for specific targeting by attaching ligands (e.g. antibodies, peptides, and carbohydrates) to its surface or to the terminal end of the attached PEG chains (e.g. via PEGylated lipids or PEGylated cholesterol).

In a preferred embodiment, the LNPs comprise a polymer conjugated lipid. The term "polymer conjugated lipid" refers to a molecule comprising both a lipid portion and a polymer portion. An example of a polymer conjugated lipid is a PEGylated lipid or PEG-modified lipid. The term "PEGylated lipid or PEG-modified lipid" refers to a molecule comprising both a lipid portion and a polyethylene glycol portion. PEGylated lipids are known in the art and include 1-(monomethoxy-polyethyleneglycol)-2,3-dimyristoylglycerol (PEG-s-DMG) and the like. In this context 2-mPEG2000-n,n ditetradecylacetamide is particularly preferred to be used as PEGylated lipid.

Other suitable amino lipids include those having alternative fatty acid groups and other dialkylamino groups, including those in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to C22 may be used. Other scaffolds can also be used to separate the amino group and the fatty acid or fatty alkyl portion of the amino lipid.

Amino or cationic lipids may have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the invention.

The protonatable lipids may have a pKa of the protonatable group in the range of about 4 to about 11, e.g., a pKa of about 5 to about 7. In one preferred embodiment, the protonatable lipids may have a pKa of the protonable group of about 6.09.

LNPs may include two or more cationic lipids. The cationic lipids may be selected to contribute different advantageous properties. For example, cationic lipids that differ in properties such as amine pKa, chemical stability, half-life in circulation, half-life in tissue, net accumulation in tissue, or toxicity may be used in the LNP. In particular, the cationic lipids may be chosen so that the properties of the mixed-LNP are more desirable than the properties of a single-LNP of individual lipids.

The cationic lipid may be present in a ratio of from about 20 mol % to about 70 or 75 mol % or from about 45 to about 65 mol % or about 20, 25, 30, 35, 40, 45, 50, 55, 60, 65, or about 70 mol % of the total lipid present in the LNP. LNPs may comprise from about 25% to about 75% on a molar basis of cationic lipid, e.g., from about 20 to about 70%, from about 35 to about 65%, from about 45 to about 65%, about 60%, about 50% or about 40% on a molar basis (based upon 100% total moles of lipid in the lipid nanoparticle). The ratio of cationic lipid to nucleic acid may be from about 3 to about 15, such as from about 5 to about 13 or from about 7 to about 11. Specifically, the liposome may have a molar ratio of nitrogen atoms in the cationic lipid to the phosphates in the RNA (N:P ratio) of between 1:1 and 20:1 as described in International Publication No. WO 2013/006825 A1. Alternatively, the liposome may have a N:P ratio of greater than 20:1 or less than 1:1.

(ii) Neutral and Non-Cationic Lipids

The non-cationic lipid may be a neutral lipid, an anionic lipid, or an amphipathic lipid. Neutral lipids, when present, may be selected any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., LNP size and stability of the LNP in the bloodstream. Preferably, the neutral lipid is a lipid having two acyl groups (e.g., diacylphosphatidylcholine and diacylphosphatidylethanolamine).

Neutral lipids may contain saturated fatty acids with carbon chain lengths in the range of $C_{10}$ to $C_{20}$. In other embodiments, neutral lipids with mono or diunsaturated fatty acids with carbon chain lengths in the range of $C_{10}$ to $C_{20}$ are used. Additionally or alternatively, neutral lipids having mixtures of saturated and unsaturated fatty acid chains may be used.

Suitable neutral lipids include, but are not limited to, distearoylphophocholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), dimyristoyl phosphatidylcholine (DMPC), distearoyl-phosphatidyl-ethanolamine (DSPE), SM, 16-0-monomethyl PE, 16-O-dimethyl PE, 18-1-trans PE, 1-stearoyl-2-oleoyl-phosphatidyethanolamine (SOPE), cholesterol, or a mixture thereof. Anionic lipids suitable for use in LNPs include, but are not limited to, phosphatidylglycerol, cardiolipin, diacyl-phosphatidylserine, diacylphosphatidic acid, N-dodecanoyl phosphatidylethanoloamine, N-succinyl phosphatidyl-ethanolamine, N-glutaryl phosphatidylethanolamine, lysylphosphatidylglycerol, and other anionic modifying groups joined to neutral lipids. In this context, the use of distearoylphophocholine (DSPC) as neutral lipid is particularly preferred.

Amphipathic lipids refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyl-oleoyl phosphatdylcholine, lysophosphatidylcholine, lysophosphatidylethanolamine, dipalmitoylphosphatidylcholine, dioleoylphosphatidylcholine, distearoylphophocholine, or dilinoleoylphosphatidylcholine. Other phosphorus-lacking compounds, such as sphingolipids, glycosphingolipid families, diacylglycerols, and beta-acyloxyacids, can also be used.

In some embodiments, the LNPs comprise a neutral lipid selected from DSPC, DPPC, DMPC, DOPC, POPC, DOPE and SM. In various embodiments, the molar ratio of the cationic lipid to the neutral lipid ranges from about 2:1 to about 8:1. In one preferred embodiment the molar ratio of the cationic lipid to the neutral lipid ranges from about 4:1 about to 5:1.

In preferred embodiments the neutral lipid is 1,2-distearoyl-sn-glycero-3-phosphocholine (DSPC). The molar ratio of the cationic lipid to DSPC may be in the range from about 2:1 to 8:1. In one preferred embodiment the molar ratio of the cationic lipid to the neutral lipid ranges from about 4:1 to about a 5:1.

The non-cationic lipid may be present in a ratio of from about 5 mol % to about 90 mol %, about 5 mol % to about 10 mol %, about 5, 10, 15, 20, 25, 30, 35, 40, 45, 50, 55, 60, 65, 70, 75, 80, 85, or about 90 mol % of the total lipid present in the LNP.

LNPs may comprise from about 0% to about 15 or 45% on a molar basis of neutral lipid, e.g., from about 3 to about 12% or from about 5 to about 10%. For instance, LNPs may include about 15%, about 10%, about 7.5%, or about 7.1% of neutral lipid on a molar basis (based upon 100% total moles of lipid in the LNP). Particularly preferred are 10 mol % of DSPC as neutral lipid.

(iii) Sterols

The sterol may preferably be cholesterol.

The sterol may be present in a ratio of about 10 mol % to about 60 mol % or about 25 mol % to about 40 mol % of the LNP. The sterol may be present in a ratio of about 10, 15, 20, 25, 30, 35, 40, 45, 50, 55, or about 60 mol % of the total lipid present in the LNP. LNPs may comprise from about 5% to about 50% on a molar basis of the sterol, e.g., about 15% to about 45%, about 20% to about 40%, about 48%, about 40%, about 38.5%, about 35%, about 34.4%, about 31.5% or about 31% on a molar basis (based upon 100% total moles of lipid in the LNP). In this context 40.9 mol % of cholesterol are particularly preferred.

(iv) Aggregation Reducing Agents

The aggregation reducing agent may be a lipid capable of reducing aggregation.

Examples of such lipids include, but are not limited to, polyethylene glycol (PEG)-modified lipids, monosialoganglioside Gml, and polyamide oligomers (PAO) such as those described in U.S. Pat. No. 6,320,017. Other compounds with uncharged, hydrophilic, steric-barrier moieties, which prevent aggregation during formulation, like PEG, Gml or ATTA, can also be coupled to lipids. ATTA-lipids are described, e.g., in U.S. Pat. No. 6,320,017, and PEG-lipid conjugates are described, e.g., in U.S. Pat. Nos. 5,820,873, 5,534,499 and 5,885,613.

The aggregation reducing agent may be, for example, selected from a polyethyleneglycol (PEG)-lipid including, without limitation, a PEG-diacylglycerol (DAG), a PEG-dialkylglycerol, a PEG-dialkyloxypropyl (DAA), a PEG-phospholipid, a PEG-ceramide (Cer), or a mixture thereof (such as PEG-$Cer_{14}$ or PEG-$Cer_{20}$). The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). Other pegylated-lipids include, but are not limited to, polyethylene glycol-didimyristoyl glycerol ($C_{14}$—PEG or PEG-$C_{14}$, where PEG has an average molecular weight of 2000 Da) (PEG-DMG); (R)-2,3-bis(octadecyloxy)propyl-1-(methoxy poly(ethyleneglycol)2000)propylcarbamate) (PEG-DSG); PEG-carbamoyl-1,2-dimyristyloxypropylamine, in which PEG has an average molecular weight of 2000 Da (PEG-cDMA); N-Acetylgalactosamine-((R)-2,3-bis(octadecyloxy)propyl-1-(methoxy poly(ethylene glycol)2000)propylcarbamate)) (GalNAc-PEG-DSG); mPEG (mw2000)-diastearoylphosphatidyl-ethanolamine (PEG-DSPE); and polyethylene glycol-dipalmitoylglycerol (PEG-DPG).

Preferably, the aggregation reducing agent may be selected from PEG-DMG or PEG-c-DMA.

In preferred embodiments the mRNA, of the invention is complexed with one or more lipids thereby forming lipid nanoparticles (LNP), wherein the LNP additionally comprises a PEGylated lipid with the Formula (LNP-IV):

(LNP-IV)

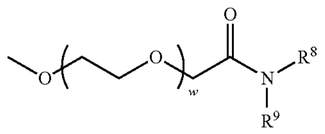

or a pharmaceutically acceptable salt, tautomer or stereoisomer thereof, wherein $R^8$ and $R^9$ are each independently a straight or branched, saturated or unsaturated alkyl chain containing from 10 to 30 carbon atoms, wherein the alkyl chain is optionally interrupted by one or more ester bonds; and w has mean value ranging from 30 to 60.

In some of the foregoing embodiments of the PEGylated lipid according to Formula (LNP-IV), $R^8$ and $R^9$ are not both n-octadecyl when w is 42. In some other embodiments, $R^8$ and $R^9$ are each independently a straight or branched, saturated or unsaturated alkyl chain containing from 10 to 18 carbon atoms. In some embodiments, $R^8$ and $R^9$ are each independently a straight or branched, saturated or unsaturated alkyl chain containing from 12 to 16 carbon atoms. In some embodiments, $R^8$ and $R^9$ are each independently a straight or branched, saturated or unsaturated alkyl chain containing 12 carbon atoms. In some embodiments, $R^8$ and $R^9$ are each independently a straight or branched, saturated or unsaturated alkyl chain containing 14 carbon atoms. In other embodiments, $R^8$ and $R^9$ are each independently a straight or branched, saturated or unsaturated alkyl chain containing 16 carbon atoms. In still more embodiments, $R^8$ and $R^9$ are each independently a straight or branched, saturated or unsaturated alkyl chain containing 18 carbon atoms. In still other embodiments, $R^8$ is a straight or branched, saturated or unsaturated alkyl chain containing 12 carbon atoms and $R^9$ is a straight or branched, saturated or unsaturated alkyl chain containing 14 carbon atoms.

In various embodiments, w spans a range that is selected such that the PEG portion of the PEGylated lipid according to Formula (LNP-IV) has an average molecular weight of about 400 to about 6000 g/mol. In some embodiments, the average w is about 50.

In preferred embodiments, $R^8$ and $R^9$ of the PEGylated lipid according to Formula (LNP-IV) are saturated alkyl chains.

In a particularly preferred embodiment, the mRNA molecule, of the invention is complexed with one or more lipids thereby forming lipid nanoparticles (LNP), wherein the LNP additionally comprises a PEGylated lipid, wherein the PEG lipid is of Formula (LNP-IVa)

(LNP-IVa)

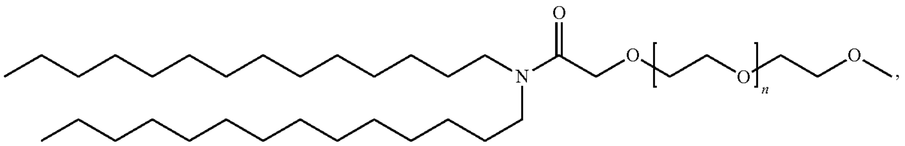

wherein n has a mean value ranging from 30 to 60, such as about 28 to about 32, about 30 to about 34, 32 to about 36, about 34 to about 38, 36 to about 40, about 38 to about 42, 40 to about 44, about 42 to about 46, 44 to about 48, about 46 to about 50, 48 to about 52, about 50 to about 54, 52 to about 56, about 54 to about 58, 56 to about 60, about 58 to about 62. In preferred embodiments, n is about 45, 46, 47, 48, 49, 50, 51, 52, 53, 54. In a most preferred embodiment n has a mean value of 49. In this context 2-mPEG2000-n,n ditetradecylacetamide is particularly preferred. In this context 2-mPEG2000-n,n ditetradecylacetamide is particularly preferred.

In other embodiments, the PEGylated lipid has one of the following structures:

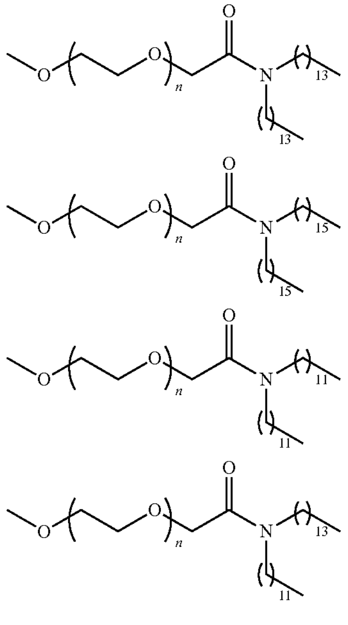

wherein n is an integer selected such that the average molecular weight of the PEGylated lipid is about 2500 g/mol, most preferably n is about 49.

Further examples of PEG-lipids suitable in that context are provided in US20150376115A1 and WO201519995.

In some embodiments, LNPs include less than about 3, 2, or 1 mole percent of PEG or PEG-modified lipid, based on the total moles of lipid in the LNP. In further embodiments, LNPs comprise from about 0.1% to about 20% of the PEG-modified lipid on a molar basis, e.g., about 0.5 to about 10%, about 0.5 to about 5%, about 10%, about 5%, about 3.5%, about 3%, about 2.5%, about 2%, about 1.5%, about 1%, about 0.5%, or about 0.3% on a molar basis (based on 100% total moles of lipids in the LNP). In preferred embodiments, LNPs comprise from about 1.0% to about 2.0% of the PEG-modified lipid on a molar basis, e.g., about 1.2 to about 1.9%, about 1.2 to about 1.8%, about 1.3 to about 1.8%, about 1.4 to about 1.8%, about 1.5 to about 1.8%, about 1.6 to about 1.8%, in particular about 1.4%, about 1.5%, about 1.6%, about 1.7%, about 1.8%, about 1.9%, most preferably 1.7% (based on 100% total moles of lipids in the LNP). In this context 1.7 mol % of 2-mPEG2000-n,n ditetradecylacetamide as PEG-modified lipid are particularly preferred.

In various embodiments, the molar ratio of the cationic lipid to the PEGylated lipid ranges from about 100:1 to about 25:1.

The LNP composition may be influenced by, inter alia, the selection of the cationic lipid component, the degree of cationic lipid saturation, the nature of the PEGylation, the ratio of all components and biophysical parameters such as its size. In one example by Semple et al. (Semple et al. Nature Biotech. 2010 28: 172-176, the LNP composition was composed of 57.1% cationic lipid, 7.1% dipalmitoylphosphatidylcholine, 34.3% cholesterol, and 1.4% PEG-c-DMA (Basha et al. Mol Ther. 2011 19:2186-2200).

LNPs may comprise from about 35 to about 45% cationic lipid, from about 40% to about 50% cationic lipid, from about 50% to about 60% cationic lipid and/or from about 55% to about 65% cationic lipid. The ratio of lipid to nucleic acid may range from about 5:1 to about 20:1, from about 10:1 to about 25:1, from about 15:1 to about 30:1 and/or at least 30:1.

The average molecular weight of the PEG moiety in the PEG-modified lipids can range from about 500 to about 8,000 Daltons (e.g., from about 1,000 to about 4,000 Daltons). In one preferred embodiment, the average molecular weight of the PEG moiety is about 2,000 Daltons. The concentration of the aggregation reducing agent may range from about 0.1 to about 15 mol %, per 100% total moles of lipid in the LNP. In some embodiments, LNPs include less than about 3, 2, or 1 mole percent of PEG or PEG-modified lipid, based on the total moles of lipid in the LNP. In further embodiments, LNPs comprise from about 0.1% to about 20% of the PEG-modified lipid on a molar basis, e.g., about 0.5 to about 10%, about 0.5 to about 5%, about 10%, about 5%, about 3.5%, about 1.5%, about 0.5%, or about 0.3% on a molar basis (based on 100% total moles of lipids in the LNP).

Different LNPs having varying molar ratios of cationic lipid, non-cationic (or neutral) lipid, sterol (e.g., cholesterol), and aggregation reducing agent (such as a PEG-modified lipid) on a molar basis (based upon the total moles of lipid in the lipid nanoparticles) as depicted in Table 5 below. In preferred embodiments, the lipid nanoparticle formulation of the invention consists essentially of a lipid mixture in molar ratios of about 20-70% cationic lipid: 5-45% neutral lipid: 20-55% cholesterol, 0.5-15% PEG-modified lipid, more preferably in molar ratios of about 20-60% cationic lipid: 5-25% neutral lipid: 25-55% cholesterol: 0.5-15% PEG-modified lipid.

TABLE 5

| Lipid-based formulations Molar ratio of Lipids (based upon 100% total moles of lipid in the lipid nanoparticle) | | | |
|---|---|---|---|
| Cationic Lipid | Non-Cationic (or Neutral) Lipid | Sterol | Aggregation Reducing Agent (e.g., PEG-lipid) |
| from about 35% to about 65% | from about 3% to about 12% or 15% | from about 15% to about 45% | from about 0.1% to about 10% (preferably from about 0.5% to about 2% or 3% |
| from about 20% to about 70% | from about 5% to about 45% | from about 20% to about 55% | from about 0.1% to about 10% (preferably from about 0.5% to about 2% or 3% |
| from about 45% to about 65% | from about 5% to about 10% | from about 5% to about 45% | from about 0.1% to about 3% |
| from about 20% to about 60% | from about 5% to about 25% | from about 25% to about 40% | from about 0.1% to about 5% (preferably from about 0.1% to about 3%) |
| about 40% | about 10% | from about 25% to about 55% | about 10% |
| about 35% | about 15% | | about 10% |
| about 52% | about 13% | | about 5% |
| about 50% | about 10% | | about 1.5% |

LNPs may occur as liposomes or lipoplexes as described in further detail below.

Preferably, lipid nanoparticles (LNPs) comprise: (a) at least one mRNA, (b) a cationic lipid, (c) an aggregation reducing agent (such as polyethylene glycol (PEG) lipid or PEG-modified lipid), (d) optionally a non-cationic lipid (such as a neutral lipid), and (e) optionally, a sterol.

In some embodiments, the LNPs comprise a lipid of Formula (LNP-III), an mRNA, as defined above, a neutral lipid, a steroid and a PEGylated lipid. In preferred embodiments, the lipid of Formula (LNP-III) is lipid compound (LNP-III-3), the neutral lipid is DSPC, the steroid is cholesterol, and the PEGylated lipid is the compound of Formula (LNP-Iva, such as 2-mPEG2000-n,n ditetradecylacetamide).

In a preferred embodiment the LNP consists essentially of (i) at least one cationic lipid; (ii) a neutral lipid; (iii) a sterol, e.g., cholesterol; and (iv) a PEG-lipid, e.g. PEG-DMG or PEG-cDMA, in a molar ratio of about 20-60% cationic lipid: 5-25% neutral lipid: 25-55% sterol; 0.5-15% PEG-lipid.

In particularly preferred embodiments, the mRNA, of the invention is complexed with one or more lipids thereby forming lipid nanoparticles (LNP), wherein the LNP essentially consists of (i) at least one cationic lipid as defined herein, preferably a lipid of Formula (LNP-III), more preferably lipid (LNP-III-3);
(ii) a neutral lipid as defined herein, preferably 1,2-distearoyl-sn-glycero-3-phosphocholine (DSPC);
(iii) a steroid or steroid analogue as defined herein, preferably cholesterol; and
(iv) a PEG-lipid as defined herein, e.g. PEG-DMG or PEG-cDMA, preferably a PEGylated lipid of Formula (LNP-Iva, such as 2-mPEG2000-n,n ditetradecylacetamide), wherein (i) to (iv) are in a molar ratio of about 20-60% cationic lipid: 5-25% neutral lipid: 25-55% sterol; 0.5-15% PEG-lipid, most preferably in a molar ratio of 47.7% cationic lipid: 10% neutral lipid: 40.9% sterol; 1.7% PEG-lipid.

In one preferred embodiment, the lipid nanoparticle comprises: a cationic lipid with Formula (LNP-III) and/or PEG lipid with Formula (LNP-IV), optionally a neutral lipid, preferably 1,2-distearoyl-sn-glycero-3-phosphocholine (DSPC) and optionally a steroid, preferably cholesterol, wherein the molar ratio of the cationic lipid to DSPC is optionally in the range from about 2:1 to 8:1, wherein the molar ratio of the cationic lipid to cholesterol is optionally in the range from about 2:1 to 1:1.

In a particular preferred embodiment, the lipid nanoparticles (LNPs), have a molar ratio of approximately 50:10:38.5:1.5, preferably 47.5:10:40.8:1.7 or more preferably 47.4:10:40.9:1.7 (i.e. proportion (mol %) of cationic lipid (preferably lipid LNP-III-3), DSPC, cholesterol and PEG-lipid ((preferably PEG-lipid of Formula (LNP-IVa) with n=49); solubilized in ethanol).

The total amount of mRNA in the lipid nanoparticles may vary and is defined depending on the e.g. RNA to total lipid w/w ratio. In one embodiment of the invention the mRNA, to total lipid ratio is less than 0.06 w/w, preferably between 0.03 w/w and 0.04 w/w.

LNP Size

According to some embodiments, LNPs have a median diameter size of from about 50 nm to about 300 nm, such as from about 50 nm to about 250 nm, for example, from about 50 nm to about 200 nm.

According to some embodiments, smaller LNPs may be used. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, less than 975 um, In another embodiment, nucleic acids may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

As used herein, the mean diameter may be represented by the z-average as determined by dynamic light scattering as commonly known in the art.

According to some embodiments, the LNP may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm. In another preferred embodiment of the invention the lipid nanoparticles have a hydrodynamic diameter in the range from about 50 nm to about 300 nm, or from about 60 nm to about 250 nm, from about 60 nm to about 150 nm, or from about 60 nm to about 120 nm, respectively.

According to other embodiments, LNPs have a single mode particle size distribution (i.e., they are not bi- or poly-modal).

LNPs may further comprise one or more lipids and/or other components in addition to those mentioned above. Other lipids may be included in the liposome compositions for a variety of purposes, such as to prevent lipid oxidation or to attach ligands onto the liposome surface. Any of a number of lipids may be present in LNPs, including amphipathic, neutral, cationic, and anionic lipids. Such lipids can be used alone or in combination.

Additional components that may be present in a LNP include bilayer stabilizing components such as polyamide oligomers (see, e.g., U.S. Pat. No. 6,320,017, peptides, proteins, and detergents.

In one embodiment, the mRNA molecule of the present invention is formulated as a lipid nanoparticle.

In another embodiment, each individual mRNA molecule encoding a different mutant KRAS variant peptide is individually formulated in a lipid nanoparticle. In another embodiment one or more individual mRNA molecules, each encoding a different mutant KRAS variant peptide, are individually formulated as a lipid nanoparticle. In another embodiment, 1, 2, 3, 4, or 5 individual mRNA molecules, each encoding a different KRAS variant peptide, are individually formulated as a lipid nanoparticle. In another embodiment, 5 individual mRNA molecules, each encoding a different KRAS variant peptide, are individually formulated as a lipid nanoparticle.

In another embodiment, one or more individual mRNA molecules, each encoding a different KRAS variant peptide, is/are mixed prior to formulation as a lipid nanoparticle. In another embodiment, 1, 2, 3, 4, or 5 individual mRNA molecules, each encoding a particular KRAS variant peptide, is/are mixed prior to formulation as a lipid nanoparticle. In another embodiment, 5 individual mRNA molecules, each encoding a different KRAS variant peptide are mixed prior to formulation as a lipid nanoparticle.

In one embodiment, the lipid nanoparticle formulation comprises one or more artificial nucleic acid molecule of the invention, a cationic lipid, a phosphocholine (e.g., distearoylphophocholine), a pegylated lipid (e.g., 2-mPEG2000-n,n ditetradecylacetamide), a sterol (e.g., cholesterol) and a lipid derived from Formula (LNP-III) herein (e.g, the lipid of LNP III-3 in Table 4 herein). In another embodiment, the lipid nanoparticle formulation comprises one or more artificial nucleic acid molecule of the invention, distearoylphophocholine, 2-mPEG2000-n,n ditetradecylacetamide, cholesterol and the lipid of LNP III-3 in Table 4 herein.

In a further aspect, the present invention provides a pharmaceutical composition comprising the mRNA molecule according to the invention and/or the composition, and at least one pharmaceutically acceptable carrier, excipient, adjuvant or further component.

The pharmaceutical composition according to the invention comprises at least one mRNA molecule, and/or the composition of the invention in a "safe and therapeutically effective amount".

A "therapeutically effective amount" will furthermore vary in connection with the particular condition to be treated and also with the age, physical condition, body weight, sex and diet of the patient to be treated, the severity of the condition, the duration of the treatment, the nature of the accompanying therapy, of the particular pharmaceutically acceptable carrier and/or excipient used, the treatment regimen and similar factors. It may further vary depending on whether the employed mRNA molecule, is monocistronic, bi- or even multicistronic.

The pharmaceutical composition of the invention may further comprise at least one pharmaceutically acceptable excipient, carrier, adjuvant or further component (e.g. additional active agents, and the like), as described herein.

Preferably, the pharmaceutical composition according to the invention comprises at least one pharmaceutically acceptable carrier and/or excipient. The term "pharmaceutically acceptable" refers to a compound or agent that is compatible with the one or more active agent(s) (here: mRNA molecule, and/or composition) and does not interfere with and/or substantially reduce their pharmaceutical activities. Pharmaceutically acceptable carriers and/or excipient preferably have sufficiently high purity and sufficiently low toxicity to make them suitable for administration to a subject to be treated. Suitable pharmaceutical excipients and carriers are known to those of ordinary skill in the art, and non-limiting examples can be found in *Remington: The Science and Practice of Pharmacy*, $22^{nd}$ ed. (2012), A. Loyd et al., Pharmaceutical Press).

According to further embodiments, the pharmaceutical composition of the invention may further comprise at least one adjuvant. Suitable adjuvants are known to those of ordinary skill in the art, and non-limiting examples can be found in *Remington: The Science and Practice of Pharmacy*, $22^{nd}$ ed. (2012), A. Loyd et al., Pharmaceutical Press).

An "adjuvant" or "adjuvant component" in the broadest sense is typically a pharmacological and/or immunological agent that may modify, e.g. enhance, the effect of other active agents, e.g. therapeutic agents or vaccines. In this context, an "adjuvant" may be understood as any compound, which is suitable to support administration and delivery of the composition according to the invention. Specifically, an adjuvant may preferably enhance the immunostimulatory properties of the pharmaceutical composition to which it is added. Furthermore, such adjuvants may, without being bound thereto, initiate or increase an immune response of the innate immune system, i.e. a non-specific immune response.

"Adjuvants" typically do not elicit an adaptive immune response. Insofar, "adjuvants" do not qualify as antigens. In other words, when administered, the pharmaceutical composition typically initiates an adaptive immune response due to a variant peptide or protein, which is encoded by the at least one coding sequence of the mRNA molecule contained in the pharmaceutical composition. Additionally, an adjuvant present in the pharmaceutical composition may generate an (supportive) innate immune response.

In a preferred embodiment, the pharmaceutical composition of the present invention does not contain an adjuvant.

Biological Sequences 1-67

(muag 3'-UTR)
SEQ ID NO: 1
gcccgauggg ccucccaacg ggcccuccuc cccuccuugc accg (histone stem-loop)
SEQ ID NO: 2
caaaggcucu uuucagagcc acca (CTLA4 1-35)
SEQ ID NO: 3
Met Ala Cys Leu Gly Phe Gln Arg His Lys Ala Gln Leu Asn Leu Ala Thr Arg Thr Trp Pro Cys Thr Leu Leu Phe Phe Leu Leu Phe Ile Pro Val Phe Cys Ala (CTLA4 1-35)
SEQ ID NO: 4
auggcuugcc uuggauuuca gcggcacaag gcucagcuga accuggcuac caggaccugg cccugcacuc uccuguuuuu ucuucucuuc aucccugucu ucugcgca (CTLA4 1-35)
SEQ ID NO: 5
auggccugcc ugggcuucca gcgccacaag gcccagcuca accuggcgac ccggaccugg cccugcacgc uccuguucuu ccugcuguuc aucccggugu ucugcgca (CTLA4 1-35)
SEQ ID NO: 6
auggccugcc ugggcuucca gagacacaag gcucaacuca accuugcaac caggacaugg cccuguacuc uguuguuuuu cuuacuguuu aucccugugu ucugcgcc (CTLA4 1-35)
SEQ ID NO: 7
auggccugcc ugggcuucca gagacacaag gcccagcuga accuggccac cagaaccugg cccugcaccc ugcuguucuu ccugcuguuc auccccgugu ucugcgcc (Kras G12C)
SEQ ID NO: 8
Met Thr Glu Tyr Lys Leu Val Val Val Gly Ala Cys Gly Val Gly Lys Ser Ala Leu Thr Ile Gln Leu Ile Gln Asn His Phe Val (Kras G12D)
SEQ ID NO: 9
Met Thr Glu Tyr Lys Leu Val Val Val Gly Ala Asp Gly Val Gly Lys Ser Ala Leu Thr Ile Gln Leu Ile Gln Asn His Phe Val (Kras G12R)
SEQ ID NO: 10
Met Thr Glu Tyr Lys Leu Val Val Val Gly Ala Arg Gly Val Gly Lys Ser Ala Leu Thr Ile Gln Leu Ile Gln Asn His Phe Val (Kras G12V)
SEQ ID NO: 11
Met Thr Glu Tyr Lys Leu Val Val Val Gly Ala Val Gly Val Gly Lys Ser Ala Leu Thr Ile Gln Leu Ile Gln Asn His Phe Val (Kras G13D)
SEQ ID NO: 12
Met Thr Glu Tyr Lys Leu Val Val Val Gly Ala Gly Asp Val Gly Lys Ser Ala Leu Thr Ile Gln Leu Ile Gln Asn His Phe Val (Kras G12C)
SEQ ID NO: 13
Augacugaau auaaacuugu gguaguugga gcuugcggcg uaggcaagag ugccuugacg auacagcuaa uucagaauca uuuugug (Kras G12D)

-continued

SEQ ID NO: 14
augacugaau auaaacuugu gguaguugga gcugacggcg uaggcaagag ugccuugacg auacagcuaa
uucagaauca uuuugug
(Kras G12R)

SEQ ID NO: 15
augacugaau auaaacuugu gguaguugga gcuagaggcg uaggcaagag ugccuugacg auacagcuaa
uucagaauca uuuugug
(Kras G12V)

SEQ ID NO: 16
augacugaau auaaacuugu gguaguugga gcugugggcg uaggcaagag ugccuugacg auacagcuaa
uucagaauca uuuugug
(Kras G13D)

SEQ ID NO: 17
augacugaau auaaacuugu gguaguugga gcuggugacg uaggcaagag ugccuugacg auacagcuaa
uucagaauca uuuugug
(Kras G12C)

SEQ ID NO: 18
augaccgagu acaagcuggu ggucgugggc gccugcgggg ugggcaagag cgcccucacc auccagcuga
uccagaacca cuucguc
(Kras G12D)

SEQ ID NO: 19
augaccgagu acaagcuggu ggucgugggc gccgacgggg ugggcaagag cgcccucacc auccagcuga uccagaacca
cuucguc
(Kras G12R)

SEQ ID NO: 20
augaccgagu acaagcuggu ggucgugggc gcccgcgggg ugggcaagag cgcccucacc auccagcuga uccagaacca
cuucguc
(Kras G12V)

SEQ ID NO: 21
augaccgagu acaagcuggu ggucgugggc gccguggggg ucggcaagag cgcccucacc auccagcuga
uccagaacca cuucgug
(Kras G13D)

SEQ ID NO: 22
augaccgagu acaagcuggu ggucgugggc gccggggacg ugggcaagag cgcccucacc auccagcuga uccagaacca
cuucguc
(Kras G2C)

SEQ ID NO: 23
augaccgagu acaagcuggu ggucguuggc gccugcgggg ugggaaaaag cgcucucaca auccagcuua
uucaaaacca cuucgua
(Kras G12D)

SEQ ID NO: 24
augaccgagu acaagcuggu ggucguuggc gccgacgggg ugggaaaaag cgcucucaca auccagcuua uucaaaacca
cuucgua
(Kras G12R)

SEQ ID NO: 25
augaccgagu acaagcuggu ggucguuggc gccagagggg ugggaaaaag cgcucucaca auccagcuua uucaaaacca
cuucgua
(Kras G12V)

SEQ ID NO: 26
augaccgagu acaagcuggu ggucguuggc gccguggggg uaggaaaaag cgcucucaca auccagcuua
uucaaaacca cuucgug
(Kras G13D)

-continued

SEQ ID NO: 27
augaccgagu acaagcuggu ggucguuggc gccggggacg ugggaaaaag cgcucucaca auccagcuua uucaaaacca cuucgua (Kras G12C)

SEQ ID NO: 28
augaccgagu acaagcuggu gguggugggc gccugcggcg ugggcaagag cgcccugacc auccagcuga uccagaacca cuucgug (Kras G12D)

SEQ ID NO: 29
augaccgagu acaagcuggu gguggugggc gccgacggcg ugggcaagag cgcccugacc auccagcuga uccagaacca cuucgug (Kras G12R)

SEQ ID NO: 30
augaccgagu acaagcuggu gguggugggc gccagaggcg ugggcaagag cgcccugacc auccagcuga uccagaacca cuucgug (Kras G12V)

SEQ ID NO: 31
augaccgagu acaagcuggu gguggugggc gccgugggcg ugggcaagag cgcccugacc auccagcuga uccagaacca cuucgug (Kras G13D)

SEQ ID NO: 32
augaccgagu acaagcuggu gguggugggc gccggcgacg ugggcaagag cgcccugacc auccagcuga uccagaacca cuucgug (T helper epitope 1)

SEQ ID NO: 33
Ala Lys Phe Val Ala Ala Trp Thr Leu Lys Ala Ala Ala (T helper epitope 1)

SEQ ID NO: 34
gccaaguucg uggccgcgug gacccugaag gccgccgcc (Linker)

SEQ ID NO: 35
Gly Gly Gly Gly Ser Gly Gly Gly Gly Ser Gly Gly Gly Gly Ser (Linker)

SEQ ID NO: 36
ggcgggggcg ggagcggcgg gggcggcucc gggggcgggg gcagc (Linker)

SEQ ID NO: 37
ggcggaggcg gaucuggugg cggaggaagu gguggcggcg gaucu (Linker)

SEQ ID NO: 38
ggcggcggag gaucaggcgg ugguggaagc ggagguggug gaucu (Linker)

SEQ ID NO: 39
gguggugggug guucaggcgg cgguggguucu ggcgguggcg gcucu (Linker)

SEQ ID NO: 40
ggcgggggag guagcggcgg gggaggcucc gguggggggag gcucu (Linker)

SEQ ID NO: 41
ggcggcggcg gcagcggcgg cggcggcagc ggcggcggcg gcagc (CTLA4 162-223)

SEQ ID NO: 42
Phe Leu Leu Trp Ile Leu Ala Ala Val Ser Ser Gly Leu Phe Phe Tyr Ser Phe Leu Leu Thr Ala Val

Ser Leu Ser Lys Met Leu Lys Lys Arg Ser Pro Leu Thr Thr Gly Val Tyr Val Lys Met Pro Pro Thr

Glu Pro Glu Cys Glu Lys Gln Phe Gln Pro Tyr Phe Ile Pro Ile Asn (CTLA4 (162-223)

-continued

SEQ ID NO: 43 uuccuccucu ggauccuugc agcaguuagu ucgggguugu uuuuuuauag cuuucuccuc acagcuguuu cuuugagcaa aaugcuaaag aaaagaagcc cucuuacaac aggggucuau gugaaaaugc ccccaacaga gccagaaugu gaaaagcaau uucagccuua uuuuauuccc aucaauuga (CTLA4 162-223)

SEQ ID NO: 44 uuccugcucu ggauccuggc cgccgugucc uccggccugu ucuucuacag cuuccuccug accgcggucu cccugagcaa gaugcucaag aagcgcagcc cccugaccac ggggguguac gugaagaugc cgcccaccga gcccgagugc gagaagcagu uccagcccua cuucaucccg aucaacuga (CTLA4 162-223)

SEQ ID NO: 45 uuccuccucu ggauccucgc cgccgucucc uccggccucu ucuucuacuc cuuccuccuc accgccgucu cccucuccaa aaugcucaaa aaacgcuccc cccucaccac cggcgucuac gucaaaaugc cccccaccga acccgaaugc gaaaaacaau uccaacccua cuucaucccc aucaacuaa (CTLA4162-223)

SEQ ID NO: 46 uuccugcucu ggauccuugc cgcugugagc uccggccugu uuuucuacuc uuuucuauua accgcagucu cacugaguaa gauguugaaa aagagaagcc cccucacaac ugggguuuau gugaaaaugc cuccaacgga gccggaaugc gagaagcagu uccaacccua cuuuauuccu auaaacuga (CTLA4 162-223)

SEQ ID NO: 47 uuccugcugu ggauccuggc cgccgugagc agcggccugu ucuucuacag cuuccugcug accgccguga gccugagcaa gaugcugaag aagagaagcc cccugaccac cggcguguac gugaagaugc cccccaccga gcccgagugc gagaagcagu uccagcccua cuucauccccaucaacuga (Kras G12C construct)

SEQ ID NO: 48

Met Ala Cys Leu Gly Phe Gln Arg His Lys Ala Gln Leu Asn Leu Ala Thr Arg Thr Trp Pro Cys

Thr Leu Leu Phe Phe Leu Leu Phe Ile Pro Val Phe Cys Ala Gly Gly Gly Gly Ser Gly Gly Gly Gly

Ser Gly Gly Gly Gly Ser Met Thr Glu Tyr Lys Leu Val Val Val Gly Ala Cys Gly Val Gly Lys Ser

Ala Leu Thr Ile Gln Leu Ile Gln Asn His Phe Val Gly Gly Gly Gly Ser Gly Gly Gly Gly Ser Gly

Gly Gly Gly Ser Ala Lys Phe Val Ala Ala Trp Thr Leu Lys Ala Ala Ala Gly Gly Gly Gly Ser Gly

Gly Gly Gly Ser Gly Gly Gly Gly Ser Phe Leu Leu Trp Ile Leu Ala Ala Val Ser Ser Gly Leu Phe

Phe Tyr Ser Phe Leu Leu Thr Ala Val Ser Leu Ser Lys Met Leu Lys Lys Arg Ser Pro Leu Thr Thr

Gly Val Tyr Val Lys Met Pro Pro Thr Glu Pro Glu Cys Glu Lys Gln Phe Gln Pro Tyr Phe Ile Pro

Ile Asn (Kras G12D construct)

SEQ ID NO: 49

Met Ala Cys Leu Gly Phe Gln Arg His Lys Ala Gln Leu Asn Leu Ala Thr Arg Thr Trp Pro Cys

Thr Leu Leu Phe Phe Leu Leu Phe Ile Pro Val Phe Cys Ala Gly Gly Gly Gly Ser Gly Gly Gly Gly

Ser Gly Gly Gly Gly Ser Met Thr Glu Tyr Lys Leu Val Val Val Gly Ala Asp Gly Val Gly Lys Ser

Ala Leu Thr Ile Gln Leu Ile Gln Asn His Phe Val Gly Gly Gly Gly Ser Gly Gly Gly Gly Ser Gly

Gly Gly Gly Ser Ala Lys Phe Val Ala Ala Trp Thr Leu Lys Ala Ala Ala Gly Gly Gly Gly Ser Gly

Gly Gly Gly Ser Gly Gly Gly Gly Ser Phe Leu Leu Trp Ile Leu Ala Ala Val Ser Ser Gly Leu Phe

Phe Tyr Ser Phe Leu Leu Thr Ala Val Ser Leu Ser Lys Met Leu Lys Lys Arg Ser Pro Leu Thr Thr

Gly Val Tyr Val Lys Met Pro Pro Thr Glu Pro Glu Cys Glu Lys Gln Phe Gln Pro Tyr Phe Ile Pro

Ile Asn (Kras G12R construct)

-continued

SEQ ID NO: 50
Met Ala Cys Leu Gly Phe Gln Arg His Lys Ala Gln Leu Asn Leu Ala Thr Arg Thr Trp Pro Cys
Thr Leu Leu Phe Phe Leu Leu Phe Ile Pro Val Phe Cys Ala Gly Gly Gly Gly Ser Gly Gly Gly Gly
Ser Gly Gly Gly Gly Ser Met Thr Glu Tyr Lys Leu Val Val Val Gly Ala Arg Gly Val Gly Lys Ser
Ala Leu Thr Ile Gln Leu Ile Gln Asn His Phe Val Gly Gly Gly Gly Ser Gly Gly Gly Gly Ser Gly
Gly Gly Gly Ser Ala Lys Phe Val Ala Ala Trp Thr Leu Lys Ala Ala Ala Gly Gly Gly Gly Ser Gly
Gly Gly Gly Ser Gly Gly Gly Gly Ser Phe Leu Leu Trp Ile Leu Ala Ala Val Ser Ser Gly Leu Phe
Phe Tyr Ser Phe Leu Leu Thr Ala Val Ser Leu Ser Lys Met Leu Lys Lys Arg Ser Pro Leu Thr Thr
Gly Val Tyr Val Lys Met Pro Pro Thr Glu Pro Glu Cys Glu Lys Gln Phe Gln Pro Tyr Phe Ile Pro
Ile Asn (Kras G12V construct)

SEQ ID NO: 51
Met Ala Cys Leu Gly Phe Gln Arg His Lys Ala Gln Leu Asn Leu Ala Thr Arg Thr Trp Pro Cys
Thr Leu Leu Phe Phe Leu Leu Phe Ile Pro Val Phe Cys Ala Gly Gly Gly Gly Ser Gly Gly Gly Gly
Ser Gly Gly Gly Gly Ser Met Thr Glu Tyr Lys Leu Val Val Val Gly Ala Val Gly Val Gly Lys Ser
Ala Leu Thr Ile Gln Leu Ile Gln Asn His Phe Val Gly Gly Gly Gly Ser Gly Gly Gly Gly Ser Gly
Gly Gly Gly Ser Ala Lys Phe Val Ala Ala Trp Thr Leu Lys Ala Ala Ala Gly Gly Gly Gly Ser Gly
Gly Gly Gly Ser Gly Gly Gly Gly Ser Phe Leu Leu Trp Ile Leu Ala Ala Val Ser Ser Gly Leu Phe
Phe Tyr Ser Phe Leu Leu Thr Ala Val Ser Leu Ser Lys Met Leu Lys Lys Arg Ser Pro Leu Thr Thr
Gly Val Tyr Val Lys Met Pro Pro Thr Glu Pro Glu Cys Glu Lys Gln Phe Gln Pro Tyr Phe Ile Pro
Ile Asn (Kras G13D construct)

SEQ ID NO: 52
Met Ala Cys Leu Gly Phe Gln Arg His Lys Ala Gln Leu Asn Leu Ala Thr Arg Thr Trp Pro Cys
Thr Leu Leu Phe Phe Leu Leu Phe Ile Pro Val Phe Cys Ala Gly Gly Gly Gly Ser Gly Gly Gly Gly
Ser Gly Gly Gly Gly Ser Met Thr Glu Tyr Lys Leu Val Val Val Gly Ala Gly Asp Val Gly Lys Ser
Ala Leu Thr Ile Gln Leu Ile Gln Asn His Phe Val Gly Gly Gly Gly Ser Gly Gly Gly Gly Ser Gly
Gly Gly Gly Ser Ala Lys Phe Val Ala Ala Trp Thr Leu Lys Ala Ala Ala Gly Gly Gly Gly Ser Gly
Gly Gly Gly Ser Gly Gly Gly Gly Ser Phe Leu Leu Trp Ile Leu Ala Ala Val Ser Ser Gly Leu Phe
Phe Tyr Ser Phe Leu Leu Thr Ala Val Ser Leu Ser Lys Met Leu Lys Lys Arg Ser Pro Leu Thr Thr
Gly Val Tyr Val Lys Met Pro Pro Thr Glu Pro Glu Cys Glu Lys Gln Phe Gln Pro Tyr Phe Ile Pro
Ile Asn (Kras G12C construct)

SEQ ID NO: 53
auggccugcc ugggcuucca gcgccacaag gcccagcuca accuggcgac ccggaccugg cccugcacgc uccuguucuu
ccugcuguuc aucccggugu ucugcgcagg cggaggcgga ucugguggcg gaggaagugg uggcggcgga
ucuaugaccg aguacaagcu gguggucgug ggcgccugcg gggugggcaa gagcgcccuc accauccagc
ugauccagaa ccacuucguc ggcggcggag gaucaggcgg ugguggaagc ggaggguggug gaucugccaa
guucguggcc gcguggaccc ugaaggccgc cgccggguggu ggugguucag gcggcggugg uucuggcggu
ggcggcucuu uccugcucug gauccuggcc gccgugagcu ccggccuguu cuucuacagc uuccuccuga
ccgcggucuc ccugagcaag augcucaaga agcgcucccc ccugaccacg ggggguguacg ugaagaugcc gcccaccgag
cccgagugcg agaagcaguu ccagcccuac uucaucccga ucaacuga (Kras G12D construct)

-continued

SEQ ID NO: 54
auggccugcc ugggcuucca gcgccacaag gcccagcuca accuggcgac ccggaccugg cccugcacgc uccuguucuu
ccugcuguuc aucccggugu ucugcgcagg cggaggcgga ucugguggcg gaggaagugg uggcggcgga
ucuaugaccg aguacaagcu gguggucgug ggcgccgacg gggugggcaa gagcgcccuc accauccagc
ugauccagaa ccacuucguc ggcggcggag gaucaggcgg ugguggaagc ggagguggug gaucugccaa
guucguggcc gcguggaccc ugaaggccgc cgccggugguu gguggguucag gcggcggugg uucuggcggu
ggcggcucuu uccugcucug gauccuggcc gccgugagcu ccggccuguu cuucuacagc uuccuccuga
ccgcggucuc ccugagcaag augcucaaga agcgcucccc ccugaccacg ggggguguacg ugaagaugcc gcccaccgag
cccgagugcg agaagcaguu ccagcccuac uucaucccga ucaacuga (Kras G12R construct)

SEQ ID NO: 55
auggccugcc ugggcuucca gcgccacaag gcccagcuca accuggcgac ccggaccugg cccugcacgc uccuguucuu
ccugcuguuc aucccggugu ucugcgcagg cggaggcgga ucugguggcg gaggaagugg uggcggcgga
ucuaugaccg aguacaagcu gguggucgugggcgcccgcg gggugggcaa gagcgcccuc accauccagc ugauccagaa
ccacuucguc ggcggcggag gaucaggcgg ugguggaagc ggagguggug gaucugccaa
guucguggccgcguggaccc ugaaggccgc cgccggugguu gguggguucag gcggcggugg uucuggcggu
ggcggcucuu uccugcucug gauccuggcc gccgugagcu ccggccuguu cuucuacagc uuccuccuga
ccgcggucuc ccugagcaag augcucaaga agcgcucccc ccugaccacg ggggguguacg ugaagaugcc gcccaccgag
cccgagugcg agaagcaguu ccagcccuac uucaucccga ucaacuga (Kras G12V construct)

SEQ ID NO: 56
auggccugcc ugggcuucca gcgccacaag gcccagcuca accuggcgac ccggaccugg cccugcacgc uccuguucuu
ccugcuguuc aucccggugu ucugcgcagg cggaggcgga ucugguggcg gaggaagugg uggcggcgga
ucuaugaccg aguacaagcu gguggucgug ggcgccgugg gggucggcaa gagcgcccuc accauccagc
ugauccagaa ccacuucgug ggcggcggag gaucaggcgg ugguggaagc ggagguggug gaucugccaa
guucguggcc gcguggaccc ugaaggccgc cgccggugguu gguggguucag gcggcggugg uucuggcggu
ggcggcucuu uccugcucug gauccuggcc gccgugagcu ccggccuguu cuucuacagc uuccuccuga
ccgcggucuc ccugagcaag augcucaaga agcgcucccc ccugaccac gggggguguacg ugaagaugcc gcccaccgag
cccgagugcg agaagcaguu ccagcccuac uucaucccga ucaacuga (Kras G13D construct)

SEQ ID NO: 57
auggccugcc ugggcuucca gcgccacaag gcccagcuca accuggcgac ccggaccugg cccugcacgc uccuguucuu
ccugcuguuc aucccggugu ucugcgcagg cggaggcgga ucugguggcg gaggaagugg uggcggcgga
ucuaugaccg aguacaagcu gguggucgug ggcgccgggg acgugggcaa gagcgcccuc accauccagc
ugauccagaa ccacuucguc ggcggcggag gaucaggcgg ugguggaagc ggagguggug gaucugccaa
guucguggcc gcguggaccc ugaaggccgc cgccggugguu gguggguucag gcggcggugg uucuggcggu
ggcggcucuu uccugcucug gauccuggcc gccgugagcu ccggccuguu cuucuacagc
uuccuccuga ccgcggucuc ccugagcaag augcucaaga agcgcucccc ccugaccacg ggggguguacg ugaagaugcc
gcccaccgag cccgagugcg agaagcaguu ccagcccuac uucaucccga ucaacuga (Kras G12C mRNA construct)

SEQ ID NO: 58
gggagaaagc uuaccauggc cugccugggc uuccagcgcc acaaggccca gcucaaccug gcgacccgga ccuggcccug
cacgcuccug uucuuccugc uguucauccc gguguucugc gcaggcggag gcggaucugg uggcggagga
agugguggcg gcggaucuau gaccgaguac aagcuggugg ucgugggcgc cugcggggug ggcaagagcg
cccucaccau ccagcugauc cagaaccacu ucgucggcgg cggaggauca ggcgguggug gaagcggagg -continued uggugga ucu gccaaguucg uggccgcgug gacccugaag gccgccgccg gugguggugg uucaggcggc ggugguucug gcgguggcgg cucuuuccug cucuggaucc uggccgccgu gagcuccggc cuguucuucu acagcuuccu ccugaccgcg gucucccuga gcaagaugcu caagaagcgc uccccccuga ccacgggggu guacgugaag augccgccca ccgagcccga gugcgagaag caguuccagc ccuacuucau cccgaucaac ugaggacuag uuauaagacu gacuagcccg augggccucc caacgggccc uccuccccuc cuugcaccga gauuaauaga ucuaaaaaaa aaaaaaaaaa aaaaaaaaaa aaaaaaaaaa aaaaaaaaaa aaaaaaaaaa aaaaaaaugc aucccccccc cccccccccc cccccccccc cccaaaggcu cuuuucagag ccaccagaau u (Kras G12D mRNA construct)

SEQ ID NO: 59 gggagaaagc uuaccauggc cugccugggc uuccagcgcc acaaggccca gcucaaccug gcgacccgga ccuggcccug cacgcuccug uucuuccugc uguucauccc gguguucugc gcaggcggag gcggaucugg uggcggagga aguggugg cg gcggaucuau gaccgaguac aagcuggugg ucgugggcgc cgacggggug ggcaagagcg cccucaccau ccagcugauc cagaaccacu ucgucggcgg cggaggauca ggcgguggug gaagcggagg uggugga ucu gccaaguucg uggccgcgug gacccugaag gccgccgccg gugguggugg uucaggcggc ggugguucug gcgguggcgg cucuuuccug cucuggaucc uggccgccgu gagcuccggc cuguucuucu acagcuuccu ccugaccgcg gucucccuga gcaagaugcu caagaagcgc uccccccuga ccacgggggu guacgugaag augccgccca ccgagcccga gugcgagaag caguuccagc ccuacuucau cccgaucaac ugaggacuag uuauaagacu gacuagcccg augggccucc caacgggccc uccuccccuc cuugcaccga gauuaauaga ucuaaaaaaa aaaaaaaaaa aaaaaaaaaa aaaaaaaaaa aaaaaaaaaa aaaaaaaaaa aaaaaaaugc aucccccccc cccccccccc cccccccccc cccaaaggcu cuuuucagag ccaccagaau u (Kras G12R mRNA construct)

SEQ ID NO: 60 gggagaaagc uuaccauggc cugccugggc uuccagcgcc acaaggccca gcucaaccug gcgacccgga ccuggcccug cacgcuccug uucuuccugc uguucauccc gguguucugcgcaggcggag gcggaucugg uggcggagga aguggugg cg gcggaucuau gaccgaguac aagcuggugg ucgugggcgc ccgcggggug ggcaagagcg cccucaccau ccagcugauc cagaaccacu ucgucggcgg cggaggauca ggcgguggug gaagcggagg uggugga ucu gccaaguucg uggccgcgug gacccugaag gccgccgccg gugguggugg uucaggcggc ggugguucug gcgguggcgg cucuuuccug cucuggaucc uggccgccgu gagcuccggc cuguucuucu acagcuuccu ccugaccgcg gucucccuga gcaagaugcu caagaagcgc uccccccuga ccacgggggu guacgugaag augccgccca ccgagcccga gugcgagaag caguuccagc ccuacuucau cccgaucaac ugaggacuag uuauaagacu gacuagcccg augggccucc caacgggccc uccuccccuc cuugcaccga gauuaauaga ucuaaaaaaa aaaaaaaaaa aaaaaaaaaa aaaaaaaaaa aaaaaaaaaa aaaaaaaaaa aaaaaaaugc aucccccccc cccccccccc cccccccccc cccaaaggcu cuuuucagag ccaccagaau u (Kras G12V mRNA construct)

SEQ ID NO: 61 gggagaaagc uuaccauggc cugccugggc uuccagcgcc acaaggccca gcucaaccug gcgacccgga ccuggcccug cacgcuccug uucuuccugc uguucauccc gguguucugc gcaggcggag gcggaucugg uggcggagga aguggugg cg gcggaucuau gaccgaguac aagcuggugg ucgugggcgc cgugggggug ggcaagagcg cccucaccau ccagcugauc cagaaccacu ucgugggcgg cggaggauca ggcgguggug gaagcggagg uggugga ucu gccaaguucg uggccgcgug gacccugaag gccgccgccg gugguggugg uucaggcggc ggugguucug gcgguggcgg cucuuuccug cucuggaucc uggccgccgu gagcuccggc cuguucuucu acagcuuccu ccugaccgcg gucucccuga gcaagaugcu caagaagcgc uccccccuga ccacgggggu guacgugaag augccgccca ccgagcccga gugcgagaag caguuccagc ccuacuucau cccgaucaac ugaggacuag uuauaagacu -continued gacuagcccg augggccucc caacgggccc uccuccccuc cuugcaccga gauuaauaga ucuaaaaaaa aaaaaaaaaa aaaaaaaaaa aaaaaaaaaa aaaaaaaaaa aaaaaaaaaa aaaaaaaugc auccccccc cccccccccc cccccccccc cccaaaggcu cuuuucagag ccaccagaau u (Kras G13D mRNA construct)

SEQ ID NO: 62 gggagaaagc uuaccauggc cugccugggc uuccagcgcc acaaggccca gcucaaccug gcgacccgga ccuggcccug cacgcuccug uucuuccugc uguucauccc gguguucugc gcaggcggag gcggaucugg uggcggagga agugguggcg gcggaucuau gaccgaguac aagcuggugg ucgugggcgc cggggacgug ggcaagagcg cccucaccau ccagcugauc cagaaccacu ucgucggcgg cggaggauca ggcgguggug gaagcggagg ugguggaucu gccaaguucg uggccgcgug gacccugaag gccgccgccg gugguggugg uucaggcggc ggugguucug gcgguggcgg cucuuuccug cucuggaucc uggccgccgu gagcuccggc cuguucuucu acagcuuccu ccugaccgcg gucucccuga gcaagaugcu caagaagcgc uccccccuga ccacgggggu guacgugaag augccgccca ccgagcccga gugcgagaag caguuccagc ccuacuucau cccgaucaac ugaggacuag uuauaagacu gacuagcccg augggccucc caacgggccc uccuccccuc cuugcaccga gauuaauaga ucuaaaaaaa aaaaaaaaaa aaaaaaaaaa aaaaaaaaaa aaaaaaaaaa aaaaaaaaaa aaaaaaaugc auccccccc cccccccccc cccccccccc cccaaaggcu cuuuucagag ccaccagaau u (Kras G12C mRNA construct)

SEQ ID NO: 63 gggagaaagc uuaccauggc cugccugggc uuccagcgcc acaaggccca gcucaaccug gcgacccgga ccuggcccug cacgcuccug uucuuccugc uguucauccc gguguucugc gcaggcggag gcggaucugg uggcggagga agugguggcg gcggaucuau gaccgaguac aagcuggugg ucgugggcgc cugcgggggug ggcaagagcg cccucaccau ccagcugauc cagaaccacu ucgucggcgg cggaggauca ggcgguggug gaagcggagg ugguggaucu gccaaguucg uggccgcgug gacccugaag gccgccgccg gugguggugg uucaggcggc ggugguucug gcgguggcgg cucuuuccug cucuggaucc uggccgccgu gagcuccggc cuguucuucu acagcuuccu ccugaccgcg gucucccuga gcaagaugcu caagaagcgc uccccccuga ccacgggggu guacgugaag augccgccca ccgagcccga gugcgagaag caguuccagc ccuacuucau cccgaucaac ugaggacuag uuauaagacu gacuagcccg augggccucc caacgggccc uccuccccuc cuugcaccga gauuaauaaa aaaaaaaaaa aaaaaaaaaa aaaaaaaaaa aaaaaaaaaa aaaaaaaaaa aaaaaaaaaa augcaucccc cccccccccc cccccccccc cccccccaaa ggcucuuuuc agagccacca gaauu (Kras G12D mRNA construct)

SEQ ID NO: 64 gggagaaagc uuaccauggc cugccugggc uuccagcgcc acaaggccca gcucaaccug gcgacccgga ccuggcccug cacgcuccug uucuuccugc uguucauccc gguguucugc gcaggcggag gcggaucugg uggcggagga agugguggcg gcggaucuau gaccgaguac aagcuggugg ucgugggcgc cgacggggug ggcaagagcg cccucaccau ccagcugauc cagaaccacu ucgucggcgg cggaggauca ggcgguggug gaagcggagg ugguggaucu gccaaguucg uggccgcgug gacccugaag gccgccgccg gugguggugg uucaggcggc ggugguucug gcgguggcgg cucuuuccug cucuggaucc uggccgccgu gagcuccggc cuguucuucu acagcuuccu ccugaccgcg gucucccuga gcaagaugcu caagaagcgc uccccccuga ccacgggggu guacgugaag augccgccca ccgagcccga gugcgagaag caguuccagc ccuacuucau cccgaucaac ugaggacuag uuauaagacu gacuagcccg augggccucc caacgggccc uccuccccuc cuugcaccga gauuaauaaa aaaaaaaaaa aaaaaaaaaa aaaaaaaaaa aaaaaaaaaa aaaaaaaaaa aaaaaaaaaa augcaucccc cccccccccc cccccccccc cccccccaaa ggcucuuuuc agagccacca gaauu (Kras G12R mRNA construct)

-continued

SEQ ID NO: 65 gggagaaagc uuaccauggc cugccugggc uuccagcgcc acaaggccca gcucaaccug gcgacccgga ccuggcccug
cacgcuccug uucuuccugc uguucauccc gguguucugc gcaggcggag gcggaucugg uggcggagga
agugguggcg gcggaucuau gaccgaguac aagcuggugg ucgugggcgc ccgcggggug ggcaagagcg
cccucaccau ccagcugauc cagaaccacu ucgucggcgg cggaggauca ggcgguggug gaagcggagg
ugguggaucu gccaaguucg uggccgcgug gacccugaag gccgccgccg gugguggugg uucaggcggc
ggugguucug gcgguggcgg cucuuuccug cucuggaucc uggccgccgu gagcuccggc cuguucuucu
acagcuuccu ccugaccgcg gucucccuga gcaagaugcu caagaagcgc uccccccuga ccacgggggu guacgugaag
augccgccca ccgagcccga gugcgagaag caguuccagc ccuacuucau cccgaucaac ugaggacuag uuauaagacu
gacuagcccg augggccucc caacgggccc uccuccccuc cuugcaccga gauuaauaaa aaaaaaaaaa aaaaaaaaaa
aaaaaaaaaa aaaaaaaaaa aaaaaaaaaa aaaaaaaaaa augcaucccc cccccccccc cccccccccc cccccccaaa
ggcucuuuuc agagccacca gaauu (Kras G12V mRNA construct)

SEQ ID NO: 66 gggagaaagc uuaccauggc cugccugggc uuccagcgcc acaaggccca gcucaaccug gcgacccgga ccuggcccug
cacgcuccug uucuuccugc uguucauccc gguguucugc gcaggcggag gcggaucugg uggcggagga
agugguggcg gcggaucuau gaccgaguac aagcuggugg ucgugggcgc cgugggggUc ggcaagagcg
cccucaccau ccagcugauc cagaaccacu ucgugggcgg cggaggauca ggcgguggug gaagcggagg
ugguggaucu gccaaguucg uggccgcgug gacccugaag gccgccgccg gugguggugg uucaggcggc
ggugguucug gcgguggcgg cucuuuccug cucuggaucc uggccgccgu gagcuccggc cuguucuucu
acagcuuccu ccugaccgcg gucucccuga gcaagaugcu caagaagcgc uccccccuga ccacgggggu guacgugaag
augccgccca ccgagcccga gugcgagaag caguuccagc ccuacuucau cccgaucaac ugaggacuag uuauaagacu
gacuagcccg augggccucc caacgggccc uccuccccuc cuugcaccga gauuaauaaa aaaaaaaaaa aaaaaaaaaa
aaaaaaaaaa aaaaaaaaaa aaaaaaaaaa aaaaaaaaaa augcaucccc cccccccccc cccccccccc cccccccaaa
ggcucuuuuc agagccacca gaauu (Kras G13D mRNA construct)

SEQ ID NO: 67 gggagaaagc uuaccauggc cugccugggc uuccagcgcc acaaggccca gcucaaccug gcgacccgga ccuggcccug
cacgcuccug uucuuccugc uguucauccc gguguucugc gcaggcggag gcggaucugg uggcggagga
agugguggcg gcggaucuau gaccgaguac aagcuggugg ucgugggcgc cggggacgug ggcaagagcg
cccucaccau ccagcugauc cagaaccacu ucgucggcgg cggaggauca ggcgguggug gaagcggagg
ugguggaucu gccaaguucg uggccgcgug gacccugaag gccgccgccg gugguggugg uucaggcggc
ggugguucug gcgguggcgg cucuuuccug cucuggaucc uggccgccgu gagcuccggc cuguucuucu
acagcuuccu ccugaccgcg gucucccuga gcaagaugcu caagaagcgc uccccccuga ccacgggggu guacgugaag
augccgccca ccgagcccga gugcgagaag caguuccagc ccuacuucau cccgaucaac ugaggacuag uuauaagacu
gacuagcccg augggccucc caacgggccc uccuccccuc cuugcaccga gauuaauaaa aaaaaaaaaa aaaaaaaaaa
aaaaaaaaaa aaaaaaaaaa aaaaaaaaaa aaaaaaaaaa augcaucccc cccccccccc cccccccccc cccccccaaa
ggcucuuuuc agagccacca gaauu

We claim:

1. An mRNA molecule comprising an mRNA sequence encoding an amino acid sequence comprising a CTLA4 signal peptide, a KRAS variant peptide, PADRE-derived T helper epitope sequence, and a CTLA4 transmembrane domain.

2. The mRNA molecule according to claim 1, wherein the KRAS variant peptide comprises the KRAS G12C variant amino acid residue, the KRAS G12D variant amino acid residue, the KRAS G12V variant amino acid residue, the KRAS G12R variant amino acid residue, or the KRAS G13D variant amino acid residue.

3. The mRNA molecule according to claim 1, further comprising an alpha-globin 3' UTR element.

4. The mRNA molecule according to claim 3, wherein the mRNA encoding a KRAS variant peptide is located 5' of the alpha-globin 3' UTR element.

5. The mRNA molecule according to claim 1, wherein the KRAS variant peptide comprises the sequence of SEQ ID NO: 8, SEQ ID NO: 9, SEQ ID NO: 10, SEQ ID NO: 11 or SEQ ID NO: 12.

6. The mRNA molecule according to claim 1, wherein the molecule comprises SEQ ID NO: 53, SEQ ID NO: 54, SEQ ID NO: 55, SEQ ID NO: 56 or SEQ ID NO: 57.

7. The mRNA molecule according to claim 1, wherein the mRNA is set forth in SEQ ID NO: 63, SEQ ID NO: 64, SEQ ID NO: 65, SEQ ID NO: 66 or SEQ ID NO: 67.

8. The mRNA molecule according to claim 1, wherein the mRNA molecule is set forth in SEQ ID NO: 58, SEQ ID NO: 59, SEQ ID NO: 60, SEQ ID NO: 61 or SEQ ID NO: 62.

9. The mRNA molecule according to claim 1, wherein the mRNA molecule encodes a KRAS variant peptide set forth in SEQ ID NO: 48, SEQ ID NO: 49, SEQ ID NO: 50, SEQ ID NO: 51 or SEQ ID NO: 52.

10. A pharmaceutical composition comprising the mRNA molecule of claim 1, and one or more pharmaceutically acceptable carriers or excipients.

11. The pharmaceutical composition of claim 10, wherein the composition comprises 1, 2, 3, 4 or 5 different mRNA molecules, wherein each mRNA molecule encodes a different KRAS variant peptide.

12. The pharmaceutical composition of claim 11, further comprising a cationic lipid, a sterol, a neutral lipid, and a PEG lipid.

13. The pharmaceutical composition according to claim 12, wherein the PEG lipid is of the formula:

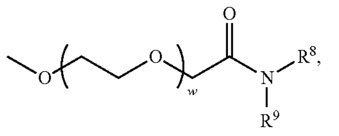

wherein $R^8$ and $R^9$ are each independently a straight or branched, saturated or unsaturated alkyl chain containing from 10 to 30 carbon atoms, wherein the alkyl chain is optionally interrupted by one or more ester bonds; and w has a mean value ranging from 30 to 60.

14. The pharmaceutical composition according to claim 12, wherein the neutral lipid is distearoylphophocholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1carboxylate (DOPE-mal), dipalmitoyl phosphatidyl ethanolamine (DPPE), dimyristoyl-phosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE), or 1,2-dielaidoyl-sn-glycero-3-phophoethanolamine (transDOPE).

15. The pharmaceutical composition according to claim 12, wherein the sterol is cholesterol.

16. The pharmaceutical composition according to claim 12, wherein the PEG lipid is 2-mPEG2000-n,n ditetradecylacetamide, the neutral lipid is 1,2-distearoyl-sn-glycero-3-phosphocholine, and the sterol is cholesterol.

17. The pharmaceutical composition according to claim 12, comprising a molar ratio of about 20-60% cationic lipid, 5-25% neutral lipid, 25-55% sterol, and 0.5-15% PEG-lipid.

18. A kit comprising the mRNA of claim 1 and optionally instructions with information on the administration and dosage of the mRNA molecule.

19. A method of treating cancer, comprising administering to a patient in need thereof an effective amount of the mRNA molecule of claim 1, wherein the cancer is a solid tumor cancer that is bladder cancer, breast cancer, cervical cancer, colorectal cancer, endometrial cancer, head and neck cancer, liver cancer, lung cancer, melanoma, ovarian cancer, pancreatic cancer, prostate cancer, renal cancer, gastric cancer, testicular cancer, thyroid cancer, or uterine cancer.

* * * * *